(12) United States Patent
Zhang et al.

(10) Patent No.: US 9,862,682 B2
(45) Date of Patent: Jan. 9, 2018

(54) FUNCTIONALIZED PEGYLATED CYANINE COMPOUNDS, PHARMACEUTICAL COMPOSITIONS, AND METHODS OF USE THEREOF

(71) Applicant: BroadPharm, San Diego, CA (US)

(72) Inventors: Hanzhong Zhang, San Diego, CA (US); Hongyuan Chen, Irvine, CA (US); Mikhail Kondratenko, San Diego, CA (US); Si Wang, San Diego, CA (US); Qiwen Zhong, Temecula, CA (US)

(73) Assignee: BROADPHARM, San Diego, CA (US)

( * ) Notice: Subject to any disclaimer, the term of this patent is extended or adjusted under 35 U.S.C. 154(b) by 0 days.

(21) Appl. No.: 15/400,892

(22) Filed: Jan. 6, 2017

(65) Prior Publication Data

US 2017/0197916 A1    Jul. 13, 2017

Related U.S. Application Data

(60) Provisional application No. 62/276,462, filed on Jan. 8, 2016.

(51) Int. Cl.

| | | |
|---|---|---|
| C07D 209/08 | (2006.01) |
| C07D 403/14 | (2006.01) |
| C07D 495/04 | (2006.01) |
| C07D 417/06 | (2006.01) |
| A61K 49/00 | (2006.01) |
| C09B 69/10 | (2006.01) |
| C09K 11/06 | (2006.01) |

(52) U.S. Cl.
CPC ........ C07D 209/08 (2013.01); A61K 49/0032 (2013.01); A61K 49/0052 (2013.01); A61K 49/0054 (2013.01); C07D 403/14 (2013.01); C07D 417/06 (2013.01); C07D 495/04 (2013.01); C09B 69/105 (2013.01); C09K 11/06 (2013.01); *C09K 2211/14* (2013.01)

(58) Field of Classification Search
CPC .......................... C07D 209/08; A61K 49/0032
See application file for complete search history.

(56) References Cited

U.S. PATENT DOCUMENTS

| | | | |
|---|---|---|---|
| 4,906,541 A | 3/1990 | Dust | |
| 5,069,991 A | 12/1991 | Leyrer | |
| 6,649,337 B2 * | 11/2003 | Hioki | G03C 1/49854 430/572 |
| 7,018,775 B2 | 3/2006 | Tao | |
| 8,889,884 B1 | 11/2014 | Hermanson | |
| 2002/0044909 A1 | 4/2002 | Achilefu | |
| 2003/0143159 A1 | 7/2003 | Achilefu | |
| 2003/0165432 A1 | 9/2003 | Achilefu | |
| 2004/0081622 A1 | 4/2004 | Achilefu | |
| 2004/0141920 A1 | 7/2004 | Achilefu | |
| 2004/0186278 A1 | 9/2004 | Chen | |
| 2004/0202611 A1 | 10/2004 | Achilefu | |
| 2004/0213740 A1 | 10/2004 | Achilefu | |
| 2004/0241095 A1 | 12/2004 | Achilefu | |
| 2005/0281741 A1 | 12/2005 | Achilefu | |
| 2008/0138820 A1 | 6/2008 | Thomas | |
| 2008/0233050 A1 | 9/2008 | Achilefu | |
| 2009/0098410 A1 | 4/2009 | Nishimoto | |
| 2012/0156140 A1 | 6/2012 | Hermanson | |
| 2013/0052130 A1 | 2/2013 | Davis | |
| 2013/0164678 A1 | 6/2013 | Nam | |
| 2013/0230466 A1 | 9/2013 | Hermanson | |
| 2014/0255312 A1 | 9/2014 | Hermanson | |
| 2015/0073154 A1 | 3/2015 | Davis | |
| 2017/0158672 A9 | 6/2017 | Hermanson | |

FOREIGN PATENT DOCUMENTS

| | | |
|---|---|---|
| EP | 1439214 A2 | 7/2004 |
| EP | 1559374 A1 | 8/2005 |
| EP | 1792949 B1 | 12/2006 |
| EP | 2270106 A3 | 6/2011 |
| WO | WO0016806 A1 | 3/2000 |
| WO | WO02/26891 A1 | 4/2002 |
| WO | WO02/32285 A2 | 4/2002 |
| WO | WO02/32421 A1 | 4/2002 |
| WO | WO02/32464 A1 | 4/2002 |
| WO | WO02/32466 A1 | 4/2002 |
| WO | WO03/032901 A2 | 4/2003 |
| WO | WO03/032902 A2 | 4/2003 |
| WO | WO03/065888 A1 | 8/2003 |
| WO | WO2005005483 A1 | 1/2005 |
| WO | WO2005005985 A1 | 1/2005 |
| WO | WO2005/014723 A1 | 2/2005 |
| WO | WO2006123807 A1 | 11/2006 |
| WO | WO2007000349 A3 | 1/2007 |
| WO | WO2007/100392 A2 | 9/2007 |

(Continued)

*Primary Examiner* — Golam M M Shameem

(74) *Attorney, Agent, or Firm* — Gordon Rees Scully Mansukhani LLP; Kathryn K. Hull

(57) ABSTRACT

Provided herein are functionalized pegylated cyanine compounds containing a reactive group suitable for labeling a biomolecule or pharmaceutical compositions and methods of use thereof. In one embodiment, the compounds are based on formula I shown below.

(I)

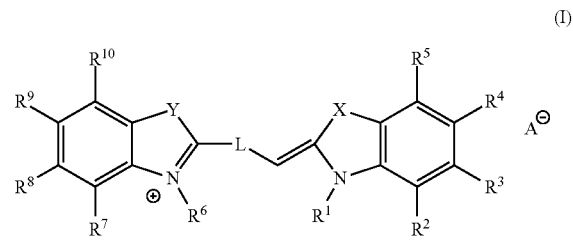

In other embodiments, the compounds can be pegylated at one or more of the following locations $R^1$, $R^4$, $R^6$, $R^9$, or L.

20 Claims, No Drawings

(56) References Cited

FOREIGN PATENT DOCUMENTS

| WO | WO2007/105829 A1 | 9/2007 |
| WO | WO2009078970 A1 | 6/2009 |
| WO | WO2011151287 A1 | 12/2011 |
| WO | WO2012037928 A2 | 3/2012 |
| WO | WO2012041292 A3 | 4/2012 |
| WO | WO2012129128 A1 | 9/2012 |
| WO | WO2013044156 A1 | 3/2013 |
| WO | WO2013109859 A1 | 7/2013 |
| WO | WO2014006589 A3 | 1/2014 |

* cited by examiner

FUNCTIONALIZED PEGYLATED CYANINE COMPOUNDS, PHARMACEUTICAL COMPOSITIONS, AND METHODS OF USE THEREOF

CROSS REFERENCE TO RELATED APPLICATIONS

This application claims the benefit of U.S. provisional application No. 62/276,462, filed on Jan. 8, 2016 and entitled, "Functionalized Pegylated Cyanine Compunds, Pharmaceutical Compositions, and Methods of use Thereof." The entire contents of the related application are incorporated by reference herein.

FIELD

Provided herein are functionalized pegylated cyanine compounds containing a reactive group suitable for labeling a biomolecule, and pharmaceutical compositions and methods of use thereof.

BACKGROUND

Cyanine dyes play an indispensable role in biomedical applications, particularly in fluorescence detection of antibodies and DNA, the imaging of biological targets in vivo, and fluorescent labeling compounds for proteins. This is due to their excellent spectral properties, including large molar extinction coefficients and broad wavelength tunabilities. The labeling of cyanine dyes to biomolecules often involves covalent conjugations in aqueous buffer solutions under mild conditions. However, planarity of the cyanine π system leads to aggregations and dimer formations in aqueous solution. Due to insufficient hydrophilicity, non-specific interactions with various surfaces have been observed, resulting in problems with purifications of the corresponding cyanine-labeled bioconjugations, and an unsatisfactory signal to noise ratio.

Functionalized polyethylene glycol (PEG) linkers with reactive groups are important building blocks with a wide range of applications in biochemical and pharmaceutical industries. PEG is non-toxic, non-immunogenic, non-antigenic, and highly soluble in water. Incorporations of functionalized PEG linkers into cyanine dyes not only improve dye water solubility, but also introduce functionalities in cyanine dyes for further conjugation with biomolecules.

SUMMARY OF THE DISCLOSURE

Provided herein is a compound of Formula I:

(I)

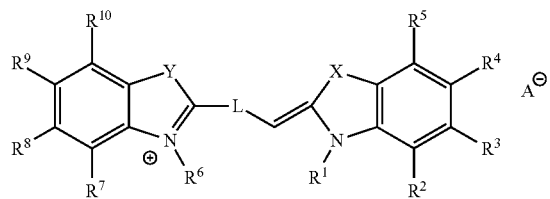

or a tautomer or a mixture of two or more tautomers thereof; or a pharmaceutically acceptable solvate, or hydrate thereof;

wherein:
A is an anion bearing a negative charge;
L is

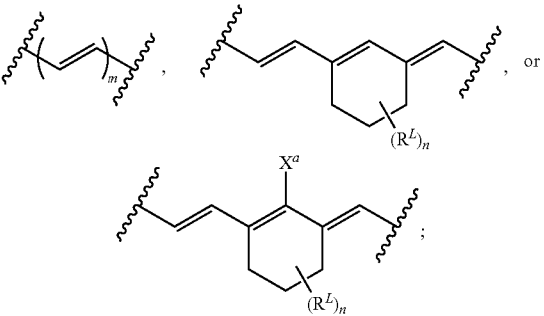

wherein:
each $R^L$ is independently (a) hydrogen, deuterium, azido, cyano, halo, nitro, oxo, sulfo, —$OPO_3H_2$, or —$PO_3H_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;

$X^a$ is (a) hydrogen, deuterium, azido, cyano, halo, nitro, oxo, sulfo, $OPO_3H_2$, or —$PO_3H_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl, each of which is optionally substituted with one or more substituents Q; (c) —$C(R^{1a}R^{1b})$, —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$; (d) —$(CH_2CH_2O)_p$-$L^1$-$Z^1$, —$(CH_2CH_2O)_p$—COOH, —$(CH_2CH_2O)_p$—$N_3$, —$(CH_2CH_2O)_p$—OH, —$(CH_2CH_2O)_p$-alkyne, —$(CH_2CH_2O)_p$-biotin, —$(CH_2CH_2O)_p$-NHS ester, —$(CH_2CH_2O)_p$-amine, —$(CH_2CH_2O)_p$-DBCO, —$(CH_2CH_2O)_p$-Fmoc, —$(CH_2CH_2O)_p$-aldehyde, —$(CH_2CH_2O)_p$-phosphonate, —$(CH_2CH_2O)_p$-tosylate, —$(CH_2CH_2O)_p$-FPF ester, —$(CH_2CH_2O)_p$-Boc, —$(CH_2CH_2O)_p$-aminooxy, —$(CH_2CH_2O)_p$-bromo, —$(CH_2CH_2O)_p$-mal, or —$(CH_2CH_2O)_p$-propargyl; or (e) carboxycylic acid, amine, azide, DBCO, hydrazide, maleimide, NHS ester, TCO, tetrazine, or biotin;

m is an integer of 1, 2, or 3; and
n is an integer of 0, 1, 2, 3, 4, 5, 6, or 7;
X and Y are each independently $C(R^{Xa}R^{Xb})$, O, S, or $NR^{Xc}$;
wherein:
$R^{Xa}$ and $R^{Xb}$ are each independently (a) hydrogen or deuterium; or (b) $C_{1-10}$ alkyl, $C_{2-10}$ alkenyl, $C_{2-10}$ alkynyl, $C_{3-hd\ 15}$ cycloalkyl, $C_{6-20}$ aryl, $C_{7-20}$ aralkyl, heteroaryl, or heterocyclyl; and $R^{Xc}$ is (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; or (c) —C(O) $R^{1a}$, —C(O)O$R^{1a}$, —C(O)$_{NR}{}^{1b}R^{1c}$, —C(N$R^{1a}$) N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^1$ is (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O) O$R^{1a}$, —C(O)N$R^{1b}R^{1c}$, —C(N$R^{1a}$)N$R^{1b}R^{1c}$, —S(O)$R^{1a}$, —S(O)$_2R^{1a}$, —S(O)$_2R^{1a}$, —S(O)N$R^{1b}R^{1c}$, or —S(O)$_2$ N$R^{1b}R^{1c}$; or (d) —(CH$_2$CH$_2$O)$_p$-L$^1$-Z$^1$;

wherein:
L$^1$ is $C_{1-10}$ alkylene, $C_{1-10}$ heteroalkylene, $C_{2-10}$ alkenylene, $C_{2-10}$ alkynylene, $C_{3-15}$ cycloalkylene, $C_{1-10}$ heteroalkylene-$C_{3-15}$ cycloalkylene, $C_{6-20}$ arylene, $C_{7-20}$ aralkylene, heteroarylene, or heterocyclylene;

Z$^1$ is (a) amino, azido, chloro, bromo, iodo, or thiol; (b) N-maleimido, N-3,4-dibromo-maleimido, $C_{2-6}$ alkynyl, heterocyclyl containing a carbon-carbon triple, acrylyl, 3-sulfo-N-succinimidyloxycarbonyl, tetrafluorophenoxycarbonyl, pentofluorophenoxycarbonyl, $C_{2-6}$ alkynyloxy, $C_{3-15}$ cycloalkyloxy containing a carbon-carbon triple, $C_{6-20}$ aryloxy containing a carbon-carbon triple, or heterocyclyloxy containing a carbon-carbon triple; (c) —OP(O$R^{1a}$)(N$R^{1b}R^{1c}$), OP((N$R^{1b}R^{1c}$)$_2$, —OS(O)$_2R^{1a}$, or —S—S$R^{1a}$; or (d) Z$^6$; and p is an integer of 1 to 50;

$R^2$, $R^3$, $R^4$, $R^5$, $R^7$, $R^8$, $R^9$, and $R^{10}$ are each independently (a) hydrogen, deuterium, azido, cyano, halo, nitro, sulfo, —OPO$_3$H$_2$, or —PO$_3$H$_2$; (b) $C_{1-10}$alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O) N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C (O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$ N$R^{1b}R^{1c}$, —S$R^{1a}$, —S$R^{1a}$, —S(O)$R^{1a}$, —S(O)$_2R^{1a}$, —S(O) N$R^{1b}R^{1c}$, or —S(O)$_2$N$R^{1b}R^{1c}$; (d) $R^2$ and $R^3$, $R^4$ and $R^5$, $R^7$ and $R^8$, or $R^9$ and $R^{10}$, each pair together with the carbon atoms to which they are attached independently form $C_{3-15}$ cycloalkyl, $C_{6-20}$ aryl, heteroaryl, or heterocyclyl; (e) $R^3$ and $R^4$, or $R^8$ and $R^9$, each pair together with the carbon atoms to which they are attached independently form $C_{3-15}$ cycloalkyl, $C_{6-20}$ aryl, heteroaryl, or heterocyclyl; or (f) —O(CH$_2$CH$_2$O)$_r$-L$^r$-Z$^r$, with the proviso that when $R^1$ is not —(CH$_2$CH$_2$O)$_p$-L$^1$-Z$^1$, at least one of $R^1$, $R^2$, $R^3$, $R^4$, $R^5$, $R^7$, $R^8$, $R^9$, and $R^{10}$ is —O(CH$_2$CH$_2$O)$_r$-L$^r$-Z$^r$;

wherein:
L$^r$ is $C_{1-10}$ alkylene, $C_{1-10}$ heteroalkylene, $C_{2-10}$ alkenylene, $C_{2-10}$ alkynylene, $C_{3-15}$ cycloalkylene, $C_{1-10}$ heteroalkylene-$C_{3-15}$ cycloalkylene, $C_{6-20}$ arylene, $C_{7-20}$ aralkylene, heteroarylene, or heterocyclylene;

Z$^r$ is (a) hydrogen, deuterium, halo, cyano, nitro, sulfo, —OPO$_3$H$_2$, or —PO$_3$H$_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O) N$R^{1b}R^{1c}$, —N$R^{1a}$C(=N$R^{1d}$)N$R^{1b}R^{1c}$, —N$R^{1a}$S(O) $R^{1d}$, —N$R^{1a}$S(O)$_2R^{1d}$, —N$R^{1a}$S(O)N$R^{1b}$R6$^{1c}$, —N$R^{1a}$S(O)$_2$N$R^{1b}R^{1c}$, —S$R^{1a}$, —S(O)$R^{1a}$, —S(O)$_2$ $R^{1a}$, —S(O)N$R^{1b}R^{1c}$, or —S(O)$_2$N$R^{1b}R^{1c}$; or (d) Z$^1$; and r is an integer of 1 to 50;

$R^6$ is (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O) O$R^{1a}$, —C(O)N$R^{1b}R^{1c}$, —C(N$R^{1a}$)N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; or (d) —(CH$_2$CH$_2$O)$_q$-L$^6$-Z$^6$;

wherein:
L$^6$ is $C_{1-10}$ alkylene, $C_{1-10}$ heteroalkylene, $C_{2-10}$ alkenylene, $C_{2-10}$ alkynylene, $C_{3-15}$ cycloalkylene, $C_{6-20}$ arylene, $C_{7-20}$ aralkylene, heteroarylene, or heterocyclylene;

Z$^6$ is (a) hydrogen, deuterium, halo, cyano, nitro, sulfo, —OPO$_3$H$_2$, or —PO$_3$H$_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O) N$R^{1b}R^{1c}$, —OC(=0N$R^{1a}$)N$R^{1b}R^{1c}$, —OS(O)$R^{1a}$, —IS (O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)Or$^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O) N$R^{1b}R^{1c}$, —N$R^{1a\ S(O)}_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or (d) Z$^1$; and q is an integer of 1 to 50; and each $R^{1a}$, $R^{1b}$, $R^{1c}$, and $R^{1d}$ is independently (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) $R^{1a}$ and $R^{1c}$ together with the C and N atoms to which they are attached form heterocyclyl; or (d) $R^{1b}$ and $R^{1c}$ together with the N atom to which they are attached form heteroaryl or heterocyclyl;

wherein each alkyl, alkylene, heteroalkylene, alkenyl, alkenylene, alkynyl, alkynylene, cycloalkyl, cycloalkylene, aryl, arylene, aralkyl, aralkylene, heteroaryl, heteroarylene, heterocyclyl, heterocyclylene, alkynyloxy, cycloalkyloxy, aryloxy, and heterocyclyloxy is optionally substituted with one or more substituents Q, where each Q is independently selected from (a) deuterium, azido, cyano, halo, nitro, oxo, sulfo, —OPO$_3$H$_2$, and —PO$_3$H$_2$; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q$^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —CO (=N$R^a$)N$R^bR^c$, —OS(O)$R^a$, —OS(O)$_2R^a$, —OS(O) N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$) N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O) N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents Q$^a$; or (iii) $R^b$ and $R^c$ together with the N atom to which they are attached form heteroaryl or heterocyclyl, each of which is further optionally substituted with one or more, in one embodiment, one, two, three, or four, substituents Q$^a$;

wherein each $Q^a$ is independently selected from the group consisting of (a) deuterium, azido, cyano, halo, nitro, oxo, sulfo, —OPO$_3$H$_2$, and —PO$_3$H$_2$; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —C(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

Also provided herein is a compound of Formula I:

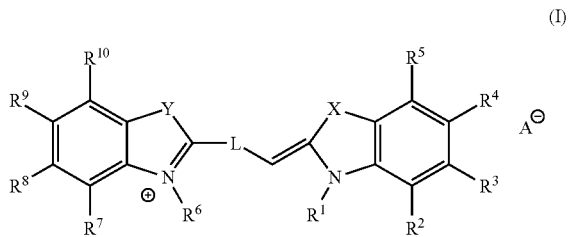

(I)

or a tautomer or a mixture of two or more tautomers thereof; or a pharmaceutically acceptable solvate, or hydrate thereof; wherein:

A is an anion bearing a negative charge;
L is

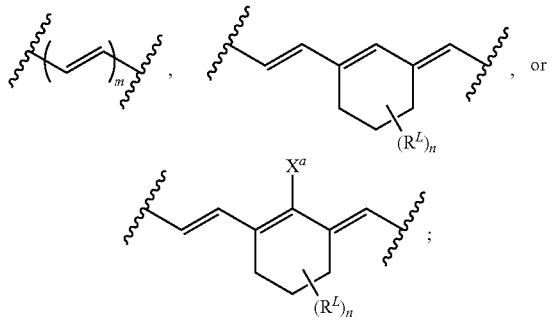

wherein:
each $R^L$ is independently (a) hydrogen, deuterium, azido, cyano, halo, nitro, oxo, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; or (c) —C(O)R$^{1a}$, —C(O)OR$^{1a}$, —C(O)NR$_{1b}$R$^{1c}$, (NR$^{1a}$)NR$^{1b}$R$^{1c}$, —OR$^{1a}$, —OC(O)R$^{1a}$, —OC(O)OR$^{1a}$, —OC(O)NR$_{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{2d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{a1}$, —S(O)NR$^{1b}$R$^{1c}$, or —S(O)$_2$NR$^{1b}$R$^{1c}$;

$X^a$ is (a) hydrogen, deuterium, azido, cyano, halo, nitro, oxo, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; (c) —C(R$^{1a}$R$^{1b}$), —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR6$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_{NR}$$^{1b}$R$^{1c}$—SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; (d) —(CH$_2$CH$_2$O)$_p$-L$^1$-Z$^1$, —(CH$_2$CH$_2$O)$_p$—COOH, 13 (CH$_2$CH$_2$O)$_p$—N$_3$, —(CH$_2$CH$_2$O)$_p$—OH, —(CH$_2$CH$_2$O)$_p$-alkyne, —(CH$_2$CH$_2$O)$_p$-bionn, —(CH$_2$CH$_2$O)$_p$-NHS ester, —(CH$_2$CH$_2$O)$_p$-amine, —(CH$_2$CH$_2$O)$_p$-DBCO, —(CH$_2$CH$_2$O)$_p$-Fmoc, —(CH$_2$CH$_2$O)$_p$-aldehyde, —(CH$_2$CH$_2$O)$_p$-phosphonate, —(CH$_2$CH$_2$O)$_p$-tosylate, —(CH$_2$CH$_2$O)$_p$-FPF ester, —(CH$_2$CH$_2$O)$_p$-Boc, —(CH$_2$CH$_2$O)$_p$-aminooxy, —(CH$_2$CH$_2$O)$_p$-bromo, —(CH$_2$CH$_2$O)$_p$-mal, or —(CH$_2$CH$_2$O)$_p$-propargyl; or (e) carboxycylic acid, amine, azide, DBCO, hydrazide, maleimide, NHS ester, TCO, tetrazine, or biotin;

m is an integer of 1, 2, or 3; and
n is an integer of 0, 1, 2, 3, 4, 5, 6, or 7;
X and Y are each independently C(R$^{Xa}$R$^{Xb}$), O, S, or NR$^{Xc}$;

wherein:
R$^{Xa}$ and R$^{Xb}$ are each independently (a) hydrogen or deuterium; or (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; and R$^{Xc}$ is (a) hydrogen or deuterium; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; or (c) —C(O)R$^{1a}$, —C(O)OR$^{1a}$, —C(O)NR$^{1b}$R$^{1c}$, —C(NR$^a$)NR$^{1b}$R$^{1c}$, —S(O)R$^{1a}$, —S(O)$_2$R$^{1a}$, —S(O)NR$^{1b}$R$^{1c}$, or S(O)$_2$NR$^{1b}$R$^{1c}$;

R$^1$ is —(CH$_2$CH$_2$O)$_p$-L$^1$-Z$^1$,
wherein:
L$^1$ is C$_{1-10}$ alkylene, C$_{1-10}$ heteroalkylene, C$_{2-10}$ alkenylene, C$_{2-10}$ alkynylene, C$_{3-15}$ cycloalkylene, C$_{1-10}$ heteroalkylene-C$_{3-15}$ cycloalkylene, C$_{6-20}$ arylene, C$_{7-20}$ aralkylene, heteroarylene, or heterocyclylene;

Z$^1$ is (a) amino, azido, chloro, bromo, iodo, or thiol; (b) N-maleimido, N-3,4-dibromo-maleimido, C$_{2-6}$ alkynyl, heterocyclyl containing a carbon-carbon triple, acrylyl, 3-sulfo-N-succinimidyloxycarbonyl, tetrafluorophenoxycarbonyl, pentofluorophenoxycarbonyl, C$_{2-6}$ alkynyloxy, C$_{3-15}$ cycloalkyloxy containing a carbon-carbon triple, C$_{6-20}$ aryloxy containing a carbon-carbon triple, or heterocyclyloxy containing a carbon-carbon triple; (c) —OP(OR$^{1a}$)(NR$^{1b}$R$^{1c}$),—OP((NR$^{1b}$R$^{1c}$)$_2$, —OS(O)$_2$R$^{1a}$, or —S—SR$^{1a}$; or (d) Z$^6$; and p is an integer of 1 to 50;
R$^2$, R$^3$, R$^4$, R$^5$, R$^7$, R$^8$, R$^9$, and R$^{10}$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) —C(O)R$^{1a}$, —C(O)OR$^{1a}$, —C(O)NR$^{1b}$R$^{1c}$, (NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$NR$^{1b}$R$^{1c}$, —OS(O)R$^{1a}$, —OS(O)$_2$R$^{1a}$, —OS(O)NR$^{1b}$R$^{1c}$, —OS (O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; (d) R$^2$ and R$^3$, R$^4$ and R$^5$, R$^7$ and R$^8$, or R$^9$ and R$^{10}$, each pair together with the carbon atoms to which they are attached independently form C$_{3-15}$ cycloalkyl, C$_{6-20}$ aryl, heteroaryl, or heterocyclyl; or (e) R$^3$ and R$^4$, or R$^8$ and R$^9$, each pair together with the carbon atoms to which they are attached independently form C$_{3-15}$ cycloalkyl, C$_{6-20}$ aryl, heteroaryl, or heterocyclyl;

R$^6$ is (a) hydrogen or deuterium; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$)NR$^{1b}$R$^{1c}$, —S(O)R$^{1a}$, —S(O)$_2$R$^{1a}$—S(O)NR$^{1b}$R$^{1c}$or —S(O)$_2$NR$^{1b}$R$^{1c}$; or (d) —(CH$_2$CH$_2$O)$_q$-L$^6$-Z$^6$;

wherein:

L$^6$ is C$_{1-10}$ alkylene, C$_{1-10}$ heteroalkylene, C$_{2-10}$ alkenylene, C$_{2-10}$ alkynylene, C$_{3-15}$ cycloalkylene, C$_{6-20}$ arylene, C$_{7-20}$ aralkylene, heteroarylene, or heterocyclylene;

Z$^6$ is (a) hydrogen, deuterium, halo, cyano, nitro, sulfo, —OPO$_2$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$_{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or (d) z$^1$; and q is an integer of 1 to 50; and each R$^{1a}$, R$^{1c}$, and R$^{1d}$ is independently (a) hydrogen or deuterium; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) R$^{1a}$ and R$^{1c}$ together with the C and N atoms to which they are attached form heterocyclyl; or (d) R$^{1b}$ and R$^{1c}$ together with the N atom to which they are attached form heteroaryl or heterocyclyl;

wherein each alkyl, alkylene, heteroalkylene, alkenyl, alkenylene, alkynyl, alkynylene, cycloalkyl, cycloalkylene, aryl, arylene, aralkyl, aralkylene, heteroaryl, heteroarylene, heterocyclyl, heterocyclylene, alkynyloxy, cycloalkyloxy, aryloxy, and heterocyclyloxy is optionally substituted with one or more substituents Q, where each Q is independently selected from (a) deuterium, azido, cyano, halo, nitro, oxo, sulfo, —OPO$_3$H$_2$, and —PO$_3$H$_2$; (b) C$_{1-6}$alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each of which is further optionally substituted with one or more, in one embodiment, one, two, three, or four, substituents Q$^a$; or (iii) R$^b$ and R$^c$ together with the N atom to which they are attached form heteroaryl or heterocyclyl, each of which is further optionally substituted with one or more, in one embodiment, one, two, three, or four, substituents Q$^a$;

wherein each Q$^a$ is independently selected from the group consisting of (a) deuterium, azido, cyano, halo, nitro, oxo, sulfo, —OPO$_3$H$_2$, and —PO$_3$H$_2$; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)R$^e$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

Additionally provided herein is a pharmaceutical composition comprising a compound disclosed herein, e.g., a compound of Formula I, or a tautomer or a mixture of two or more tautomers thereof; or a pharmaceutically acceptable solvate or hydrate thereof; and a pharmaceutically acceptable excipient.

Furthermore, provided herein is a method of labeling a biomolecule, comprising the step of contacting the biomolecule with a compound disclosed herein, e.g., a compound of Formula I, or a tautomer or a mixture of two or more tautomers thereof; or a pharmaceutically acceptable solvate or hydrate thereof.

DETAILED DESCRIPTION

To facilitate understanding of the disclosure set forth herein, a number of terms are defined below.

Generally, the nomenclature used herein and the laboratory procedures in biochemistry, biology, organic chemistry, medicinal chemistry, pharmaceutical chemistry, pharmacology, and others described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science*

*and Practice of Pharmacy*, 22nd ed.; Allen et al., Eds.; The Pharmaceutical Press, 2012; *Handbook of Pharmaceutical Excipients*, 7th ed.; Rowe et al., Eds.; The Pharmaceutical Press: 2012; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "alkyl" refers to a linear or branched saturated monovalent hydrocarbon radical, wherein the alkyl may optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkylene" refers to a linear or branched saturated divalent hydrocarbon radical, wherein the alkylene may optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene (—$CH_2$—), ethylene (—$CH_2CH_2$—), propylene (including all isomeric forms), n-propylene (—$CH_2CH_2CH_2$—), isopropylene, butylene (including all isomeric forms), n-butylene (—$CH_2CH_2CH_2CH_2$—), isobutylene, t-butylene, pentylene (including all isomeric forms), and hexylene (including all isomeric forms).

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —$CH_2O$—, —$CH_2OCH_2$—, —$(CH_2)_2O$—, —$(CH_2)_2OCH_2$—, —$CH_2NH$—, —$CH_2NHCH_2$—, —$(CH_2)_2NH$—, —$(CH_2)_2NHC(O)$—, —$(CH_2)_2NHC(O)CH_2$—, —$(CH_2)_2NHC(O)(CH_2)_2$—, —$(CH_2)_2NHC(O)(CH_2)_3$—, —$(CH_2)_2NHC(O)(CH_2)_5$—, —$(CH_2)_6NHC(O)(CH_2)_2$—, —$(CH_2)_2NHC(O)(CH_2)_2C(O)$—, —$(CH_2)_2NHC(O)(CH_2)_4C(O)$—, —$(CH_2)_2C(O)NH(CH_2)_2C(O)$—, —$(CH_2)_2C(O)NH(CH_2)_4C(O)$—, —$(CH_2)_2NHC(O)CH(SO_3H)CH_2NHC(O)(CH_2)_2C(O)$—, —$(CH_2)_2C(O)NH(CH_2)_3$—, —$(CH_2)_2C(O)NH(CH_2)_4CH_2$—, —$CH_2S$—, —$CH_2CH_2$—, and —$CH_2CH_2S$—. In certain embodiments, heteroalkylene may also be optionally substituted with one or more substituents Q as described herein.

The term "alkenyl" refers to a linear or branched monovalent hydrocarbon radical, which contains one or more carbon-carbon double bond(s), in one embodiment, one to five carbon-carbon double bond(s), in another embodiment, one carbon-carbon double bond. The alkenyl may be optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more carbon-carbon double bond(s), in one embodiment, one to five carbon-carbon double bond(s), in another embodiment, one carbon-carbon double bond. The alkenylene may be optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "alkynyl" refers to a linear or branched monovalent hydrocarbon radical, which contains one or more carbon-carbon triple bond(s), in one embodiment, one to five carbon-carbon triple bond(s), in another embodiment, one carbon-carbon triple bond. The alkynyl may be optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{3-20}$), 4 to 15 ($C_{3-15}$), 4 to 10 ($C_{3-10}$), or 4 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "alkynylene" refers to a linear or branched divalent hydrocarbon radical, which contains one or more carbon-carbon triple bond(s), in one embodiment, one to five carbon-carbon triple bond(s), in another embodiment, one carbon-carbon triple bond. The alkynylene may be optionally substituted with one or more substituents Q as described herein. For example, $C_{2-6}$ alkynylene refers to a linear unsaturated divalent hydrocarbon radical of 2 to 6 carbon atoms or a branched unsaturated divalent hydrocarbon radical of 4 to 6 carbon atoms. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 4 to 20 ($C_{3-20}$), 4 to 15 ($C_{3-15}$), 4 to 10 ($C_{3-10}$), or 4 to 6 ($C_{3-6}$) carbon atoms. Examples of alkynylene groups include, but are not limited to, ethynylene (—C≡C—), propynylene (including all isomeric forms, e.g., 1,3-propynylene (—C≡CCH$_2$—)), butynylene (including all isomeric forms, e.g., 1-butyn-1,4-ylene), pentynylene (including all isomeric forms, e.g., 1-pentyn-1,5-ylene), and hexynylene (including all isomeric forms, e.g., 1-hexyn-1,6-ylene).

The term "cycloalkyl" refers to a cyclic monovalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "cycloalkylene" refers to a cyclic divalent hydrocarbon radical, which may be optionally substituted with one or more substituents Q as described herein. In one embodiment, cycloalkylene groups may be saturated or unsaturated but non-aromatic, and/or bridged, and/or non-bridged, and/or fused bicyclic groups. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene, cyclobutylene, cyclopentylene, cyclopentenylene, cyclohexylene, cyclohexenylene, cyclohexadienylene, cycloheptylene, cycloheptenylene, bicyclo[2.1.1]hexylene, bicyclo[2.2.1]heptylene, decalinylene, and adamantylene.

The term "aryl" refers to a monovalent monocyclic aromatic group and/or monovalent polycyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein.

The term "arylene" refers to a divalent monocyclic aromatic hydrocarbon radical or divalent polycyclic aromatic hydrocarbon radical that contains at least one aromatic hydrocarbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydronaphthylene (tetralinylene). In certain embodiments, arylene may be optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, aralkyl are optionally substituted with one or more substituents Q as described herein.

The term "aralkylene" or "arylalkylene" refers to a divalent alkylene group substituted with one or more aryl groups. In certain embodiments, the aralkylene has from 7 to 30 ($C_{7-30}$), from 7 to 20 ($C_{7-20}$), or from 7 to 16 ($C_{7-16}$) carbon atoms. Examples of aralkylene groups include, but are not limited to, benzylene, 2-phenylethylene, and 3-phenylpropylene. In certain embodiments, aralkylene are optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, and N in the ring. Heteroaryl groups are bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted with one or more substituents Q as described herein.

The term "heteroarylene" refers to a divalent monocyclic aromatic group or divalent polycyclic aromatic group that contains at least one aromatic ring, wherein at least one aromatic ring contains one or more heteroatoms in the ring, each of which is independently selected from O, S, and N. A heteroarylene group has at least one linkage to the rest of a molecule via its aromatic ring(s). Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroarylene may also be optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. Heterocyclylene groups are bonded to the rest of a molecule through the non-aromatic ring. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, heterocyclic may also be optionally substituted with one or more substituents Q as described herein.

The term "halogen", "halide" or "halo" refers to fluorine, chlorine, bromine, and/or iodine.

The term "optionally substituted" is intended to mean that a group or substituent, such as an alkyl, alkylene, heteroalkylene, alkenyl, alkenylene, alkynyl, cycloalkyl, cycloalkylene, aryl, arylene, aralkyl, aralkylene, heteroaryl, heteroarylene, heterocyclyl, or heterocyclylene group, may be substituted with one or more substituents Q, each of which is independently selected from, e.g., (a) deuterium, azido (—N$_3$), cyano (—CN), halo, nitro (NO$_2$), oxo (=O), sulfo (—SO$_3$H), —PO$_3$H$_2$, and —OPO$_3$H$_2$, (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O) R$^d$, —NR$^a$C(O)OR$^d$, —NR$^a$C(O)NR$^b$R$^c$, —NR$^a$C(=NR$^d$) NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —SR$^a$, —S(O)R$^a$, —S(O)$_2$R$^a$, —S(O)NR$^b$R$^c$, and —S(O)$_2$NR$^b$R$^c$; wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each of which is further optionally substituted with one or more, in one embodiment, one, two, three, or four, substituents Q$^a$; or (iii) R$^b$ and R$^c$ together with the N atom to which they are attached form heteroaryl or heterocyclyl, each of which is further optionally substituted with one or more, in one embodiment, one, two, three, or four, substituents Q$^a$. As used herein, all groups that can be substituted are "optionally substituted," unless otherwise specified.

In one embodiment, each Q$^a$ is independently selected from the group consisting of (a) deuterium, azido, halo, cyano, nitro, oxo, sulfo, —OPO$_3$H$_2$, and —PO$_3$H$_2$; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O) R$^e$, —C(O)OR$^e$, —C(O)NR$^f$R$^g$, —C(NR$^e$)NR$^f$R$^g$, —OC$^e$, —OC(O)R$^e$, —OC(O)OR$^e$, —OC(O)NR$^f$R$^g$, —OC(=NR$^e$) NR$^f$R$^g$, —OS(O)R$^e$, —OS(O)$_2$R$^e$, —OS(O)NR$^f$R$^g$, —OS (O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —BR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$_g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), mass spectrometry (MS), and elemental analysis; or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single tautomer or a mixture of tautomers, as determined by standard analytical methods.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

As used herein, the abbreviations for any protective groups, amino acids and other compounds, are, unless indicated otherwise, in accord with their common usage or recognized abbreviations including abbreviations found in *J. Org. Chem.* 2007, 72, 23A-24A or abbreviations established by the IUPAC-IUB Commission on Biochemical Nomenclature (*Biochem.* 1972, 11, 942-944).

Compounds

In one embodiment, provided herein is a compound of Formula I:

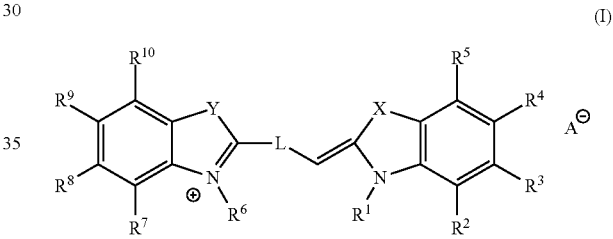

or a tautomer or a mixture of two or more tautomers thereof; or a pharmaceutically acceptable solvate, or hydrate thereof; wherein:

A is an anion bearing a negative charge;

L is

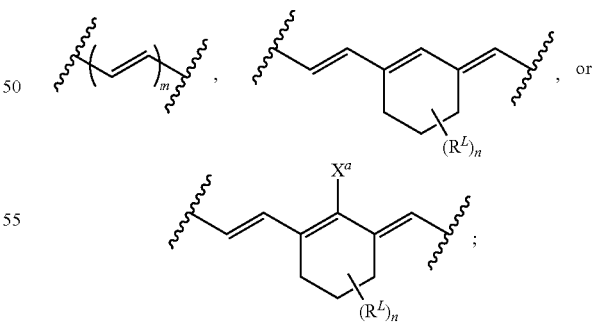

wherein:

each R$^L$ is independently (a) hydrogen, deuterium, azido, cyano, halo, nitro, oxo, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; or (c) —C(O)R$^{1a}$, —C(O)OR$^{1a}$, —C(O) NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$ —S(O)NR$^{1b}$R$^{1c}$, or —S(O)$_2$NR$^{1b}$R$^{1c}$;

X$^a$ is (a) hydrogen, deuterium, azido, cyano, halo, nitro, oxo, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl , each of which is optionally substituted with one or more substituents Q; (c) —C(R$^{1a}$R$^{1b}$), —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$MR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_{NR}$$^{1b}$R$^{1c}$;(d) —(CH$_2$CH$_2$O)$_p$-L$^1$-Z$^1$, —(CH$_2$CH$_2$O)$_p$-COOH, —(CH$_2$CH$_2$O)$_p$-N$_3$, —(CH$_2$CH$_2$O)$_p$-OH, —(CH$_2$CH$_2$O)$_p$-alkyne, —(CH$_2$CH$_2$O)$_p$-biotin, —(CH$_2$CH$_2$O)$_p$-NHS ester, —(CH$_2$CH$_2$O)$_p$-amine, —(CH$_2$CH$_2$O)$_p$-DBCO, —(CH$_2$CH$_2$O)$_p$-Fmoc, —(CH$_2$CH$_2$O)$_p$-aldehyde, —(CH$_2$CH$_2$O)$_p$-phosphonate, —(CH$_2$CH$_2$O)$_p$-tosylate, —(CH$_2$CH$_2$O)$_p$-FPF ester, —(CH$_2$CH$_2$O)$_p$-Boc, —(CH$_2$CH$_2$O)$_p$-aminooxy, —(CH$_2$CH$_2$O)$_p$-bromo, —(CH$_2$CH$_2$O)$_p$-mal, or —(CH$_2$CH$_2$O)$_p$-propargyl; or (e) carboxycylic acid, amine, azide, DBCO, hydrazide, maleimide, NHS ester, TCO, tetrazine, or biotin;

m is an integer of 1, 2, or 3; and n is an integer of 0, 1, 2, 3, 4, 5, 6, or 7;

X and Y are each independently C(R$^{Xa}$R$^{Xb}$), O, S, or NR$^{Xc}$;

wherein:

R$^{Xa}$ and R$^{Xb}$ are each independently (a) hydrogen or deuterium; or (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; and R$^{Xc}$ is (a) hydrogen or deuterium; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —S(O)R$_{1a}$, —S(O)$_2$R$^{1a}$, —S(O)NR$^{1b}$R$^{1c}$, or —S(O)$_2$NR$^{1b}$R$^{1c}$;

R$^1$ is (a) hydrogen or deuterium; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; or (d) —(CH$_2$CH$_2$O)$_p$-L$^1$-Z$^1$;

wherein:

L$^1$ is C$_{1-10}$ alkylene, C$_{1-10}$ heteroalkylene, C$_{2-10}$ alkenylene, C$_{2-10}$ alkynylene, C$_{3-15}$ cycloalkylene, C$_{1-10}$ beteroalkylene-C$_{3-15}$ cycloalkylene, C$_{6-20}$ arylene, C$_{7-20}$ aralkylene, heteroarylene, or heterocyclylene;

Z$^1$ is (a) amino, azido, chloro, bromo, iodo, or thiol; (b) N-maleimido, N-3,4-dibromo-maleimido, C$_{2-6}$ alkynyl, heterocyclyl containing a carbon-carbon triple, acrylyl, 3-sulfo-N-succinimidyloxycarbonyl, tetrafluorophenoxycarbonyl, pentofluorophenoxycarbonyl, C$_{2-6}$ alkynyloxy, C$_{3-15}$ cycloalkyloxy containing a carbon-carbon triple, C$_{6-20}$ aryloxy containing a carbon-carbon triple, or heterocyclyloxy containing a carbon-carbon triple; (c) —OP(OR$^{1a}$)(NR$^{1b}$R$^{1a}$), —OP((NR$^{1b}$R$^{1c}$)$_2$, —OS(O)$_2$R$^{1a}$, or —S—SR$^{1a}$; or (d) Z$^6$; and p is an integer of 1 to 50;

R$^2$, R$^3$, R$^4$, R$^5$, R$^7$, R$^8$, R$^9$, and R$^{10}$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) —C(O)R$^{1a}$, —C(O)OR$^{1a}$, —C(O)NR$^{1b}$R$^{1c}$, —C(N$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^1$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; (d) R$^2$ and R$^3$, R$^4$ and R$^5$, R$^7$ and R$^8$, or R$^9$ and R$^{10}$, each pair together with the carbon atoms to which they are attached independently form C$_{3-15}$ cycloalkyl, C$_{6-20}$ aryl, heteroaryl, or heterocyclyl; (e) R$^3$ and R$^4$, or R$^8$ and R$^9$, each pair together with the carbon atoms to which they are attached independently form C$_{3-15}$ cycloalkyl, C$_{6-20}$ aryl, heteroaryl, or heterocyclyl; or (f) —O(CH$_2$CH$_2$O)$_r$-L$^r$-Z$^r$, with the proviso that when R$^1$ is not —(CH$_2$CH$_2$O)$_p$-L$^1$-Z$^1$, at least one of R$^1$, R$^2$, R$^3$, R$^4$, R$^5$, R$^7$, R$^8$, R$^9$, and R$^{10}$, is —O(CH$_2$CH$_2$O)$_r$-L$^r$-Z$^r$;

wherein:

L$^r$ is C$_{1-10}$ alkylene, C$_{1-10}$ heteroalkylene, C$_{2-10}$ alkenylene, C$_{2-10}$ alkynylene, C$_{3-15}$ cycloalkylene, C$_{1-10}$ heteroalkylene-C$_{3-15}$ cycloalkylene, C$_{6-20}$ arylene, C$_{7-20}$ aralkylene, heteroarylene, or heterocyclylene;

Z$^r$ is (a) hydrogen, deuterium, halo, cyano, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or (d) Z$^1$; and r is an integer of 1 to 50;

R$^6$ is (a) hydrogen or deuterium; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$)NR$^{1b}$R$^{1c}$, —S(O)R$^{1a}$, —S(O)$_2$R$^{1a}$, —S(O)$_2$R$^{1a}$, —S(O)NR$^{1b}$R$^{1c}$or —S(O)$_2$NR$^{1b}$R$^{1c}$; or (d) —(CH$_2$CH$_2$O)$_q$-L$^6$-Z$^6$;

wherein:

L$^6$ is C$_{1-10}$ alkylene, C$_{1-10}$ heteroalkylene, C$_{2-10}$ alkenylene, C$_{2-10}$ alkynylene, C$_{3-15}$ cycloalkylene, C$_{6-20}$ arylene, C$_{7-20}$ aralkylene, heteroarylene, or heterocyclylene;

Z$^6$ is (a) hydrogen, deuterium, halo, cyano, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$_{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or (d) Z$^1$; and q is an integer of 1 to 50; and each R$^{1a}$, is independently (a) hydrogen or deuterium; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; (c) R$^{1a}$ and R$^{1c}$ together with the C and N atoms to which they are attached form heterocyclyl; or (d) R$^{1b}$ and R$^{1c}$ together with the N atom to which they are attached form heteroaryl or heterocyclyl;

wherein each alkyl, alkylene, heteroalkylene, alkenyl, alkenylene, alkynyl, alkynylene, cycloalkyl, cycloalkylene, aryl, arylene, aralkyl, aralkylene, heteroaryl, heteroarylene, heterocyclyl, heterocyclylene, alkynyloxy, cycloalkyloxy, aryloxy, and heterocyclyloxy is optionally substituted with one or more substituents Q, where each Q is independently selected from (a) deuterium, azido, cyano, halo, nitro, oxo, sulfo, —OPO$_3$H$_2$, and —PO$_3$H$_2$; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each of which is further optionally substituted with one or more, in one embodiment, one, two, three, or four, substituents Q$^a$; or (iii) R$^b$ and R$^c$ together with the N atom to which they are attached form heteroaryl or heterocyclyl, each of which is further optionally substituted with one or more, in one embodiment, one, two, three, or four, substituents Q$^a$;

wherein each Q$^a$ is independently selected from the group consisting of (a) deuterium, azido, cyano, halo, nitro, oxo, sulfo, —OPO$_3$H$_2$, and —PO$_3$H$_2$; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$^{7-15}$ aralkyl, heteroaryl, or heterocyclyl; or (iii) R$^f$ and R$^g$ together with the N atom to which they are attached form heteroaryl or heterocyclyl.

In another embodiment, provided herein is a compound of Formula I:

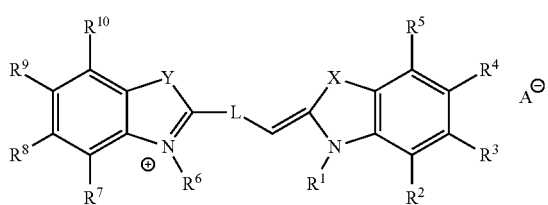

(I)

or a tautomer or a mixture of two or more tautomers thereof; or a pharmaceutically acceptable solvate or hydrate thereof;

wherein:

A is an anion bearing a negative charge;

L is

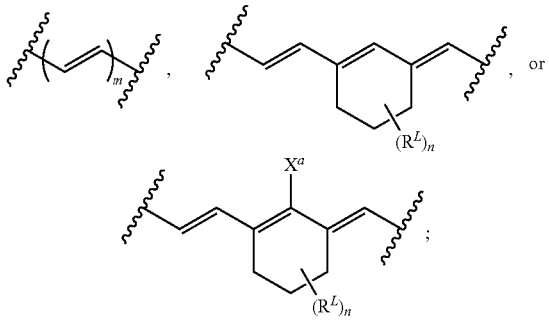

wherein:

each R$^L$ is independently (a) hydrogen, deuterium, azido, cyano, halo, nitro, oxo, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

X$^a$ is (a) hydrogen deuterium, azido, cyano, halo, nitro, oxo, sulfo, —OPO$_3$H$_2$, or —PO$_3$H$^2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; (c) —C(R$^{1a}$ R$^{1b}$), —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; (d) —(CH$_2$CH$_2$O)$_p$-L$^1$-Z$^1$, —(CH$_2$CH$_2$O)$_p$—COOH, —(CH$_2$CH$_2$O)$_p$, —N$_3$, —(CH$_2$CH$_2$O)$_p$—OH, —(CH$_2$CH$_2$O)$_p$-alkyne, —(CH$_2$CH$_2$O)$_p$-biotin, —(CH$_2$CH$_2$O)$_p$-NHS ester, —(CH$_2$CH$_2$O)$_p$-amine, —(CH$_2$CH$_2$O)$_p$-DBCO, —(CH$_2$CH$_2$O)$_p$-Fmoc, —(CH$_2$CH$_2$O)$_p$-aldehyde, —(CH$_2$CH$_2$O)$_p$-phosphonate, —(CH$_2$CH$_2$O)$_p$-tosylate, —(CH$_2$CH$_2$O)$_p$-FPF ester, —(CH$_2$CH$_2$O)$_p$-Boc, -(CH$_2$CH$_2$O)$_p$-aminooxy, —(CH$_2$CH$_2$O)$_p$-bromo, —(CH$_2$CH$_2$O)$_p$-mal, or —(CH$_2$CH$_2$O)$_p$-propargyl; or (e) carboxycylic acid, amine, azide, DBCO, hydrazide, maleimide, NHS ester, TCO, tetrazine, or biotin;

m is an integer of 1, 2, or 3; and n is an integer of 0, 1, 2, 3, 4, 5, 6, or 7;

X and Y are each independently $C(R^{Xa}R^{Xb})$, O, S, or $NR^{Xc}$;

wherein:

$R^{Xa}$ and $R^{Xb}$ are each independently (a) hydrogen or deuterium; or (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; and $R^{Xc}$ is (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; or (c) —C(O)$R^{1a}$, —C(O)O$R^{1a}$, —C(O)NR$_{1b}$R$_{1c}$, —C(NR$^{1a}$)NR$^{1b}$R$^{1c}$, —S(O)$R^{1a}$, —S(O)$_2$R$^{1a}$, —S(O)NR$^{1b}$R$^{1c}$, or —S(O)$_2$NR$^{1b}$R$^{1c}$;

$R^1$ is —(CH$_2$CH$_2$O)$_p$-L$^1$-Z$^1$, wherein:

L$^1$ is $C_{1-10}$ alkylene, $C_{1-10}$ heteroalkylene, $C_{2-10}$ alkenylene, $C_{2-10}$ alkynylene, $C_{3-15}$ cycloalkylene, $C_{1-10}$ heteroalkylene-$C_{3-15}$ cycloalkylene, $C_{6-20}$ arylene, $C_{7-20}$ aralkylene, heteroarylene, or heterocyclylene;

Z$^1$ is (a) amino, azido, chloro, bromo, iodo, or thiol; (b) N-maleimido, N-3,4-dibromo-maleimido, $C_{2-6}$ alkynyl, heterocyclyl containing a carbon-carbon triple, acrylyl, 3-sulfo-N-succinimidyloxycarbonyl, tetrafluorophenoxycarbonyl, pentofluorophenoxycarbonyl, $C_{2-6}$ alkynyloxy, $C_{3-15}$ cycloalkyloxy containing a carbon-carbon triple, $C_{6-20}$ aryloxy containing a carbon-carbon triple, or heterocyclyloxy containing a carbon-carbon triple; (c) —OP(OR$^{1a}$)(NR$^{1b}$R$^{1c}$)—OP((NR$^{1b}$R$^{1c}$)$_2$, —OS(O)$_2$R$^{1a}$, or —S—SR$^{1a}$; or (d) Z$^6$; and p is an integer of 1 to 50;

$R^2$, $R^3$, $R^4$, $R^5$, $R^7$, $R^8$, $R^9$, and $R^{10}$ are each independently (a) hydrogen, deuterium, azido, cyano, halo, nitro, sulfo, —OPO$_3$H$_2$, or —PO$_3$H$_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$)NR$^{1b}$R$^{1c}$—OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; (d) $R^2$ and $R^3$, $R^4$ and $R^4$ and $R^5$, $R^7$ and $R^8$, or $R^9$ and $R^{10}$, each pair together with the carbon atoms to which they are attached independently form $C_{3-15}$ cycloalkyl, $C_{6-20}$ aryl, heteroaryl, or heterocyclyl; or (e) $R^3$ and $R^4$, or $R^8$ and $R^9$, each pair together with the carbon atoms to which they are attached independently form $C_{3-15}$ cycloalkyl, $C_{6-20}$ aryl, heteroaryl, or heterocyclyl;

$R^6$ is (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$)NR$^{1b}$R$^{1c}$ —S(O)R$^{1a}$, —S(O)$_2$R$^{1a}$, —S(O)NR$^{1b}$R$^{1c}$ or —S(O)$_2$NR$^{1b}$R$^{1c}$; or (d) —(CH$_2$CH$_2$O)$_q$-L$^6$-Z$^6$;

wherein:

L$^6$ is $C_{1-10}$ alkylene, $C_{1-10}$ heteroalkylene, $C_{2-10}$ alkenylene, $C_{2-10}$ alkynylene, $C_{3-15}$ cycloalkylene, $C_{6-20}$ arylene, $C_{7-20}$ aralkylene, heteroarylene, or heterocyclylene;

Z$^6$ is (a) hydrogen, deuterium, halo, cyano, nitro, sulfo, —OPO$_3$H$_2$, or —PO$_3$H$_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OR(O)R$^{1a}$, —OC(O)OR$^{1a}$, —OC(O) NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or (d) Z$^1$; and q is an integer of 1 to 50; and each $R^{1a}$, K is independently (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) $R^{1a}$ and $R^{1c}$ together with the C and N atoms to which they are attached form heterocyclyl; or (d) $R^{1b}$ and $R^{1c}$ together with the N atom to which they are attached form heteroaryl or heterocyclyl;

wherein each alkyl, alkylene, heteroalkylene, alkenyl, alkenylene, alkynyl, alkynylene, cycloalkyl, cycloalkylene, aryl, arylene, aralkyl, aralkylene, heteroaryl, heteroarylene, heterocyclyl, heterocyclylene, alkynyloxy, cycloalkyloxy, aryloxy, and heterocyclyloxy is optionally substituted with one or more substituents Q, where each Q is independently selected from (a) deuterium, azido, cyano, halo, nitro, oxo, sulfo, —OPO$_3$H$_2$, and —PO$_3$H$_2$; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents Q$^a$; or (iii) R$^b$ and R$^c$ together with the N atom to which they are attached form heteroaryl or heterocyclyl, each of which is further optionally substituted with one or more, in one embodiment, one, two, three, or four, substituents Q$^a$;

wherein each Q$^a$ is independently selected from the group consisting of (a) deuterium, azido, cyano, halo, nitro, oxo, sulfo, —OPO$_3$H$_2$, and —PO$_3$H$_2$; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$, is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

In yet another embodiment, provided herein is a compound Formula II:

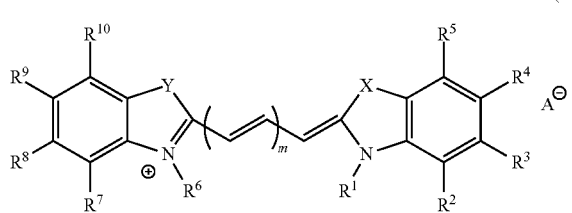

(II)

or a tautomer or a mixture of two or more tautomers thereof; or a pharmaceutically acceptable solvate or hydrate thereof; wherein $R^1$, $R^2$, $R^3$, $R^4$, $R^5$, $R^6$, $R^7$, $R^8$, $R^9$, $R^{10}$, A, X, Y, and m are , each as defined herein.

In one embodiment, in Formula I or II, $R^6$ is (a) hydrogen; (b) $C_{1-10}$ alkyl, optionally substituted with one or more substituents Q; or (c) —$(CH_2CH_2O)_q$-$L^6$-$Z^6$, where $L^6$, $Z^6$, and q are each as defined herein. In another embodiment, in Formula I or II, $R^6$ is $C_{1-10}$ alkyl, optionally substituted with one or more substituents Q. In yet another embodiment, in Formula I or II, $R^6$ is methyl or propyl, each of which is optionally substituted with one or more substituents Q. In yet another embodiment, in Formula I or II, $R^6$ is methyl or 3-hydroxypropyl. In still another embodiment, in Formula I or II, $R^6$ is $(CH_2CH_2O)_q$-$L^6$-$Z^6$, where $L^6$, $Z^6$, and q are each as defined herein.

In one embodiment, in Formula I or II, one of $R^2$, $R^3$, $R^4$, and $R^5$ is not hydrogen and the remaining three are each hydrogen. In another embodiment, in Formula I or II, $R^2$, $R^3$, $R^4$, and $R^5$ are each hydrogen. In yet another embodiment, in Formula I or II, one of $R^7$, $R^8$, $R^9$, and $R^{10}$ is not hydrogen and the remaining three are each hydrogen. In still another embodiment, in Formula I or II, $R^7$, $R^8$, $R^9$, and $R^{10}$ are each hydrogen.

In one embodiment, in Formula I or II, $R^1$ is —$(CH_2CH_2O)_p$$L^1$-$Z^1$, where $L^1$, $Z^1$, and p are each as defined herein. In another embodiment, in Formula I or II, $R^4$ is —$O(CH_2CH_2O)_r$-$L^r$-$Z^r$, where $L^r$, $Z^r$, and r are each as defined herein. In yet another embodiment, in in Formula I or II, $R^9$ is —$O(CH_2CH_2O)_r$-$L^r$$Z^r$, where $L^r$, $Z^r$, and r are each as defined herein.

In one embodiment, in Formula I or II, $R^1$ is —$(CH_2CH_2O)_p$-$L^1$-$Z^1$ and $R^4$ is —$O(CH_2CH_2O)_r$-$L^r$-$Z^r$, where $L^l$, $L^r$, $Z^l$, $Z^r$, p, and r are each as defined herein. In another embodiment, in Formula I or II, $R^1$ is —$(CH_2CH_2O)_p$-$L^1$-$Z^1$ and $R^9$ is —O $(CH_2CH_2O)_r$-$L^r$-$Z^r$, where $L^l$, $L^r$, $Z^1$, $Z^r$, p, and r are each as defined herein. In yet another embodiment, in Formula I or II, $R^4$ and $R^9$ are each independently —$O(CH_2CH_2O)_r$-$L^r$-$Z^r$, where $12^-$, $Z^r$, and r are each as defined herein. In still another embodiment, in Formula I or II, $R^1$ is $(CH_2CH_2O)_p$-$L^1$-$Z^1$, and $R^4$ and $R^9$ are each independently —$O(CH_2CH_2O)_r$-$L^r$-$Z^r$, where $L^r$, $Z^l$, $Z^r$, p, and r are each as defined herein.

In yet another embodiment, provided herein is a compound Formula III:

or a tautomer or a mixture of two or more tautomers thereof; or a pharmaceutically acceptable solvate or hydrate thereof; wherein:

$R^x$ and $R^Y$ are each independently (a) hydrogen, deuterium, azido, cyano, halo, nitro, sulfo, —$OPO_3H_2$, or $PO_3H_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl, each of which is optionally substituted with one or more substituents Q; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$(O)_2R^{1a}$, —$S(O)NR^{1b}R^{1c}$, or —$S(O)_2NR^{1b}R^{1c}$; and A, $L^1$, $L^6$, $R^{1a}$, $R^{1b}$, $R^{1c}$, $R^{1d}$, X, Y, $Z^1$, $Z^6$, m, p, and q are each as defined herein.

In one embodiment, in Formula I, II, or III, $R^2$ and $R^3$, or $R^4$ and $R^5$, each pair together with the carbon atoms to which they are attached independently form $C_{3-7}$ cycloalkyl, $C_{6-14}$ aryl, heteroaryl, or heterocyclyl, each of which is optionally substituted with one or more substituents Q. In another embodiment, in Formula I, II, or III, $R^2$ and $R^3$, or $R^4$ and $R^5$, each pair together with the carbon atoms to which they are attached independently form $C_{6-20}$ aryl, optionally substituted with one or more substituents Q. In yet another embodiment, in Formula I, II, or III, $R^3$ and $R^4$ together with the carbon atoms to which they are attached independently form $C_{3-7}$ cycloalkyl, $C_{6-14}$ aryl, heteroaryl, or heterocyclyl, each of which is optionally substituted with one or more substituents Q. In still another embodiment, in Formula I, II, or III, $R^3$ and $R^4$ together with the carbon atoms to which they are attached independently form $C_{6-20}$ aryl, optionally substituted with one or more substituents Q.

In one embodiment, in Formula I, II, or III, $R^7$ and $R^8$, or $R^9$ and $R^{10}$, each pair together with the carbon atoms to which they are attached independently form $C_{3-7}$ cycloalkyl, $C_{6-14}$ aryl, heteroaryl, or heterocyclyl, each of which is optionally substituted with one or more substituents Q. In another embodiment, in Formula I, II, or III, $R^7$ and $R^8$, or $R^9$ and $R^{10}$, each pair together with the carbon atoms to which they are attached independently form $C_{6-20}$ aryl, optionally substituted with one or more substituents Q. In yet another embodiment, in Formula I, II, or III, $R^g$ and $R^9$ together with the carbon atoms to which they are attached independently form $C_{3-7}$ cycloalkyl, $C_{6-14}$ aryl, heteroaryl, or heterocyclyl, each of which is optionally substituted with one or more substituents Q. In still another embodiment, in Formula I, II, or III, $R^8$ and $R^9$ together with the carbon atoms to which they are attached independently form $C_{6-20}$ aryl, optionally substituted with one or more substituents Q.-

(III)

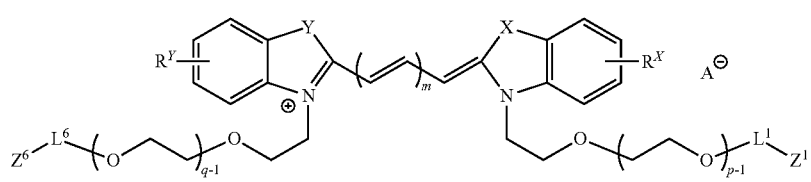

In yet another embodiment, provided herein is a compound Formula IV:

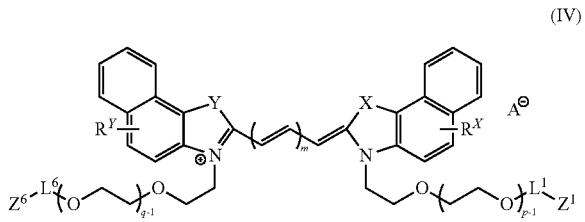

(IV)

or a tautomer or a mixture of two or more tautomers thereof; or a pharmaceutically acceptable solvate or hydrate thereof; wherein $R^X$, $R^Y$, A, $L_1$, $L^6$, X, Y, $Z^1$, $Z^6$ m, p, and q are each as defined herein.

In one embodiment, in any one of Formulae I to IV, m is an integer of 1. In another embodiment, in any one of Formulae III or IV, m is an integer of 2. In yet another embodiment, in any one of Formulae I to IV, m is an integer of 3.

In one embodiment, in Formula III or IV, $R^Y$ is hydrogen or sulfo. In another embodiment, in Formula III or IV, $R^Y$ is hydrogen or sulfo.

In yet another embodiment, provided herein is a compound of Formula V:

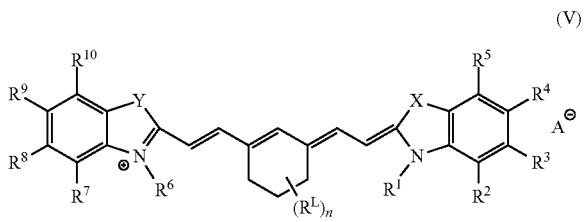

(V)

or a tautomer or a mixture of two or more tautomers thereof; or a pharmaceutically acceptable solvate or hydrate thereof; wherein $R^1$, $R^2$, $R^3$, $R^4$, $R^5$, $R^6$, $R^7$, $R^8$, $R^9$, $R^{10}$, $R^L$, A, X, Y, and n are each as defined herein.

In one embodiment, in Formula V, $R^6$ is (a) hydrogen; (b) $C_{1-10}$ alkyl, optionally substituted with one or more substituents Q; or (c) —$(CH_2CH_2O)_q L^6$-$Z^6$, where $L^6$, $Z^6$, and q are each as defined herein. In another embodiment, in Formula V, $R^6$ is $C_{1-10}$ alkyl, optionally substituted with one or more substituents Q. In yet another embodiment, in Formula V, $R^6$ is methyl or propyl, each of which is optionally substituted with one or more substituents Q. In still another embodiment, in Formula V, $R^6$ is methyl or 3-hydroxypropyl.

In one embodiment, in Formula V, one of $R^2$, $R^3$, $R^4$, and $R^5$ is not hydrogen and the remaining three are each hydrogen. In another embodiment, in Formula V, $R^2$, $R^3$, $R^4$, and $R^5$ are each hydrogen. In yet another embodiment, in Formula V, one of $R^7$, $R^8$, $R^9$, and $R^{10}$ is not hydrogen and the remaining three are each hydrogen. In still another embodiment, in Formula V, $R^7$, $R^8$, $R^9$, and $R^{10}$ are each hydrogen.

In one embodiment, in Formula V, $R^2$ and $R^3$, or $R^4$ and $R^5$, each pair together with the carbon atoms to which they are attached independently form $C_{3-7}$ cycloalkyl, $C_{6-14}$ aryl, heteroaryl, or heterocyclyl, each of which is optionally substituted with one or more substituents Q. In another embodiment, in Formula V, $R^2$ and $R^3$, or $R^4$ and $R^5$, each pair together with the carbon atoms to which they are attached independently form $C_{6-20}$ aryl, optionally substituted with one or more substituents Q. In yet another embodiment, in Formula V, $R^3$ and $R^4$ together with the carbon atoms to which they are attached independently form $C_{3-7}$ cycloalkyl, $C_{6-14}$ aryl, heteroaryl, or heterocyclyl, each of which is optionally substituted with one or more substituents Q. In still another embodiment, in Formula V, $R^3$ and $R^4$ together with the carbon atoms to which they are attached independently form $C_{6-20}$ aryl, optionally substituted with one or more substituents Q.

In one embodiment, in Formula V, $R^7$ and $R^8$, or $R^9$ and $R^{10}$, each pair together with the carbon atoms to which they are attached independently form $C_{3-7}$ cycloalkyl, $C_{6-14}$ aryl, heteroaryl, or heterocyclyl, each of which is optionally substituted with one or more substituents Q. In another embodiment, in Formula V, $R^7$ and $R^8$, or $R^9$ and $R^{10}$, each pair together with the carbon atoms to which they are attached independently form $C_{6-20}$ aryl, optionally substituted with one or more substituents Q. In yet another embodiment, in Formula V, $R^8$ and $R^9$ together with the carbon atoms to which they are attached independently form $C_{3-7}$ cycloalkyl, $C_{6-14}$ aryl, heteroaryl, or heterocyclyl, each of which is optionally substituted with one or more substituents Q. In still another embodiment, in Formula V, $R^8$ and $R^9$ together with the carbon atoms to which they are attached independently form $C_{6-20}$ aryl, optionally substituted with one or more substituents Q.

In yet another embodiment, provided herein is a compound Formula VI:

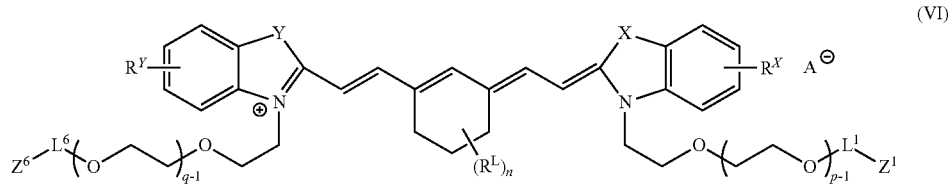

(VI)

or a tautomer or a mixture of two or more tautomers thereof; or a pharmaceutically acceptable solvate or hydrate thereof; wherein $R^L$, $R^X$, $R^Y$, $L^1$, $L^6$, $Z^1$, $Z^6$, A, X, Y, n, p, and q are each as defined herein.

In yet another embodiment, provided herein is a compound Formula VII:

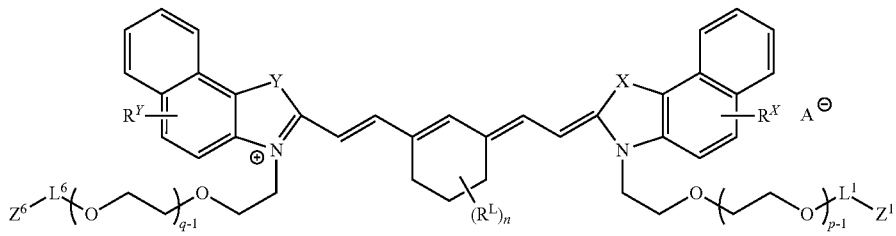

(VII)

or a tautomer or a mixture of two or more tautomers thereof; or a pharmaceutically acceptable solvate or hydrate thereof; wherein $R^L$, $R^X$, $R^Y$, A, $L^1$, $L^6$, X, Y, $Z^6$, $Z^6$, n, p, and q are each as defined herein.

In one embodiment, in any one of Formulae I and V to VII, n is an integer of 0. In another embodiment, in any one of Formulae I and V to VII, n is an integer of 1. In yet another embodiment, in any one of Formulae I and V to VII, n is an integer of 2.

In one embodiment, in Formula VI or VII, $R^L$ is halo. In another embodiment, in Formula VI or VII, $R^L$ is fluoro or chloro. In yet another embodiment, in Formula VI or VII, $R^L$ is chloro.

In one embodiment, in Formula VI or VII, $R^X$ is hydrogen or sulfo. In another embodiment, in Formula VI or VII, $R^Y$ is hydrogen or sulfo.

In one embodiment, in any one of Formulae I to VII, X is $C(R^{Xa}R^{Xb})$, S, or O, where $R^{Xa}$ and $R^{Xb}$ are each as defined herein. In another embodiment, in any one of Formulae I to VII, X is $C(CH_3)$, $C(CH_3)_2$, S, or O. In yet another embodiment, in any one of Formulae I to VII, X is $C(CH_3)_2$. In yet another embodiment, in any one of Formulae I to VII, X is S. In yet another embodiment, in any one of Formulae I to VII, X is O.

In one embodiment, in any one of Formulae I to VII, U is $C(R^{Xa}R^{Xb})$ S, or O, where $R^{Xa}$ and $R^{Xb}$ are each as defined herein. In another embodiment, in any one of Formulae I to VII, Y is $C(CH_3)$, $C(CH_3)_2$, S, or O. In yet another embodiment, in any one of Formulae I to VII, Y is $C(CH_3)_2$. In yet another embodiment, in any one of Formulae I to VII, Y is S. In yet another embodiment, in any one of Formulae I to VII, Y is O.

In one embodiment, in any one of Formulae I to VII, X and Y are each independently $C(R^{Xa}R^{Xb})$, S, or O, where $R^{Xa}$ and $R^{Xb}$ are each as defined herein. In another embodiment, in any one of Formulae I to VII, X and Y are $C(CH_3)$, $C(CH_3)_2$, S, or O. In yet another embodiment, in any one of Formulae I to VII, X and Y are $C(CH_3)_2$. In yet another embodiment, in any one of Formulae I to VII, X and Y are S. In yet another embodiment, in any one of Formulae I to VII, X and Y are O.

In yet another embodiment, provided herein is a compound Formula VIII:

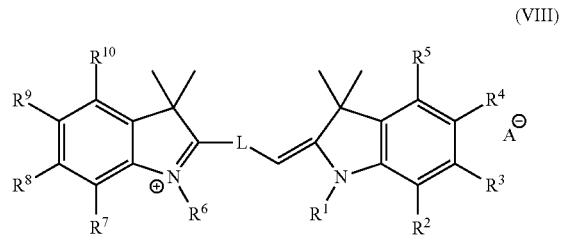

(VIII)

or a tautomer or a mixture of two or more tautomers thereof; or a pharmaceutically acceptable solvate or hydrate thereof; wherein $R^1$, $R^2$, $R^3$, $R^4$, $R^5$, $R^6$, $R^7$, $R^8$, $R^9$, $R^{10}$, A and L are each as defined herein.

In yet another embodiment, provided herein is a compound Formula IX:

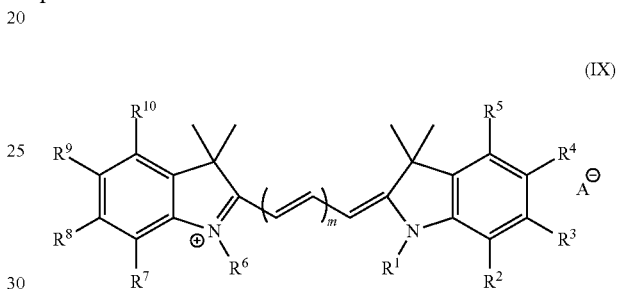

(IX)

or a tautomer or a mixture of two or more tautomers thereof; or a pharmaceutically acceptable solvate or hydrate thereof wherein $R^1$, $R^2$, $R^3$ $R^4$, $R^5$, $R^6$, $R^7$, $R^8$, $R^9$, $R^{10}$, A, and m are each as defined herein.

In one embodiment, in Formula VIII or IX, $R^6$ is (a) hydrogen; (b) $C_{1-10}$ alkyl, optionally substituted with one or more substituents Q; or (c) $-(CH_2CH_2O)_q-L^6-Z^6$, where $L^6$, $Z^6$, and q are each as defined herein. In another embodiment, in Formula VIII or IX, $R^6$ is $C_{1-10}$ alkyl, optionally substituted with one or more substituents Q. In yet another embodiment, in Formula VIII or IX, $R^6$ is methyl or propyl, each of which is optionally substituted with one or more substituents Q. In still another embodiment, in Formula VIII or IX, $R^6$ is methyl or 3-hydroxypropyl.

In one embodiment, in Formula VIII or IX, one of $R^2$, $R^3$, $R^4$, and $R^5$ is not hydrogen and the remaining three are each hydrogen. In another embodiment, in Formula VIII or IX, $R^2$, $R^3$, $R^4$, and $R^5$ are each hydrogen. In yet another embodiment, in Formula VIII or IX, one of $R^7$, $R^8$, $R^9$, and $R^{10}$ is not hydrogen and the remaining three are each hydrogen. In still another embodiment, in Formula VIII or IX, $R^7$, $R^8$, $R^9$, and $R^{10}$ are each hydrogen.

In one embodiment, in Formula VIII or IX, $R^2$ and $R^3$, or $R^4$ and $R^5$, each pair together with the carbon atoms to which they are attached independently form $C_{3-7}$ cycloalkyl, $C_{6-14}$ aryl, heteroaryl, or heterocyclyl, each of which is optionally substituted with one or more substituents Q. In another embodiment, in Formula VIII or IX, $R^2$ and $R^3$, or $R^4$ and $R^5$, each pair together with the carbon atoms to which they are attached independently form $C_{6-20}$ aryl, optionally substituted with one or more substituents Q. In yet another embodiment, in Formula VIII or IX, $R^3$ and $R^4$ together with the carbon atoms to which they are attached independently form $C_{3-7}$ cycloalkyl, $C_{6-14}$ aryl, heteroaryl, or heterocyclyl, each of which is optionally substituted with one or more substituents Q. In still another embodiment, in Formula VIII or IX, $R^3$ and $R^4$ together with the carbon atoms to which they are attached independently form $C_{6-20}$ aryl, optionally substituted with one or more substituents Q.

In one embodiment, in Formula VIII or IX, $R^7$ and $R^8$, or $R^9$ and $R^{10}$, each pair together with the carbon atoms to which they are attached independently form $C_{3-7}$ cycloalkyl, $C_{6-14}$ aryl, heteroaryl, or heterocyclyl, each of which is optionally substituted with one or more substituents Q. In another embodiment, in Formula VIII or IX, $R^7$ and $R^8$, or $R^9$ and $R^{10}$, each pair together with the carbon atoms to which they are attached independently form $C_{6-20}$ aryl, optionally substituted with one or more substituents Q. In yet another embodiment, in Formula VIII or IX, $R^8$ and $R^9$ together with the carbon atoms to which they are attached independently form $C_{3-7}$ cycloalkyl, $C_{6-14}$ aryl, heteroaryl, or heterocyclyl, each of which is optionally substituted with one or more substituents Q. In still another embodiment, in Formula VIII or IX, $R^8$ and $R^9$ together with the carbon atoms to which they are attached independently form $C_{6-20}$ aryl, optionally substituted with one or more substituents Q.

In yet another embodiment, provided herein is a compound Formula X:

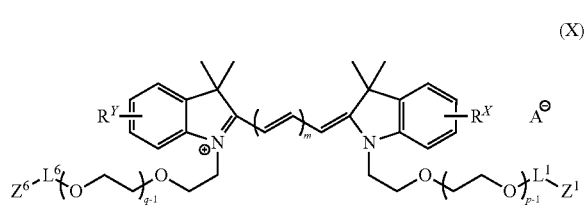

or a tautomer or a mixture of two or more tautomers thereof; or a pharmaceutically acceptable solvate or hydrate thereof; wherein $R^X$, $R^Y$, $L^1$, $L^6$, $L^1$, $Z^6$, A, m, p, and q are each as defined herein.

In yet another embodiment, provided herein is a compound Formula XI:

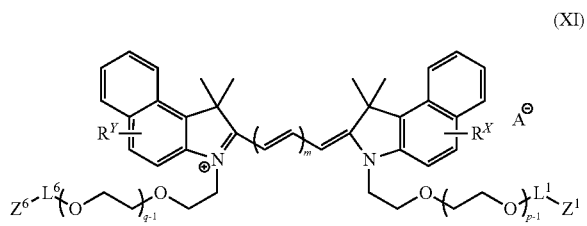

or a tautomer or a mixture of two or more tautomers thereof; or a pharmaceutically acceptable solvate or hydrate thereof; wherein $R^X$, $R^Y$, $L^1$, $L^6$, $Z^1$, $Z^6$, A, m, p, and q are each as defined herein.

In one embodiment, in any one of Formulae VIII to XI, m is an integer of 1. In another embodiment, in any one of Formulae VIII to XI, m is an integer of 2. In yet another embodiment, in any one of Formulae VIII to XI, m is an integer of 3.

In one embodiment, in Formula X or XI, $R^X$ is hydrogen or sulfo. In another embodiment, in Formula X or XI, $R^Y$ is hydrogen or sulfo.

In yet another embodiment, provided herein is a compound of Formula XII:

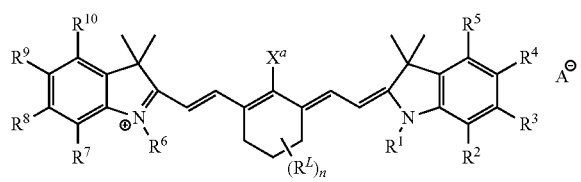

or a tautomer or a mixture of two or more tautomers thereof; or a pharmaceutically acceptable solvate or hydrate thereof; wherein $R^1$, $R^2$, $R^3$, $R^4$, $R^5$, $R^6$, $R^7$, $R^8$, $R^9$, $R^{10}R^L$, $R^L$, $X^a$, A, and n are, each as defined herein.

In one embodiment, in Formula XII, $R^6$ is (a) hydrogen; (b) $C_{1-10}$ alkyl, optionally substituted with one or more substituents Q; or (c) —$(CH_2CH_2O)_q$-$L^6$-$Z^6$, where $L^6$, $Z^6$, and q are each as defined herein. In another embodiment, in Formula XII, $R^6$ is $C_{1-10}$ alkyl, optionally substituted with one or more substituents Q. In yet another embodiment, in Formula XII, $R^6$ is methyl or propyl, each of which is optionally substituted with one or more substituents Q. In yet another embodiment, in Formula XII, $R^6$ is methyl or 3-hydroxypropyl. In still another embodiment, in Formula XII, $R^6$ is —$(CH_2CH_2O)_q$-$L^6$-$Z^6$, where $L^6$, $Z^6$, and q are each as defined herein.

In one embodiment, in Formula XII, one of $R^2$, $R^3$, $R^4$, and $R^5$ is not hydrogen and the remaining three are each hydrogen. In another embodiment, in Formula XII, $R^2$, $R^3$, $R^4$, and $R^5$ are each hydrogen. In yet another embodiment, in Formula XII, one of $R^7$, $R^8$, $R^9$, and $R^{10}$ is not hydrogen and the remaining three are each hydrogen. In still another embodiment, in Formula XII, $R^7$, $R^8$, $R^9$, and $R^{10}$ are each hydrogen.

In one embodiment, in Formula XII, $R^2$ and $R^3$, or $R^4$ and $R^5$, each pair together with the carbon atoms to which they are attached independently form $C_{3-7}$ cycloalkyl, $C_{6-14}$ aryl, heteroaryl, or heterocyclyl, each of which is optionally substituted with one or more substituents Q. In another embodiment, in Formula XII, $R^2$ and $R^3$, or $R^4$ and $R^5$, each pair together with the carbon atoms to which they are attached independently form $C_{6-20}$ aryl, optionally substituted with one or more substituents Q. In yet another embodiment, in Formula XII, $R^3$ and $R^4$ together with the carbon atoms to which they are attached independently form $C_{3-7}$ cycloalkyl, $C_{6-14}$ aryl, heteroaryl, or heterocyclyl, each of which is optionally substituted with one or more substituents Q. In still another embodiment, in Formula XII, $R^3$ and $R^4$ together with the carbon atoms to which they are attached independently form $C_{6-20}$ aryl, optionally substituted with one or more substituents Q.

In one embodiment, in Formula XII, $R^7$ and $R^8$, or $R^9$ and $R^{10}$, each pair together with the carbon atoms to which they are attached independently form $C_{3-7}$ cycloalkyl, $C_{6-14}$ aryl, heteroaryl, or heterocyclyl, each of which is optionally substituted with one or more substituents Q. In another embodiment, in Formula XII, $R^7$ and $R^8$, or $R^9$ and $R^{10}$, each pair together with the carbon atoms to which they are attached independently form $C_{6-20}$ aryl, optionally substituted with one or more substituents Q. In yet another embodiment, in Formula XII, $R^8$ and $R^9$ together with the carbon atoms to which they are attached independently form $C_{3-7}$ cycloalkyl, $C_{6-14}$ aryl, heteroaryl, or heterocyclyl, each of which is optionally substituted with one or more substituents Q. In still another embodiment, in Formula XII, $R^8$ and $R^9$ together with the carbon atoms to which they are attached independently form $C_{6-20}$ aryl, optionally substituted with one or more substituents Q.

In yet another embodiment, provided herein is a compound Formula XIII:

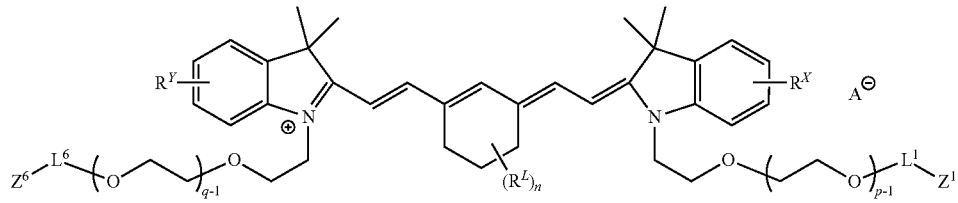

(XIII)

or a tautomer or a mixture of two or more tautomers thereof; or a pharmaceutically acceptable solvate or hydrate thereof; wherein $R^L$, $R^X$, $R^Y$, A, $L^1$, $L^6$, $Z^1$, $Z^6$, n, p, and q are each as defined herein.

In still another embodiment, provided herein is a compound Formula XIV:

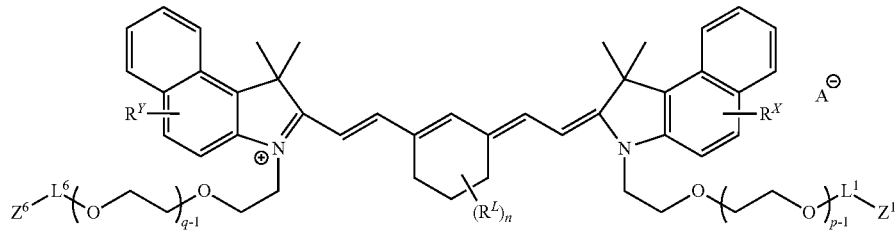

(XIV)

or a tautomer or a mixture of two or more tautomers thereof; or a pharmaceutically acceptable solvate or hydrate thereof; wherein $R^L$, $R^X$, $R^Y$, A, $L^1$, $L^6$, $Z^1$, $Z^6$, n, p, and q are each as defined herein.

In one embodiment, in any one of Formulae XII to XIV, n is an integer of 0. In another embodiment, in any one of Formulae XII to XIV, n is an integer of 1. In yet another embodiment, in any one of Formulae XII to XIV, n is an integer of 2.

In one embodiment, in any one of Formulae XII to XIV, $R^L$ is halo. In another embodiment, in any one of Formulae XII to XIV, $R^L$ is fluoro or chloro. In yet another embodiment, in any one of Formulae XII to XIV, $R^L$ is chloro.

In one embodiment, in Formula XIII or XIV, $R^X$ is hydrogen or sulfo. In another embodiment, in Formula XIII or XIV, $R^Y$ is hydrogen or sulfo.

In yet another embodiment, provided herein is a compound Formula XV:

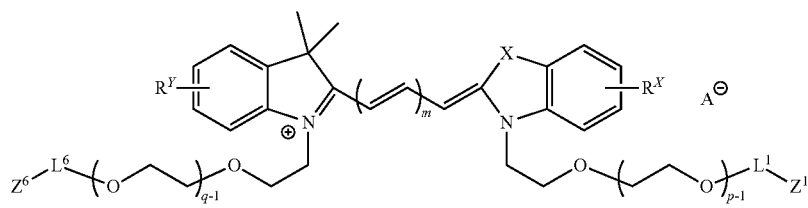

(XV)

or a tautomer or a mixture of two or more tautomers thereof; or a pharmaceutically acceptable solvate or hydrate thereof; wherein: $R^X$, $R^Y$, $L^1$, $L^6$, $Z^1$, $Z_6$, A, X, m, p, and q are each as defined herein.

In still another embodiment, provided herein is a compound Formula XVa:

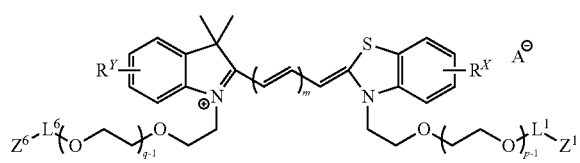

(XVa)

or a tautomer or a mixture of two or more tautomers thereof; or a pharmaceutically acceptable solvate or hydrate thereof; wherein $R^X$, $R^Y$ $L^1$, $L^6$, $Z^1$, $Z^6$, A, m, p, and q are each as defined herein.

In still another embodiment, provided herein is a compound Formula XVb:

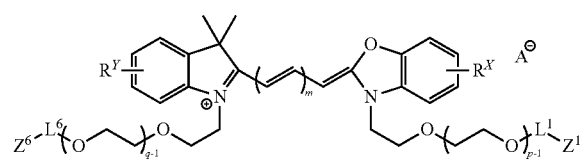

(XVb)

or a tautomer or a mixture of two or more tautomers thereof; or a pharmaceutically acceptable solvate or hydrate thereof; wherein $R^X$, $R^Y$, $L^1$, $L^6$, $Z^1$, $Z^6$, A, m, p, and q are each as defined herein.

In still another emobidment, provided herein is a compound Formula XVI:

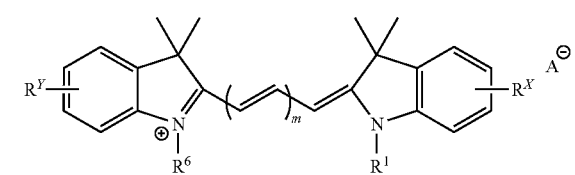

(XVI)

or a tautomer or a mixture of two or more tautomers thereof; or a pharmaceutically acceptable solvate or hydrate thereof; wherein $R^1$, $R^6$, $R^X$, $R^Y$ and m are each as defined herein.

In one embodiment, provided herein is a compound Formula XVIa:

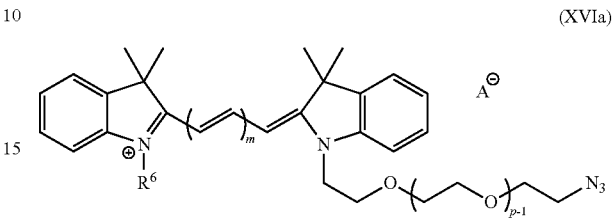

(XVIa)

or a tautomer or a mixture of two or more tautomers thereof; or a pharmaceutically acceptable solvate or hydrate thereof; wherein $R^6$, A, m, and p are each as defined herein.

In another embodiment, provided herein is a compound Formula XVIb:

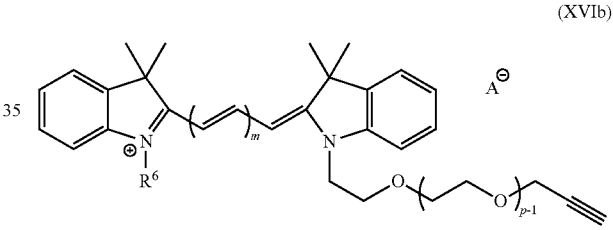

(XVIb)

or a tautomer or a mixture of two or more tautomers thereof; or a pharmaceutically acceptable solvate or hydrate thereof; wherein $R^6$, A, m, and p are each as defined herein.

In yet another embodiment, provided herein is a compound Formula XVIc:

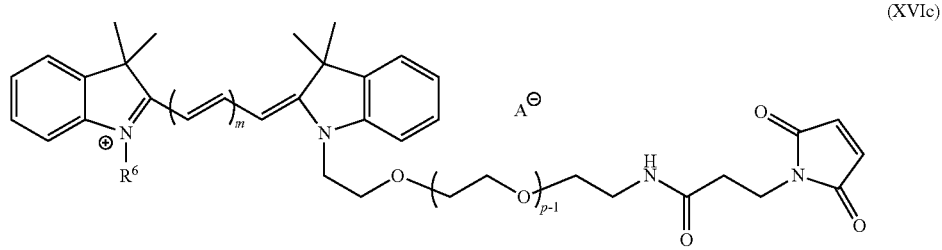

(XVIc)

or a tautomer or a mixture of two or more tautomers thereof; or a pharmaceutically acceptable solvate or hydrate thereof; wherein $R^6$, A, m, and p are each as defined herein.

In yet another embodiment, provided herein is a compound Formula XVId:

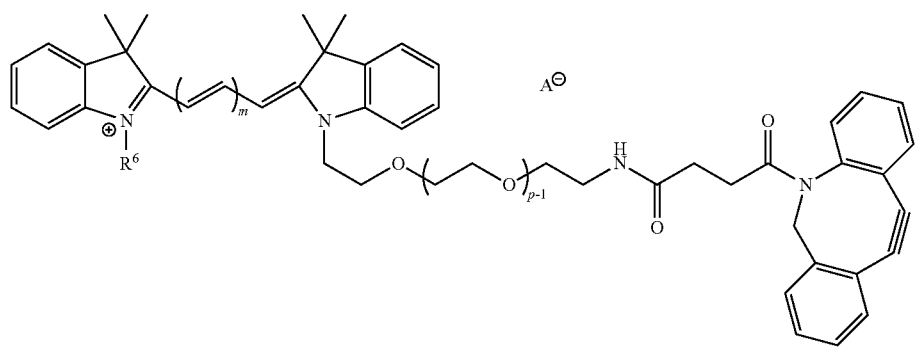

(XVId)

or a tautomer or a mixture of two or more tautomers thereof; or a pharmaceutically acceptable solvate or hydrate thereof; wherein $R^6$, A, m, and p are each as defined herein.

In still another embodiment, provided herein is a compound Formula XVIe:

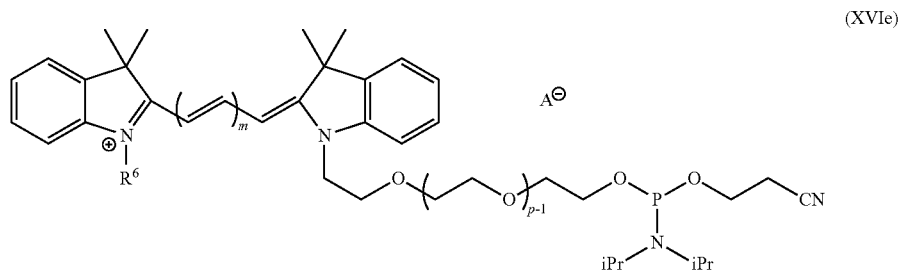

(XVIe)

or a tautomer or a mixture of two or more tautomers thereof; or a pharmaceutically acceptable solvate or hydrate thereof; wherein $R^6$, A, m, and p are each as defined herein.

In still another emobidment, provided herein is a compound Formula XVIf:

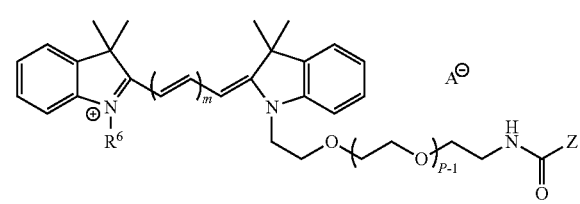

(XVIf)

or a tautomer or a mixture of two or more tautomers thereof; or a pharmaceutically acceptable solvate or hydrate thereof; wherein $R^6$, A, m, and p are each as defined herein. Z is (a) hydrogen, deuterium, halo, O, S, N, or Se; (b) $Z^1$ or $Z^6$; or (c) $R^{Xc}Z^1$, $R^{Xa}R^{Xc}Z^1$, $R^{Xc}Z^6$, $R^{Xa}R^{Xc}Z^6$, $C(R^{Xa}R^{Xb})$, or $NR^{Xc}$, wherein $R^{Xa}$, $R^{Xb}$, $R^{Xc}$, $Z^1$, and $Z^6$ are each as defined herein.

In still another emobidment, provided herein is a compound Formula XVIg:

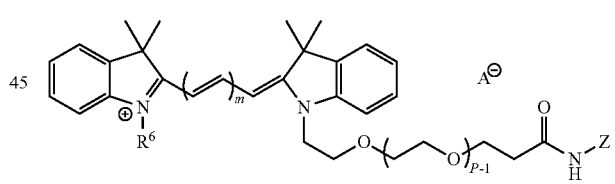

(XVIg)

or a tautomer or a mixture of two or more tautomers thereof; or a pharmaceutically acceptable solvate or hydrate thereof; wherein $R^6$, A, Z, m, and p are each as defined herein.

In still another emobidment, provided herein is a compound Formula XVII:

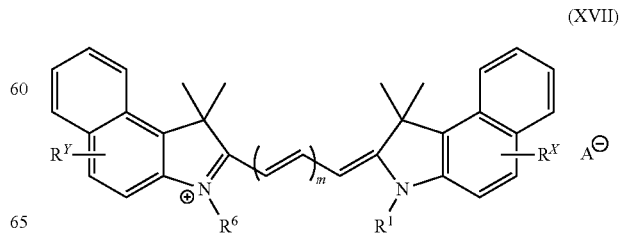

(XVII)

or a tautomer or a mixture of two or more tautomers thereof; or a pharmaceutically acceptable solvate or hydrate thereof; wherein $R^1$, $R^6$, $R^X$, $R^Y$ and m are each as defined herein In yet another embodiment, provided herein is a compound Formula XVIII:

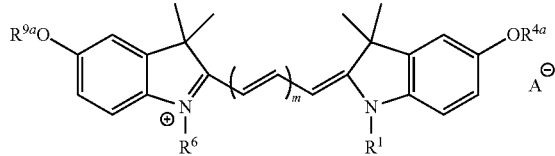

(XVIII)

or a tautomer or a mixture of two or more tautomers thereof; or a pharmaceutically acceptable solvate or hydrate thereof; wherein $R^1$, $R^6$, A, and m are each as defined herein. $R^{9a}$ and $R^{4a}$ are independently (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl, each of which is optionally substituted with one or more substituents Q; (c) —R1a, —OR1a, NR1bR1c, —C(O)$R^{1a}$, —C(O)O$R^{1a}$, —C(O)N$R^{1b}R^{1c}$, —C(N$R^{1a}$)N$R^{1b}R^{1c}$, —C(=N$R^{1a}$)N$R^{1b}R^{1c}$, —S(O)$R^{1a}$, —S(O)$_2R^{1a}$, —S(O)N$R^{1b}R^{1c}$, —S(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, or (d) —(CH$_2$CH$_2$O)$_q$-$L^1$-$Z^1$; wherein $R^{1a}$, $R^{1b}$, $R^{1c}$, $L^1$, $Z^1$, Q, and q are each as defined herein In yet another embodiment, provided herein is a compound Formula XIX:

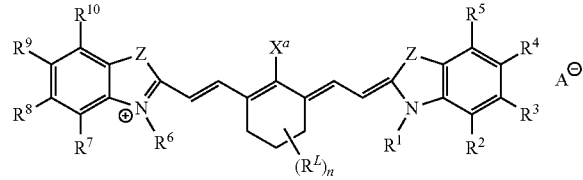

(XIX)

or a tautomer or a mixture of two or more tautomers thereof; or a pharmaceutically acceptable solvate or hydrate thereof; wherein $R^1$, $R^2$, $R^3$, $R^4$, $R^5$, $R^6$, $R^7$, $R^8$, $R^9$, $R^{10}$, $R^L$, $X^a$, A, Z, and n are each as defined herein.

In yet another embodiment, provided herein is a compound Formula XIXa:

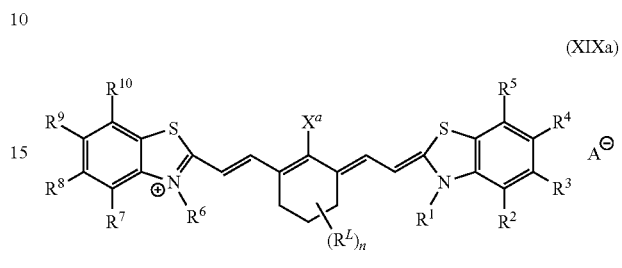

(XIXa)

or a tautomer or a mixture of two or more tautomers thereof; or a pharmaceutically acceptable solvate or hydrate thereof; wherein $R^1$, $R^2$, $R^3$, $R^4$, $R^5$, $R^6$, $R^7$, $R^8$, $R^9$, $R^{10}$, $R^L$, $R^a$, A and n are each as defined herein.

In yet another embodiment, provided herein is a compound Formula XIXb:

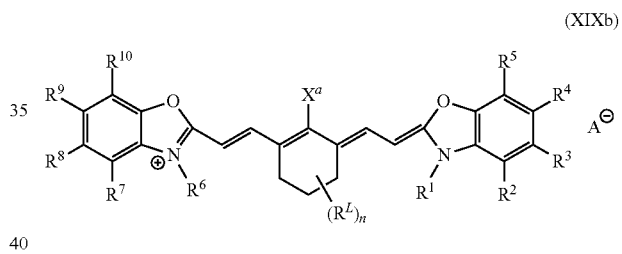

(XIXb)

or a tautomer or a mixture of two or more tautomers thereof; or a pharmaceutically acceptable solvate or hydrate thereof; wherein R $R^1$, $R^2$, $R^3$, $R^4$, $R^5$, $R^6$, $R^7$, $R^8$, $R^9$, $R^{10}$, $R^L$, $X^a$, A and n are each as defined herein.

In yet another embodiment, provided herein is a compound Formula XIXc:

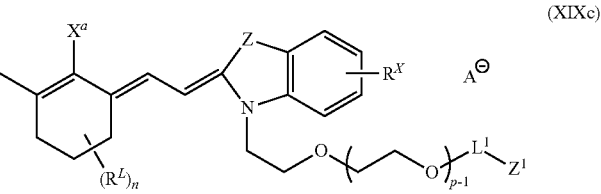

(XIXc)

or a tautomer or a mixture of two or more tautomers thereof; or a pharmaceutically acceptable solvate or hydrate thereof; wherein $R^X$, $R^Y$, $L^1$, $L^6$, $Z^1$, $Z^6$, $X^a$, A, Z, n, p, and q arfe each as defined herein.

In yet another embodiment, provided herein is a compound Formula XX:

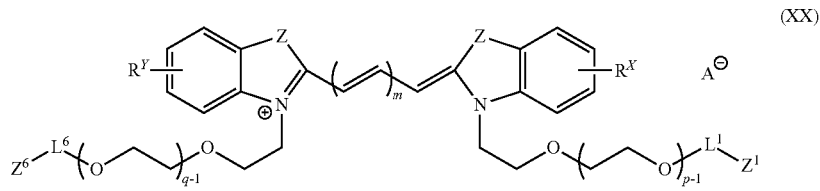

(XX)

or a tautomer or a mixture of two or more tautomers thereof; or a pharmaceutically acceptable solvate or hydrate thereof; wherein $R^X$, $R^Y$, $L^1$, $L^6$, A, Z, m, p, and q are each as defined herein.

In yet another embodiment, provided herein is a compound Formula XXa:

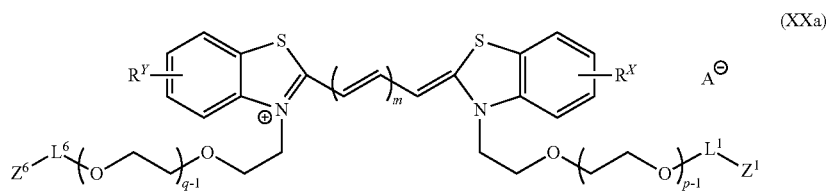

(XXa)

or a tautomer or a mixture of two or more tautomers thereof; or a pharmaceutically acceptable solvate or hydrate thereof; wherein $R^X$, $R^Y$, $L^1$, $L^6$, $Z^1$, $Z^6$, A, m, p, and q are each as defined herein.

In yet another embodiment, provided herein is a compound Formula XXb:

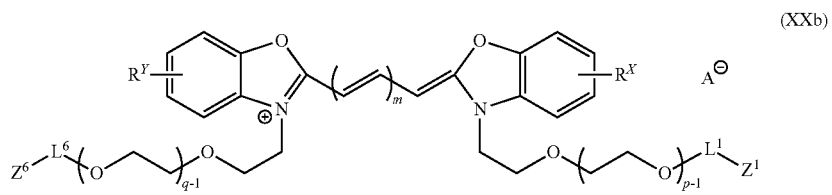

(XXb)

or a tautomer or a mixture of two or more tautomers thereof; or a pharmaceutically acceptable solvate or hydrate thereof; wherein $R^X$, $R^Y$, $L^1$, $L^6$, $Z^1$, $Z^6$, A, m, p, and q are each as defined herein.

In yet another embodiment, provided herein is a compound Formula XXc:

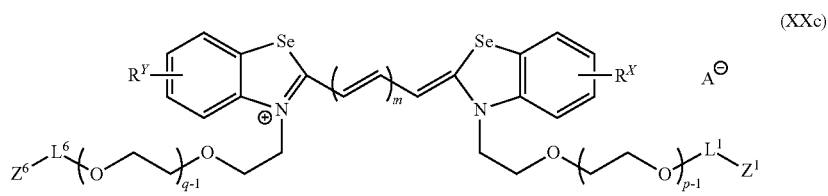

(XXc)

or a tautomer or a mixture of two or more tautomers thereof; or a pharmaceutically acceptable solvate or hydrate thereof; wherein $R^X$, $R^Y$, $L^1$, $L^6$, $Z^1$, $Z^6$, A, m, p, and q are each as defined herein.

In one embodiment, in any one of the formulae provided herein, including Formulae I to XX, XVa to XVb, XVIa to XVIg, XIXa to XIXc, and XXa to XXc, each functional group or constituent is as shown below.

| Ref | Functional Group/Constituent |
|---|---|
| A | an anion bearing a negative charge |
| L | 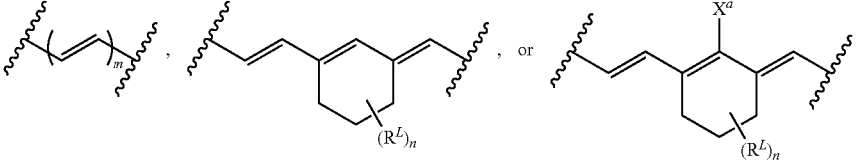 |
| $R^L$ | (a) hydrogen, deuterium, azido, cyano, halo, nitro, oxo, sulfo, —$OPO_3H_2$, or —$PO_3H_2$;<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; or<br>(c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$ |
| $X^a$ | (a) hydrogen, deuterium, azido, cyano, halo, nitro, oxo, sulfo, —$OPO_3H_2$, or —$PO_3H_2$;<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; , each of which is optionally substituted with one or more substituents Q;<br>(c) —$C(R^{1a}R^{1b})$, —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;<br>(d) —$(CH_2CH_2O)_p$—$L^1$—$Z^1$, —$(CH_2CH_2O)_p$—COOH, —$(CH_2CH_2O)_p$—$N_3$, —$(CH_2CH_2O)_p$—OH, —$(CH_2CH_2O)_p$-alkyne, —$(CH_2CH_2O)_p$-biotin, —$(CH_2CH_2O)_p$-NHS ester, —$(CH_2CH_2O)_p$-amine, —$(CH_2CH_2O)_p$-DBCO, —$(CH_2CH_2O)_p$-Fmoc, —$(CH_2CH_2O)_p$-aldehyde, —$(CH_2CH_2O)_p$-phosphonate, —$(CH_2CH_2O)_p$-tosylate, —$(CH_2CH_2O)_p$-FPF ester, —$(CH_2CH_2O)_p$-Boc, —$(CH_2CH_2O)_p$-aminooxy, —$(CH_2CH_2O)_p$-bromo, —$(CH_2CH_2O)_p$-mal, or —$(CH_2CH_2O)_p$-propargyl; or<br>(e) carboxycylic acid, amine, azide, DBCO, hydrazide, maleimide, NHS ester, TCO, tetrazine, or biotin |
| m | integer of 1, 2, or 3 |
| n | integer of 0, 1, 2, 3, 4, 5, 6, or 7 |
| X | $C(R^{Xa}R^{Xb})$, O, S, or $NR^{Xc}$ |
| Y | $C(R^{Xa}R^{Xb})$, O, S, or $NR^{Xc}$ |
| $R^{Xa}$ | (a) hydrogen or deuterium; or<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; |
| $R^{Xb}$ | (a) hydrogen or deuterium; or<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; |
| $R^{Xc}$ | (a) hydrogen or deuterium;<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; or<br>(c) —$C(O)R^{1a}$, —$C(O)OR^{1a}$, —$C(O)NR^{1b}R^{1c}$, —$C(NR^{1a})NR^{1b}R^{1c}$, —$S(O)R^{1a}$, —$S(O)_2R^{1a}$, —$S(O)NR^{1b}R^{1c}$, or —$S(O)_2NR^{1b}R^{1c}$; |
| $R^1$ | (a) hydrogen or deuterium;<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl;<br>(c) —$C(O)R^{1a}$, —$C(O)OR^{1a}$, —$C(O)NR^{1b}R^{1c}$, —$C(NR^{1a})NR^{1b}R^{1c}$, —$S(O)R^{1a}$, —$S(O)_2R^{1a}$, —$S(O)NR^{1b}R^{1c}$, or —$S(O)_2NR^{1b}R^{1c}$; or<br>(d) —$(CH_2CH_2O)_p$—$L^1$—$Z^1$ |
| $L^1$ | $C_{1-10}$ alkylene, $C_{1-10}$ heteroalkylene, $C_{2-10}$ alkenylene, $C_{2-10}$ alkynylene, $C_{3-15}$ cycloalkylene, $C_{1-10}$ heteroalkylene-$C_{3-15}$ cycloalkylene, $C_{6-20}$ arylene, $C_{7-20}$ aralkylene, heteroarylene, or heterocyclylene |
| $Z^1$ | (a) amino, azido, chloro, bromo, iodo, or thiol;<br>(b) N-maleimido, N-3,4-dibromo-maleimido, $C_{2-6}$ alkynyl, heterocyclyl containing a carbon-carbon triple, acrylyl, 3-sulfo-N-succinimidyloxycarbonyl, tetrafluorophenoxycarbonyl, pentofluorophenoxycarbonyl, $C_{2-6}$ alkynyloxy, $C_{3-15}$ cycloalkyloxy containing a carbon-carbon triple, $C_{6-20}$ aryloxy containing a carbon-carbon triple, or heterocyclyloxy containing a carbon-carbon triple;<br>(c) —$OP(OR^{1a})(NR^{1b}R^{1c})$, —$OP((NR^{1b}R^{1c})_2$, —$OS(O)_2R^{1a}$, or —S—$SR^{1a}$; or<br>(d) $Z^6$ |
| p | integer of 1 to 50 |
| $R^2$, $R^3$, $R^4$, $R^5$, $R^7$, $R^8$, $R^9$, and $R^{10}$ | independently (a) hydrogen, deuterium, azido, cyano, halo, nitro, sulfo, —$OPO_3H_2$, or —$PO_3H_2$;<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl;<br>(c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, |

| Ref | Functional Group/Constituent |
|---|---|
| | $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$; (d) $R^2$ and $R^3$, $R^4$ and $R^5$, $R^7$ and $R^8$, or $R^9$ and $R^{10}$, each pair together with the carbon atoms to which they are attached independently form $C_{3-15}$ cycloalkyl, $C_{6-20}$ aryl, heteroaryl, or heterocyclyl; (e) $R^3$ and $R^4$, or $R^8$ and $R^9$, each pair together with the carbon atoms to which they are attached independently form $C_{3-15}$ cycloalkyl, $C_{6-20}$ aryl, heteroaryl, or heterocyclyl; or (f) $-O(CH_2CH_2O)_r-L^r-Z^r$, with the proviso that when $R^1$ is not $-(CH_2CH_2O)_p-L^1-Z^1$, at least one of $R^1$, $R^2$, $R^3$, $R^4$, $R^5$, $R^7$, $R^8$, $R^9$, and $R^{10}$ is $-O(CH_2CH_2O)_r-L^r-Z^r$ |
| $L^r$ | $C_{1-10}$ alkylene, $C_{1-10}$ heteroalkylene, $C_{2-10}$ alkenylene, $C_{2-10}$ alkynylene, $C_{3-15}$ cycloalkylene, $C_{1-10}$ heteroalkylene-$C_{3-15}$ cycloalkylene, $C_{6-20}$ arylene, $C_{7-20}$ aralkylene, heteroarylene, or heterocyclylene |
| $Z^r$ | (a) hydrogen, deuterium, halo, cyano, nitro, sulfo, $-OPO_3H_2$, or $-PO_3H_2$; |
| | (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; |
| | (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$; or |
| | (d) $Z^1$ |
| r | integer of 1 to 50 |
| $R^6$ | (a) hydrogen or deuterium; |
| | (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; |
| | (c) $-C(O)R^{1a}$, $-C(O)OR^{1a}$, $-C(O)NR^{1b}R^{1c}$, $-C(NR^{1a})NR^{1b}R^{1c}$, $-S(O)R^{1a}$, $-S(O)_2R^{1a}$, $-S(O)NR^{1b}R^{1c}$, or $-S(O)_2NR^{1b}R^{1c}$; or |
| | (d) $-(CH_2CH_2O)_q-L^6-Z^6$ |
| $L^6$ | $C_{1-10}$ alkylene, $C_{1-10}$ heteroalkylene, $C_{2-10}$ alkenylene, $C_{2-10}$ alkynylene, $C_{3-15}$ cycloalkylene, $C_{6-20}$ arylene, $C_{7-20}$ aralkylene, heteroarylene, or heterocyclylene |
| $Z^6$ | (a) hydrogen, deuterium, halo, cyano, nitro, sulfo, $-OPO_3H_2$, or $-PO_3H_2$; |
| | (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; |
| | (c) $-C(O)R^{1a}$, $-C(O)OR^{1a}$, $-C(O)NR^{1b}R^{1c}$, $-C(NR^{1a})NR^{1b}R^{1c}$, $-OR^{1a}$, $-OC(O)R^{1a}$, $-OC(O)OR^{1a}$, $-OC(O)NR^{1b}R^{1c}$, $-OC(=NR^{1a})NR^{1b}R^{1c}$, $-OS(O)R^{1a}$, $-OS(O)_2R^{1a}$, $-OS(O)NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(=NR^{1d})NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$, or $-S(O)_2NR^{1b}R^{1c}$; or |
| | (d) $Z^1$ |
| q | integer of 1 to 50 |
| $R^{1a}$, $R^{1b}$, $R^{1c}$, and $R^{1d}$ | independently (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) $R^{1a}$ and $R^{1c}$ together with the C and N atoms to which they are attached form heterocyclyl; or (d) $R^{1b}$ and $R^{1c}$ together with the N atom to which they are attached form heteroaryl or heterocyclyl |
| Q | independently (a) deuterium, azido, cyano, halo, nitro, oxo, sulfo, $-OPO_3H_2$, and $-PO_3H_2$; |
| | (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; or |
| | (c) $-C(O)R^a$, $-C(O)OR^a$, $-C(O)NR^bR^c$, $-C(NR^a)NR^bR^c$, $-OR^a$, $-OC(O)R^a$, $-OC(O)OR^a$, $-OC(O)NR^bR^c$, $-OC(=NR^a)NR^bR^c$, $-OS(O)R^a$, $-OS(O)_2R^a$, $-OS(O)NR^bR^c$, $-OS(O)_2NR^bR^c$, $-NR^bR^c$, $-NR^aC(O)R^d$, $-NR^aC(O)OR^d$, $-NR^aC(O)NR^bR^c$, $-NR^aC(=NR^d)NR^bR^c$, $-NR^aS(O)R^d$, $-NR^aS(O)_2R^d$, $-NR^aS(O)NR^bR^c$, $-NR^aS(O)_2NR^bR^c$, $-SR^a$, $-S(O)R^a$, $-S(O)_2R^a$, $-S(O)NR^bR^c$, and $-S(O)_2NR^bR^c$ |
| $R^a$, $R^b$, $R^c$, and $R^d$ | independently (a) hydrogen or deuterium; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents $Q^a$; or (c) $R^b$ and $R^c$ together with the N atom to which they are attached form heteroaryl or heterocyclyl, each of which is further optionally substituted with one or more, in one embodiment, one, two, three, or four, substituents $Q^a$ |
| $Q^a$ | (a) deuterium, azido, cyano, halo, nitro, oxo, sulfo, $-OPO_3H_2$, and $-PO_3H_2$; |
| | (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and |
| | (c) $-C(O)R^e$, $-C(O)OR^e$, $-C(O)NR^fR^g$, $-C(NR^e)NR^fR^g$, $-OR^e$, $-OC(O)R^e$, $-OC(O)OR^e$, $-OC(O)NR^fR^g$, $-OC(=NR^e)NR^fR^g$, $-OS(O)R^e$, $-OS(O)_2R^e$, $-OS(O)NR^fR^g$, $-OS(O)_2NR^fR^g$, $-NR^fR^g$, $-NR^eC(O)R^h$, $-NR^eC(O)OR^f$, $-NR^eC(O)NR^fR^g$, $-NR^eC(=NR^h)NR^fR^g$, $-NR^eS(O)R^h$, $-NR^eS(O)_2R^h$, $-NR^eS(O)NR^fR^g$, $-NR^eS(O)_2NR^fR^g$, $-SR^e$, $-S(O)R^e$, $-S(O)_2R^e$, $-S(O)NR^fR^g$, and $-S(O)_2NR^fR^g$ |

-continued

| Ref | Functional Group/Constituent |
|---|---|
| $R^e$, $R^f$, $R^g$, and $R^h$ | independently (a) hydrogen or deuterium;<br>(b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or<br>(c) $R^f$ and $R^g$ together with the N atom to which they are attached form heteroaryl or heterocyclyl |
| $R^X$ and $R^Y$ | independently (a) hydrogen, deuterium, azido, cyano, halo, nitro, sulfo, —$OPO_3H_2$, —$PO_3H_2$;<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl, each of which is optionally substituted with one or more substituents Q; or<br>(c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, -$S(O)_2R^{1a}$, —$S(O)NR^{1b}R^{1c}$, or —$S(O)_2NR^{1b}R^{1c}$ |
| Z | (a) hydrogen, deuterium, halo, O, S, N, or Se;<br>(b) $Z^1$ or $Z^6$; or<br>(c) $R^{Xc}Z^1$, $R^{Xa}R^{Xc}Z^1$, $R^{Xc}Z^6$, $R^{Xa}R^{Xc}Z^6$, $C(R^{Xa}R^{Xb})$, or $NR^{Xc}$ |
| $R^{9a}$ and $R^{4a}$ | independently (a) hydrogen or deuterium;<br>(b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl, each of which is optionally substituted with one or more substituents Q;<br>(c) —R1a, —OR1a, —NR1bR1c, —$C(O)R^{1a}$, —$C(O)OR^{1a}$, —$C(O)NR^{1b}R^{1c}$, —$C(NR^{1a})NR^{1b}R^{1c}$, —$C(=NR^{1a})NR^{1b}R^{1c}$, —$S(O)R^{1a}$, —$S(O)_2R^{1a}$, —$S(O)NR^{1b}R^{1c}$, —$S(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, or<br>(d) —$(CH_2CH_2O)_q$—$L^1$—$Z^1$ |

In one embodiment, in any one of the formulae provided herein, including Formulae I to XX, XVa to XVb, XVIa to XVIg, XIXa to XIXc, and XXa to XXc, A is an anion of acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(15)-camphor-10-sulfonic acid, capric acid, caproic acid, caprylic acid, cinnamic acid, citric acid, cyclamic acid, cyclohexanesulfamic acid, dodecyl sulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, a-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In another embodiment, in any one of the formulae provided herein, including Formulae I to XX, XVa to XVb, XVIa to XVIg, XIXa to XIXc, and XXa to XXc, A is fluoride (F), chloride (Cr), bromide (Br−), iodide (F), acetate ($CH_3CO_2^-$), phosphate ($PO_4H_2^-$, $PO_4H^{2-}$, or $PO_4^{3-}$), or sulfate ($SO_4^-$ or $SO_4^{2-}$). In yet another embodiment, in any one of the formulae provided herein, including Formulae I to XX, XVa to XVb, XVIa to XVIg, XIXa to XIXc, and XXa to XXc, A is chloride.

In one embodiment, in any one of the formulae provided herein, including Formulae I to XX, XVa to XVb, XVIa to XVIg, XIXa to XIXc, and XXa to XXc, $L^1$ is $C_{1-10}$ alkylene, optionally substituted with one or more substituents Q. In another embodiment, in any one of the formulae provided herein, including Formulae I to XX, XVa to XVb, XVIa to XVIg, XIXa to XIXc, and XXa to XXc, $L^1$ is methylene, ethylene, propylene, butylenes, pentylene, or hexylene, each of which is optionally substituted with one or more substituents Q. In yet another embodiment, in any one of the formulae provided herein, including Formulae I to XX, XVa to XVb, XVIa to XVIg, XIXa to XIXc, and XXa to XXc, $L^1$ is methylene, 1,2-ethylene, 1,3-propylene, 1,4-butylenes, 1,5-pentylene, or 1,6-hexylene, each optionally substituted with one or more substituents Q. In still another embodiment, in any one of the formulae provided herein, including Formulae I to XX, XVa to XVb, XVIa to XVIg, XIXa to XIXc, and XXa to XXc, $L^1$ is methylene, 1,2-ethylene, or 1,3-propylene.

In one embodiment, in any one of the formulae provided herein, including Formulae I to XX, XVa to XVb, XVIa to XVIg, XIXa to XIXc, and XXa to XXc, $L^1$ is $C_{1-10}$ heteroalkylene, optionally substituted with one or more substituents Q. In another embodiment, in any one of the formulae provided herein, including Formulae I to XX, XVa to XVb, XVIa to XVIg, XIXa to XIXc, and XXa to XXc, $L^1$ is —$(CH_2)_2O$—, —$(CH_2)_2OCH_2$-, —$CH_2NH$—, —$CH_2NHCH_2$—, —$(CH_2)_2NH$—, —$(CH_2)_2NHC(O)$—, —$(CH_2)_2NHC(O)CH_2$—, —$(CH_2)_2NHC(O)(CH_2)_2$—, —$(CH_2)_2NHC(O)(CH_2)_3$—, —$(CH_2)_2NHC(O)(CH_2)_5$—, —$(CH_2)_6NHC(O)(CH_2)_2$—, —$(CH_2)_2NHC(O)(CH_2)_2C(O)$—, —$(CH_2)_2NHC(O)(CH_2)_4C(O)$—, —$(CH_2)_2C(O)NH(CH_2)_2C(O)$—, —$(CH_2)_2C(O)NH(CH_2)_4C(O)$—, —$(CH_2)_2NHC(O)CH(SO_3H)CH_2NHC(O)(CH_2)_2C(O)$—, —$(CH_2)_2C(O)NH(CH_2)_3$—, or —$(CH_2)_2C(O)NH(CH_2)_4CH_2$—.

In one embodiment, in any one of the formulae provided herein, including Formulae I to XX, XVa to XVb, XVIa to XVIg, XIXa to XIXc, and XXa to XXc, $L^1$ is $C_{1-10}$ heteroalkylene-$C_{3-15}$ cycloalkylene, where the heteroalkylene and cycloalkylene are each independently and optionally substituted with one or more substituents Q.

In one embodiment, in any one of the formulae provided herein, including Formulae I to XX, XVa to XVb, XVIa to XVIg, XIXa to XIXc, and XXa to XXc, $Z^1$ is $C_{2-6}$ alkynyl, optionally substituted with one or more substituents Q. In another embodiment, in any one of the formulae provided herein, including Formulae I to XX, XVa to XVb, XVIa to XVIg, XIXa to XIXc, and XXa to XXc, $Z^1$ is heterocyclyl containing a carbon-carbon triple, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^1$ is $C_{2-6}$ alkynyloxy, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^1$ is $C_{3-15}$ cycloalkyloxy containing a carbon-carbon triple, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^1$ is $C_{6-20}$ aryloxy containing a carbon-carbon triple, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^1$ is heterocyclyloxy containing a carbon-carbon triple, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^1$ is $-OP(OR^{1a})(NR^{1b}R^{1c})$, wherein $R^{1a}$, $R^{1b}$, and $R^{1c}$ are each as defined herein. In yet another embodiment, in any one of the formulae provided herein, including Formulae I to XX, XVa to XVb, XVIa to XVIg, XIXa to XIXc, and XXa to XXc, $Z_1$ is $-OP((NR^{1b}R^{1c})_2)$, wherein $R^{1b}$ and $R^{1c}$ are each as defined herein. In yet another embodiment, in any one of the formulae provided herein, including Formulae I to XX, XVa to XVb, XVIa to XVIg, XIXa to XIXc, and XXa to XXc, $Z^1$ is $-OS(O)_2R^{1a}$, wherein $R^{1a}$ is as defined herein. In still another embodiment, in any one of the formulae provided herein, including Formulae I to XX, XVa to XVb, XVIa to XVIg, XIXa to XIXc, and XXa to XXc, $Z^1$ is $SSR^{1a}$, wherein $R^{1a}$ is as defined herein.

In one embodiment, in any one of the formulae provided herein, including Formulae I to XX, XVa to XVb, XVIa to XVIg, XIXa to XIXc, and XXa to XXc, $Z^1$ is:

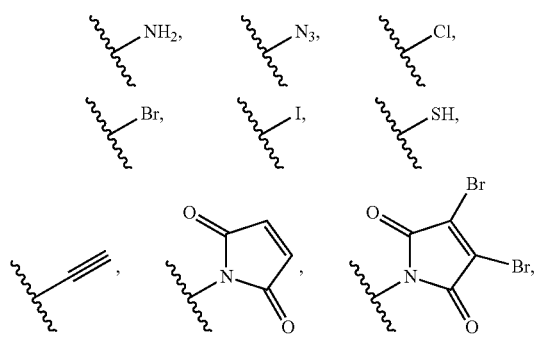

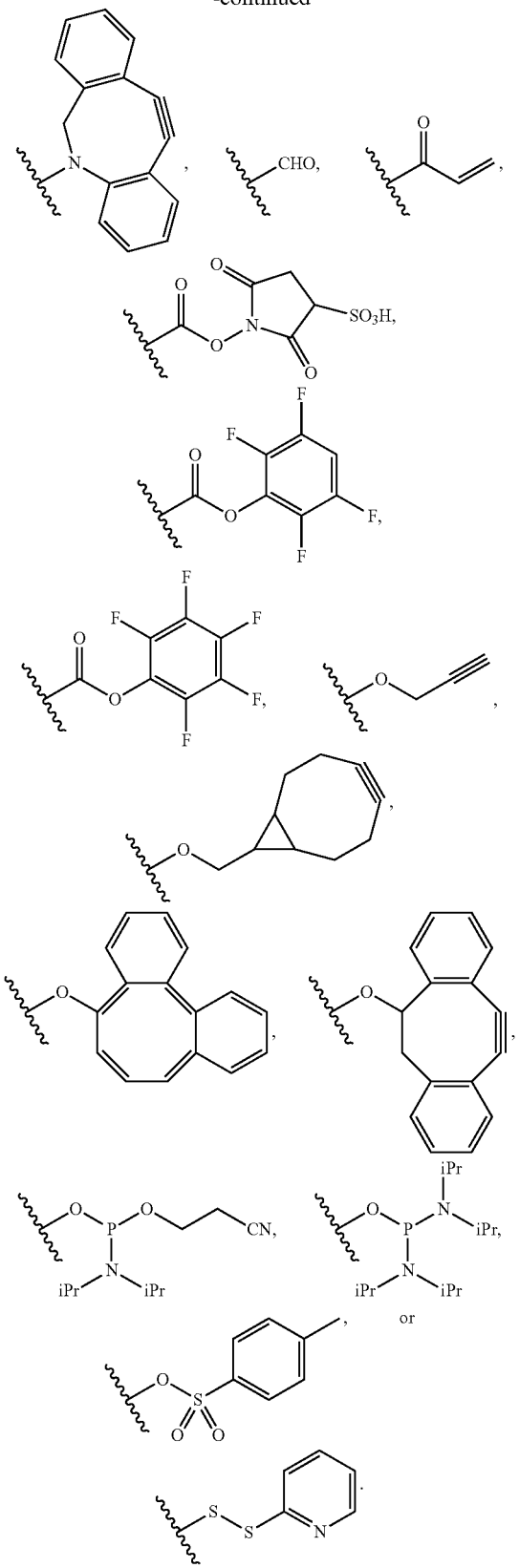

In another embodiment, in any one of the formulae provided herein, including Formulae I to XX, XVa to XVb, XVIa to XVIg, XIXa to XIXc, and XXa to XXc, $L^1$-$Z^1$ is:

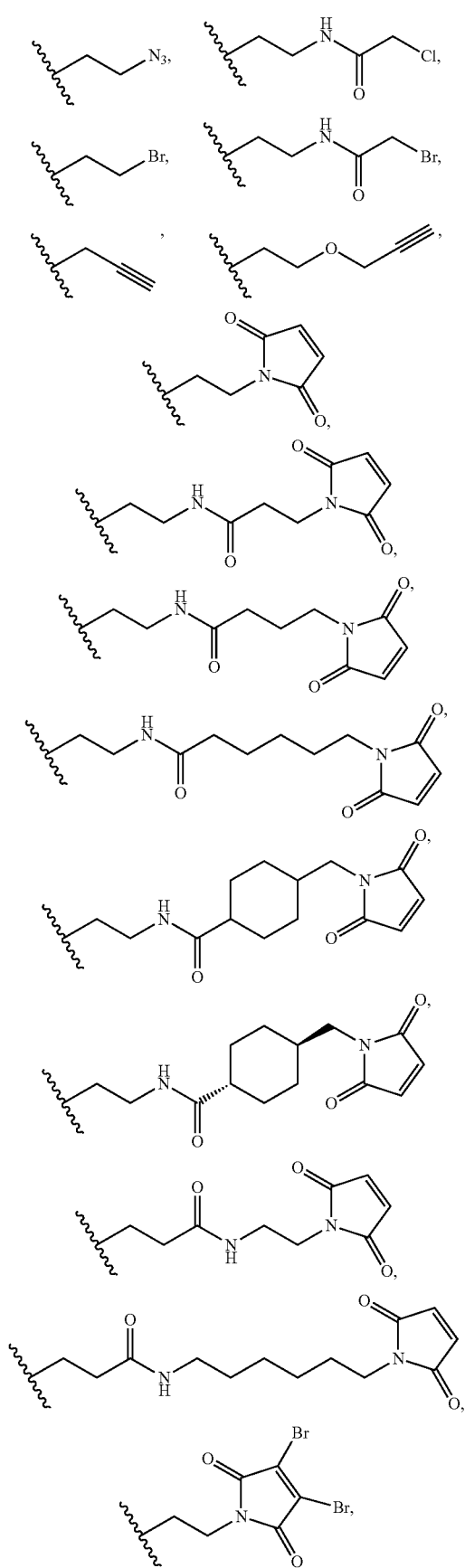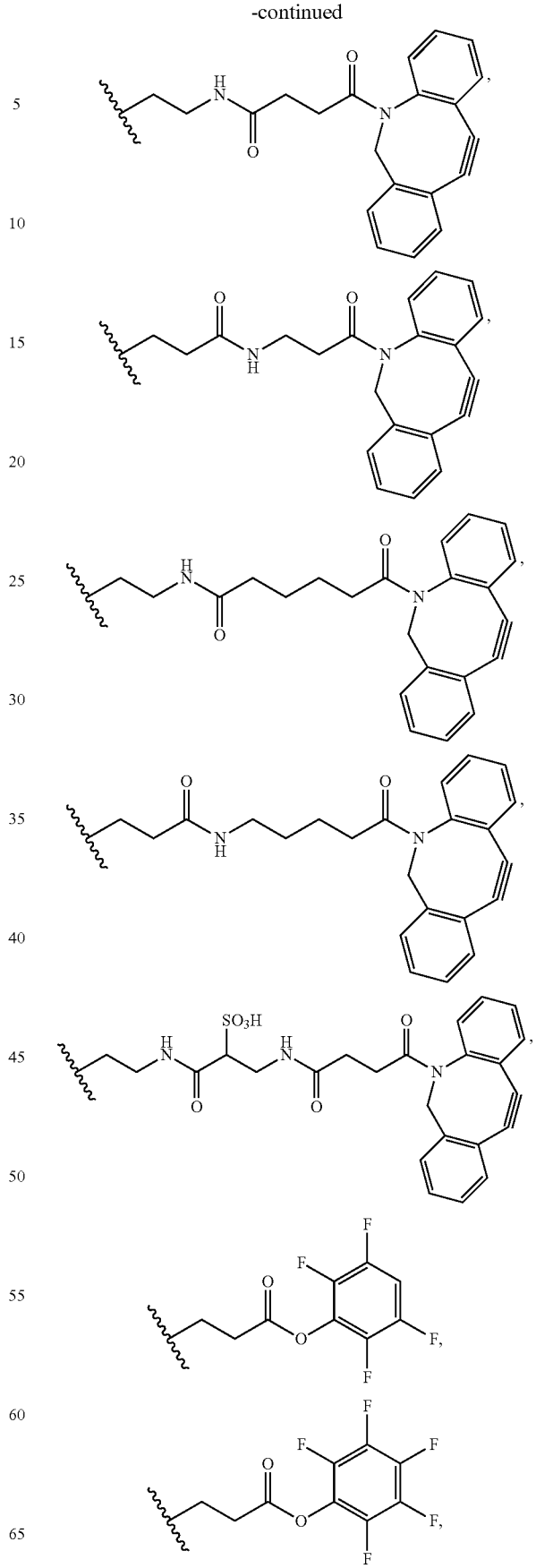

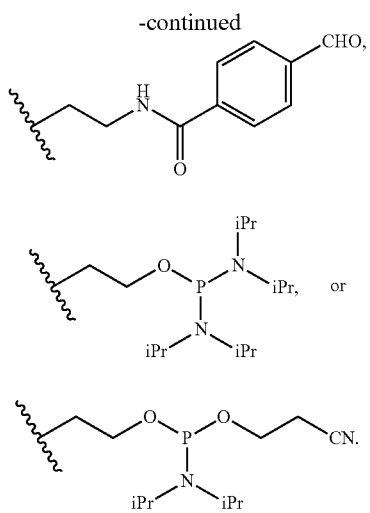

In one embodiment, in any one of the formulae provided herein, including Formulae I to XX, XVa to XVb, XVIa to XVIg, XIXa to XIXc, and XXa to XXc, p is an integer from 1 to 20. In another embodiment, in any one of the formulae provided herein, including Formulae I to XX, XVa to XVb, XVIa to XVIg, XIXa to XIXc, and XXa to XXc, p is an integer of 1, 2, 3, 4, 5, 6, 7, 8, 9, or 10. In yet another embodiment, in any one of the formulae provided herein, including Formulae I to XX, XVa to XVb, XVIa to XVIg, XIXa to XIXc, and XXa to XXc, p is an integer of 5, 10, 15, 20, 25, 30, 35, 40, 45, or 50.

$L^6$ is $C_{1-10}$ alkylene, optionally substituted with one or more substituents Q. In another embodiment, in any one of the formulae provided herein, including Formulae I to XX, XVa to XVb, XVIa to XVIg, XIXa to XIXc, and XXa to XXc, $L^6$ is methylene, ethylene, propylene, butylenes, pentylene, or hexylene, each of which is optionally substituted with one or more substituents Q. In yet another embodiment, in any one of the formulae provided herein, including Formulae I to XX, XVa to XVb, XVIa to XVIg, XIXa to XIXc, and XXa to XXc, $L^6$ is methylene, 1,2-ethylene, 1,3-propylene, 1,4-butylenes, 1,5-pentylene, or 1,6-hexylene, each optionally substituted with one or more substituents Q. In still another embodiment, in any one of the formulae provided herein, including Formulae I to XX, XVa to XVb, XVIa to XVIg, XIXa to XIXc, and XXa to XXc, $L^6$ is methylene, 1,2-ethylene, or 1,3-propylene.

In one embodiment, in any one of the formulae provided herein, including Formulae I to XX, XVa to XVb, XVIa to XVIg, XIXa to XIXc, and XXa to XXc, $L^6$ is $C_{1-10}$ alkylene, optionally substituted with one or more substituents Q. In another embodiment, in any one of the formulae provided herein, including Formulae I to XX, XVa to XVb, XVIa to XVIg, XIXa to XIXc, and XXa to XXc, $L^6$ is methylene, ethylene, propylene, butylenes, pentylene, or hexylene, each of which is optionally substituted with one or more substituents Q. In yet another embodiment, in any one of the formulae provided herein, including Formulae I to XX, XVa to XVb, XVIa to XVIg, XIXa to XIXc, and XXa to XXc, $L^6$ is methylene, 1,2-ethylene, 1,3-propylene, 1,4-butylenes, 1,5-pentylene, or 1,6-hexylene, each optionally substituted with one or more substituents Q. In still another embodiment, in any one of the formulae provided herein, including Formulae I to XX, XVa to XVb, XVIa to XVIg, XIXa to XIXc, and XXa to XXc, $L^6$ is methylene, 1,2-ethylene, or 1,3-propylene.

In one embodiment, in any one of the formulae provided herein, including Formulae I to XX, XVa to XVb, XVIa to XVIg, XIXa to XIXc, and XXa to XXc, $L^6$ is $C_{1-10}$ heteroalkylene, optionally substituted with one or more substituents Q. In another embodiment, in any one of the formulae provided herein, including Formulae I to XX, XVa to XVb, XVIa to XVIg, XIXa to XIXc, and XXa to XXc, $L^6$ is —(CH$_2$)$_2$O—, —(CH$_2$)$_2$OCH$_2$—, —CH$_2$NH—, —CH$_2$NHCH$_2$—, —(CH$_2$)$_2$NG—, —(CH$_2$)$_2$NHC(O)—, —(CH$_2$)$_2$NHC(O)CH$_2$—, —(CH$_{22}$NHC(O)(CH$_2$)$_2$—, —(CH$_2$)$_2$NHC(O)(CH$_2$)$_3$—, —(CH$_2$)$_2$NHC(O)(CH$_2$)$_5$—, —(CH$_2$)$_6$NHC(O)(CH$_2$)$_2$—, —(CH$_2$)$_2$NHC(O)(CH$_2$)$_2$C(O)—, —(CH$_2$)$_2$NHC(O)(CH$_{24}$C(O)—, —(CH$_2$)$_2$C(O)NH(CH$_2$)$_2$C(O)—, —(CH$_2$)$_2$C(O)NH(CH$_2$)$_4$C(O)—, —(CH$_2$)$_2$NHC(O)CH(SO$_3$H)CH$_2$NHC(O)(CH$_2$)$_2$C(O)—, —(CH$_2$)$_2$C(O)NH(CH$_2$)$_3$—, or —(CH$_2$)$_2$C(O)NH(CH$_2$)$_4$CH$_2$—.

In one embodiment, in any one of the formulae provided herein, including Formulae I to XX, XVa to XVb, XVIa to XVIg, XIXa to XIXc, and XXa to XXc, $L^6$ is $C_{1-10}$ heteroalkylene-$C_{3-15}$ cycloalkylene, where the heteroalkylene and cycloalkylene are each independently and optionally substituted with one or more substituents Q.

In one embodiment, in any one of the formulae provided herein, including Formulae I to XX, XVa to XVb, XVIa to XVIg, XIXa to XIXc, and XXa to XXc, $Z^6$ is hydrogen. In another embodiment, in any one of the formulae provided herein, including Formulae I to XX, XVa to XVb, XVIa to XVIg, XIXa to XIXc, and XXa to XXc, $Z^6$ is $C_{1-10}$ alkyl, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^6$ is methyl. In yet another embodiment, in any one of the formulae provided herein, including Formulae I to XX, XVa to XVb, XVIa to XVIg, XIXa to XIXc, and XXa to XXc, $Z^6$ is —C(O)$R^{1a}$, wherein $R^{1a}$ is as defined herein. In yet another embodiment, in any one of the formulae provided herein, including Formulae I to XX, XVa to XVb, XVIa to XVIg, XIXa to XIXc, and XXa to XXc, $Z^6$ is —C(O)CH$_3$. In yet another embodiment, in any one of the formulae provided herein, including Formulae I to XX, XVa to XVb, XVIa to XVIg, XIXa to XIXc, and XXa to XXc, $Z^6$ is C(O)O$R^{1a}$, wherein $R^{1a}$ is as defined herein. In yet another embodiment, in any one of the formulae provided herein, including Formulae I to XX, XVa to XVb, XVIa to XVIg, XIXa to XIXc, and XXa to XXc, $Z^6$ is —C(O)OH or C(O)OtBU. In yet another embodiment, in any one of the formulae provided herein, including Formulae I to XX, XVa to XVb, XVIa to XVIg, XIXa to XIXc, and XXa to XXc, $Z^6$ is —C(O)N$R^{1b}R^{1c}$, wherein $R^{1b}$ and $R^{1c}$ are each as defined herein. In yet another embodiment, in any one of the formulae provided herein, including Formulae I to XX, XVa to XVb, XVIa to XVIg, XIXa to XIXc, and XXa to XXc, $Z^6$ is —C(O)NH$_2$. In yet another embodiment, in any one of the formulae provided herein, including Formulae I to XX, XVa to XVb, XVIa to XVIg, XIXa to XIXc, and XXa to XXc, $Z^6$ is —NR$_{1b}$R$^{1c}$, wherein $R^{1b}$ and $R^{1c}$ are each as defined herein. In yet another embodiment, in any one of the formulae provided herein, including Formulae I to XX, XVa to XVb, XVIa to XVIg, XIXa to XIXc, and XXa to XXc, $Z^6$ is —NHCH$_3$. In yet another embodiment, in any one of the formulae provided herein, including Formulae I to XX, XVa to XVb, XVIa to XVIg, XIXa to XIXc, and XXa to XXc, $Z^6$ is —NR$^{1a}$C(O)$R^{1d}$, wherein $R^{1b}$ and $R^{1c}$ are each as defined herein. In still another embodiment, in any one of the formulae provided herein, including Formulae I to XX, XVa to XVb, XVIa to XVIg, XIXa to XIXc, and XXa to XXc, $Z^6$ is —NHBoc.

In one embodiment, in any one of the formulae provided herein, including Formulae I to XX, XVa to XVb, XVIa to XVIg, XIXa to XIXc, and XXa to XXc, $Z^6$ is $C_{2-6}$ alkynyl, optionally substituted with one or more substituents Q. In another embodiment, in any one of the formulae provided herein, including Formulae I to XX, XVa to XVb, XVIa to XVIg, XIXa to XIXc, and XXa to XXc, $Z^6$ is heterocyclyl containing a carbon-carbon triple, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^6$ is $C_{2-6}$ alkynyloxy, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^6$ is $C_{3-15}$ cycloalkyloxy containing a carbon-carbon triple, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^6$ is $C_{6-20}$ aryloxy containing a carbon-carbon triple, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^6$ is heterocyclyloxy containing a carbon-carbon triple, optionally substituted with one or more substituents Q. In yet another embodiment, in any one of the formulae provided herein, including Formulae I to XX, XVa to XVb, XVIa to XVIg, XIXa to XIXc, and XXa to XXc, $Z^6$ is —OP(OR$^{1a}$)(NR$^{1b}$R$^{1c}$), wherein R$^{1a}$, R$^{1b}$, and R$^{1c}$ are each as defined herein. In yet another embodiment, in any one of the formulae provided herein, including Formulae I to XX, XVa to XVb, XVIa to XVIg, XIXa to XIXc, and XXa to XXc, $Z^6$ is —OP((NR$^{1b}$R$^{1c}$)$_2$, wherein R$^{1b}$ and R$^{1c}$ are each as defined herein. In yet another embodiment, in any one of the formulae provided herein, including Formulae I to XX, XVa to XVb, XVIa to XVIg, XIXa to XIXc, and XXa to XXc, $Z^6$ is —OS(O)$_2$R$^{1a}$, wherein R$^{1a}$ is as defined herein. In still another embodiment, in any one of the formulae provided herein, including Formulae I to XX, XVa to XVb, XVIa to XVIg, XIXa to XIXc, and XXa to XXc, $Z^6$ is SSR$^{1a}$, wherein R$^{1a}$ is as defined herein.

In one embodiment, in any one of the formulae provided herein, including Formulae I to XX, XVa to XVb, XVIa to XVIg, XIXa to XIXc, and XXa to XXc, $Z^6$ is:

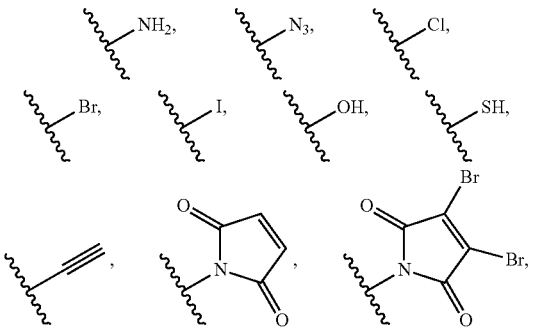

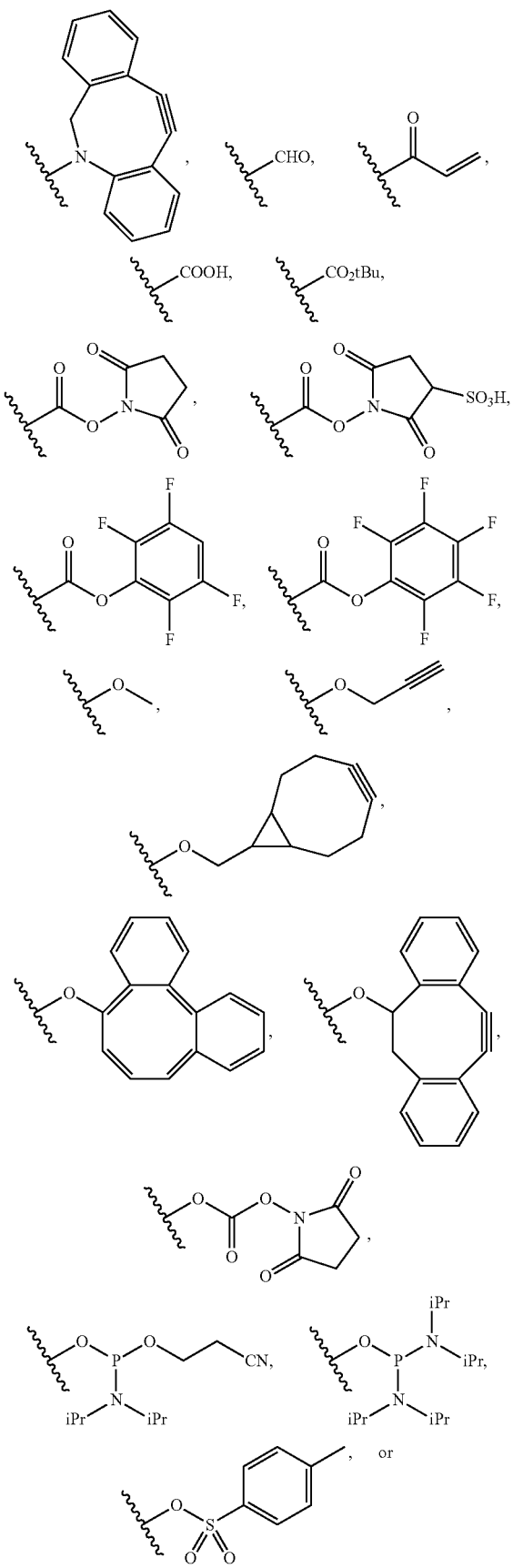

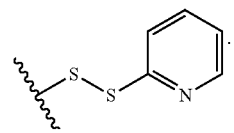
In another embodiment, in any one of the formulae provided herein, including Formulae I to XX, XVa to XVb, XVIa to XVIg, XIXa to XIXc, and XXa to XXc, $L^6$-$Z^6$ is:
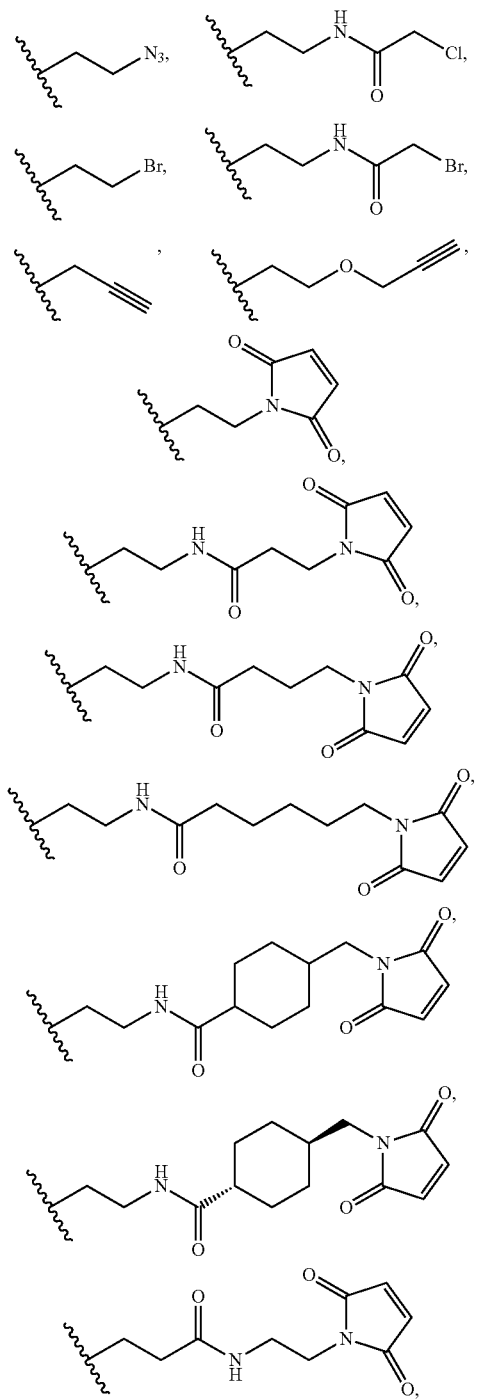
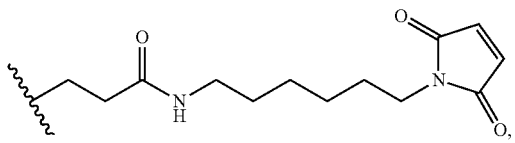
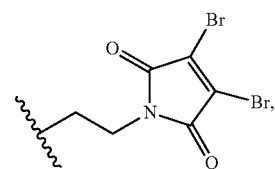
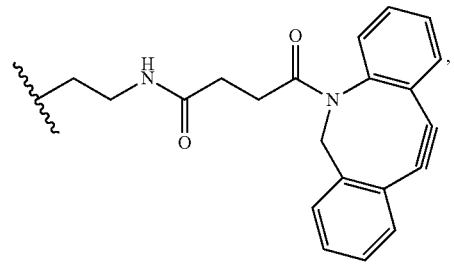
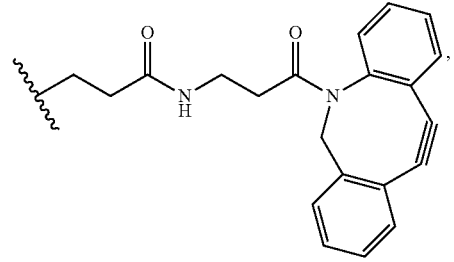
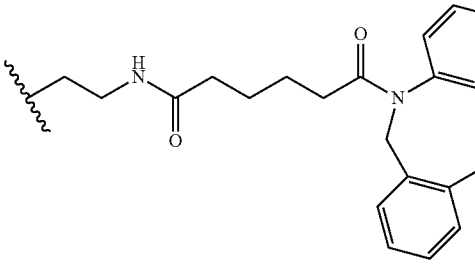
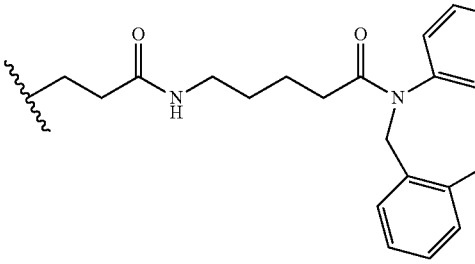
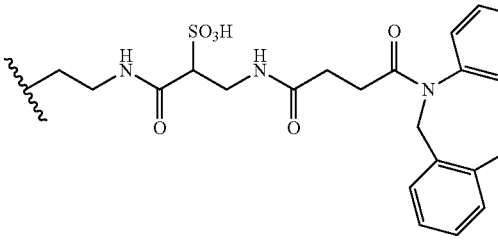

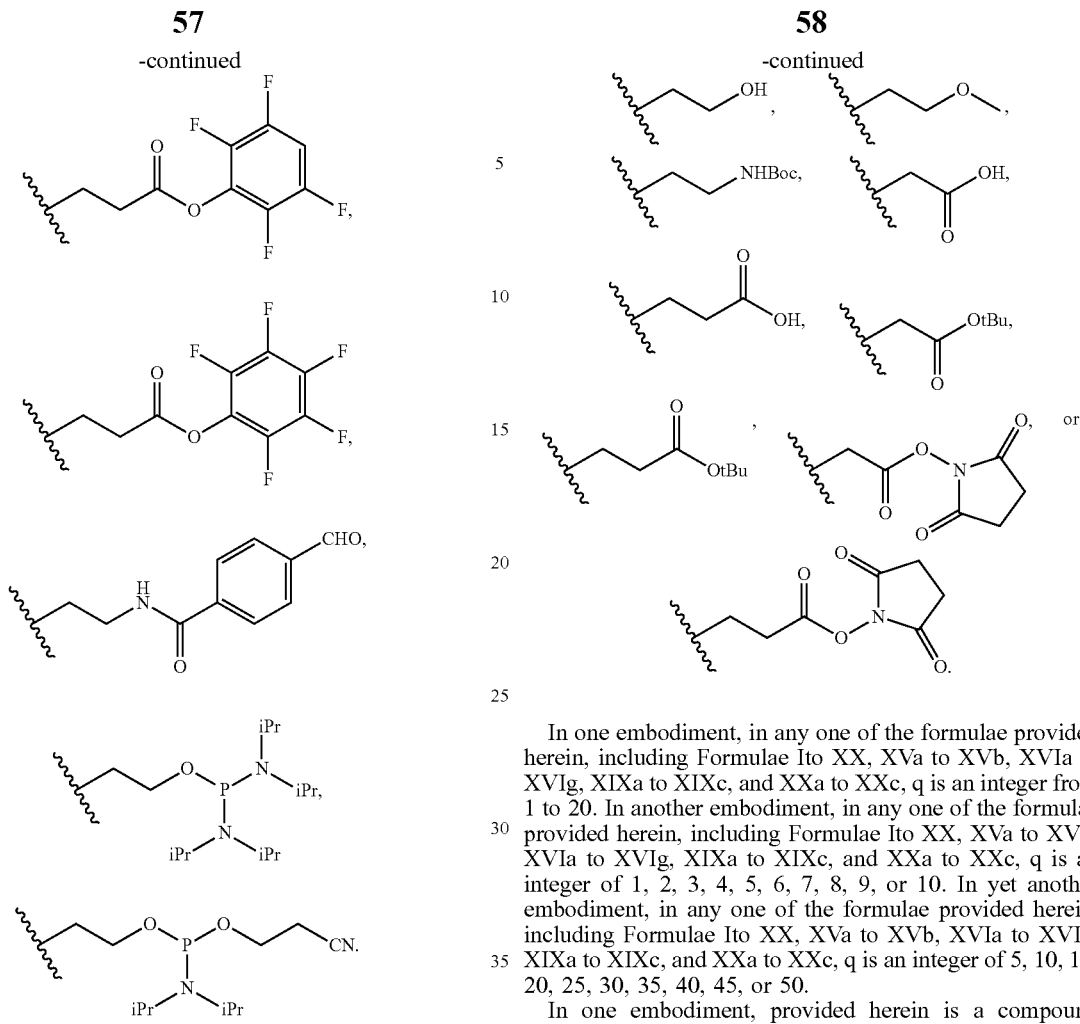

In one embodiment, in any one of the formulae provided herein, including Formulae I to XX, XVa to XVb, XVIa to XVIg, XIXa to XIXc, and XXa to XXc, q is an integer from 1 to 20. In another embodiment, in any one of the formulae provided herein, including Formulae I to XX, XVa to XVb, XVIa to XVIg, XIXa to XIXc, and XXa to XXc, q is an integer of 1, 2, 3, 4, 5, 6, 7, 8, 9, or 10. In yet another embodiment, in any one of the formulae provided herein, including Formulae I to XX, XVa to XVb, XVIa to XVIg, XIXa to XIXc, and XXa to XXc, q is an integer of 5, 10, 15, 20, 25, 30, 35, 40, 45, or 50.

In one embodiment, provided herein is a compound selected from:

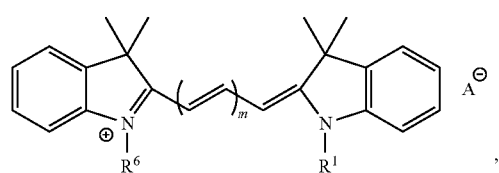

A

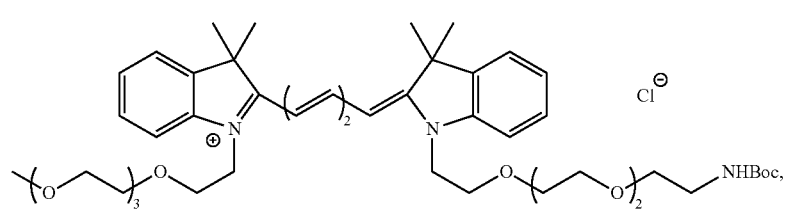

A1

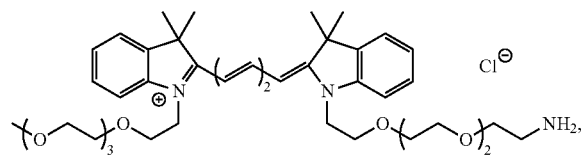

A2

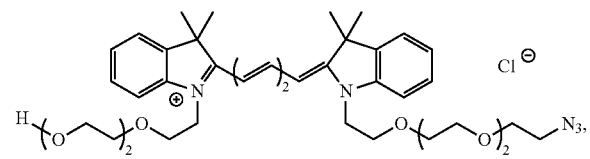

A3

-continued
A4
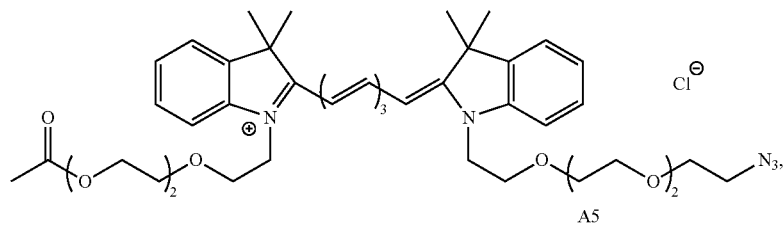
A5
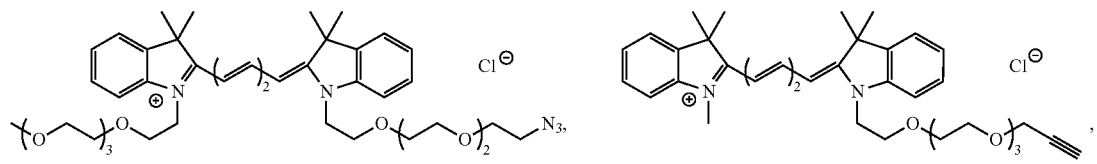
A6
A7
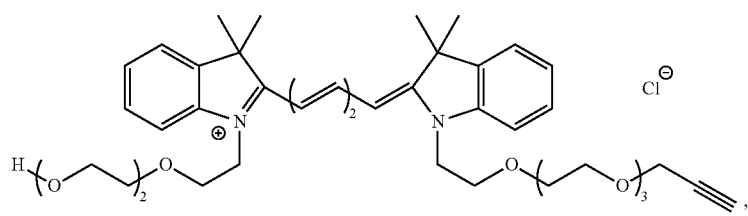
A8
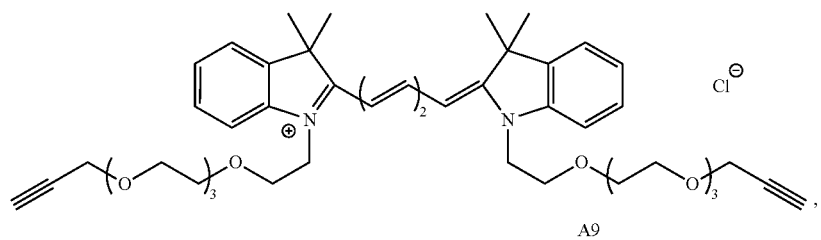
A9
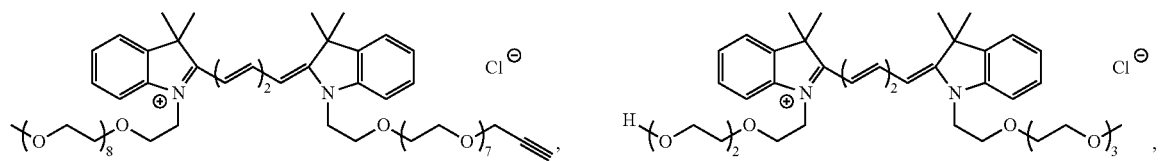
A10
A11
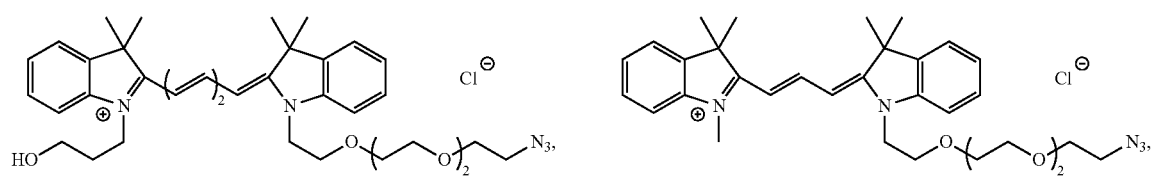
A12
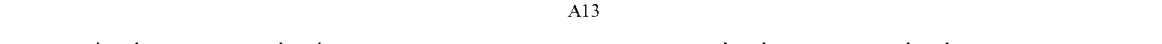
A13
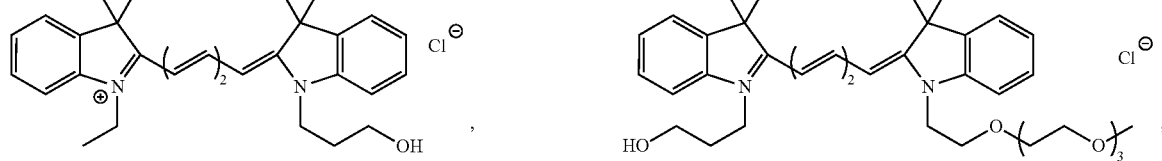
A14
A15
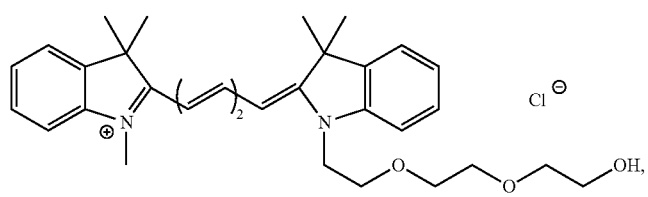

-continued
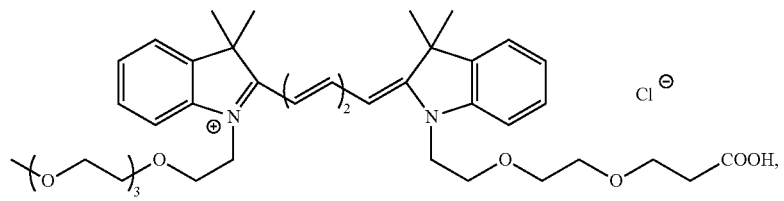
A16
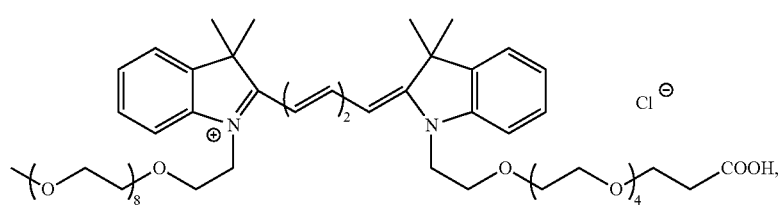
A17
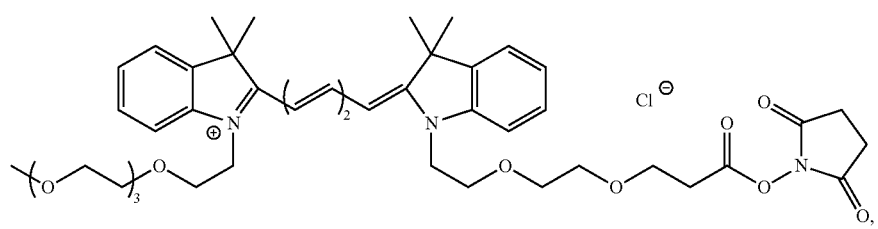
A18
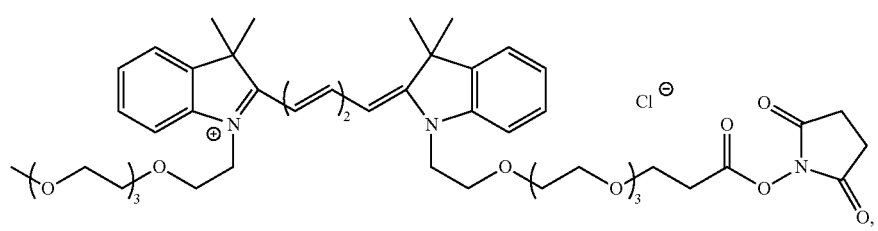
A19
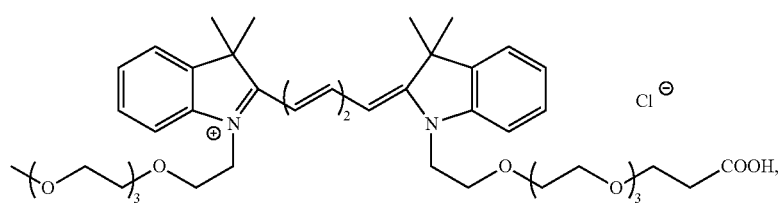
A20
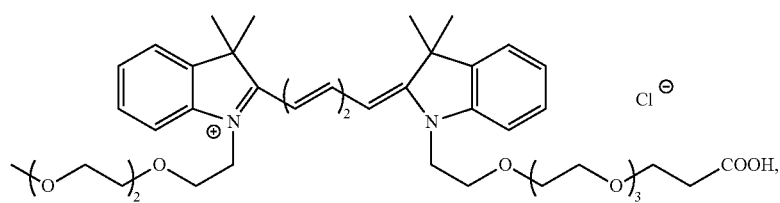
A21
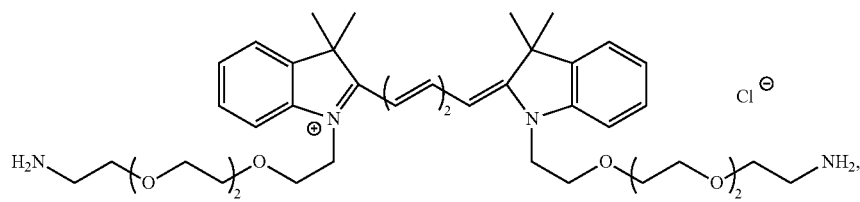
A22

-continued
A23
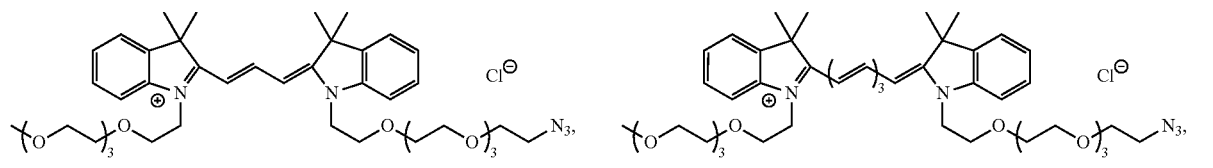
A24
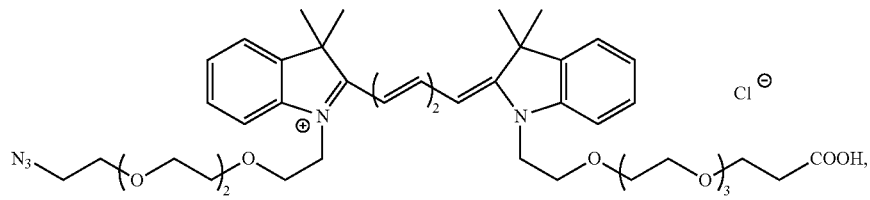
A25
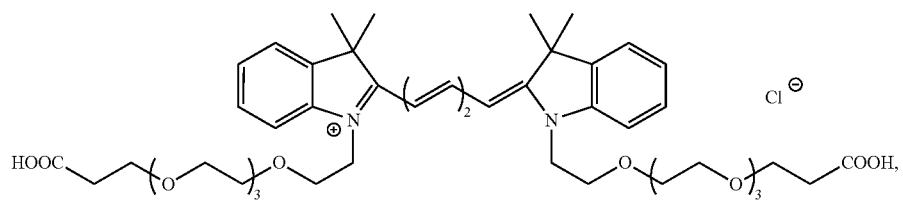
A26
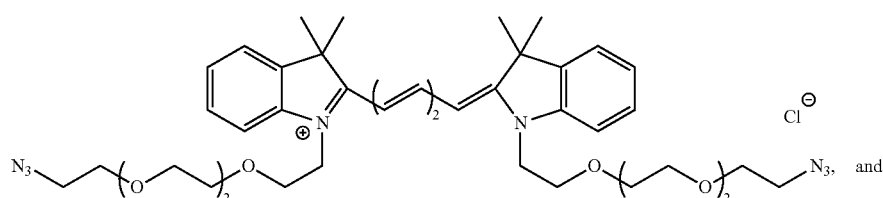
A27
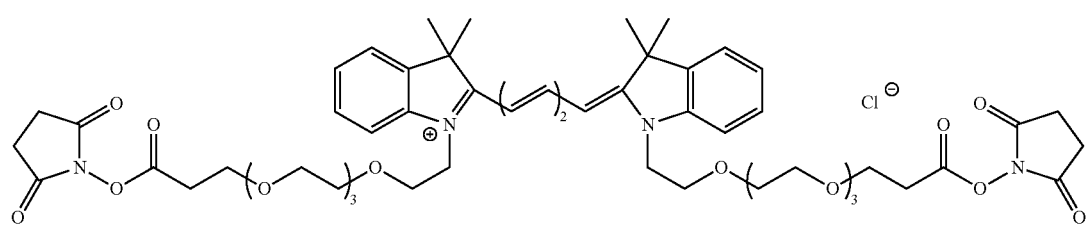
and tautomers and mixtures of two or more tautomers thereof; and pharmaceutically acceptable solvates and hydrates thereof.
In yet another embodiment, provided herein is a compound selected from:
B
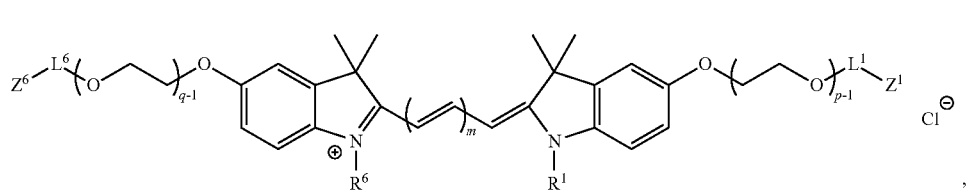
B1
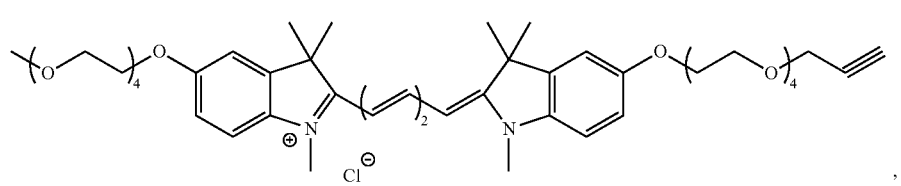

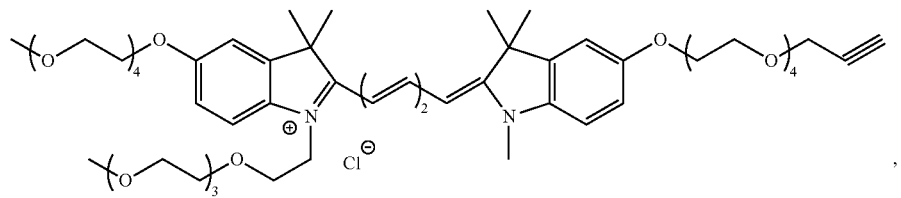
B2
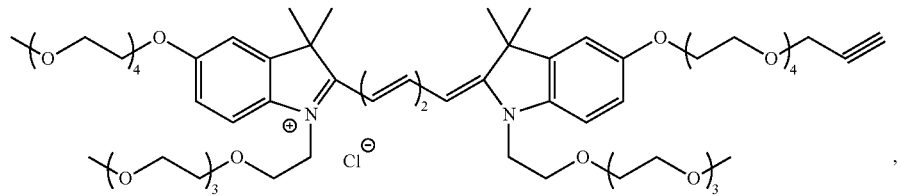
B3
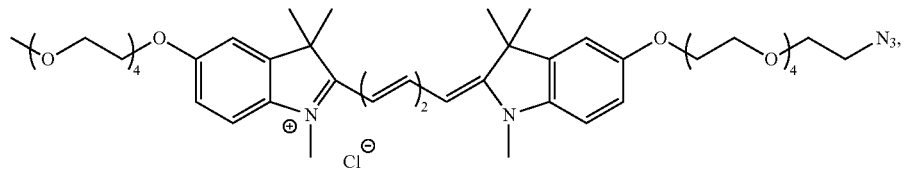
B4
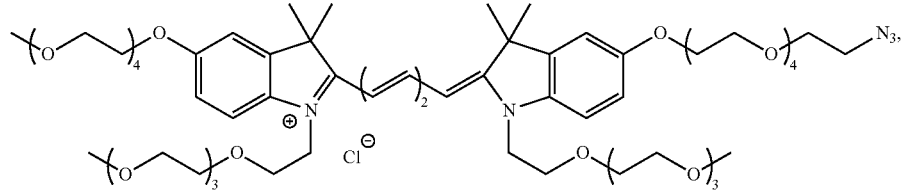
B5
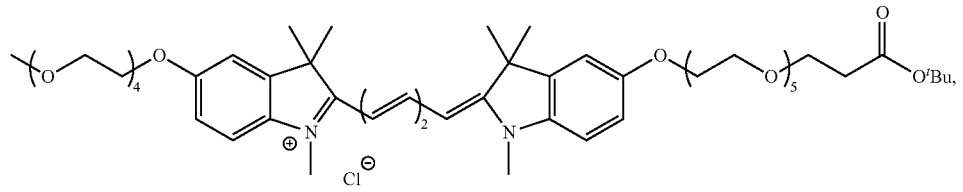
B6
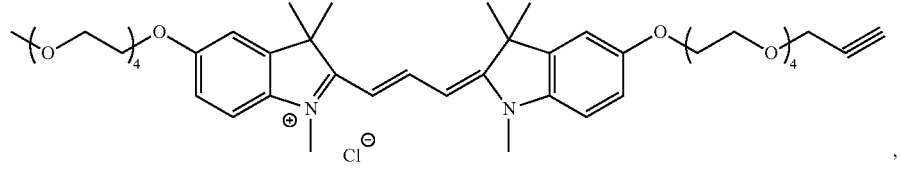
B7
, and
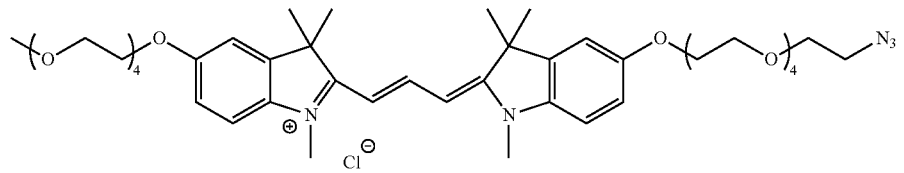
B8
and tautomers and mixtures of two or more tautomers thereof; and pharmaceutically acceptable solvates and hydrates thereof.
In yet another embodiment, provided herein is a compound selected from:

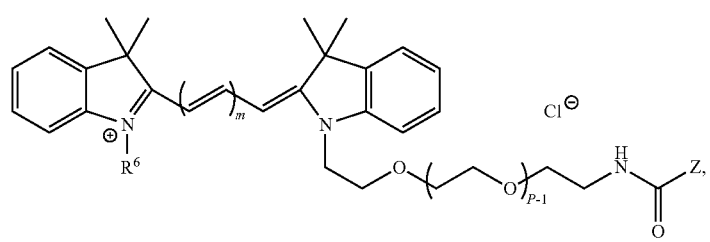
C
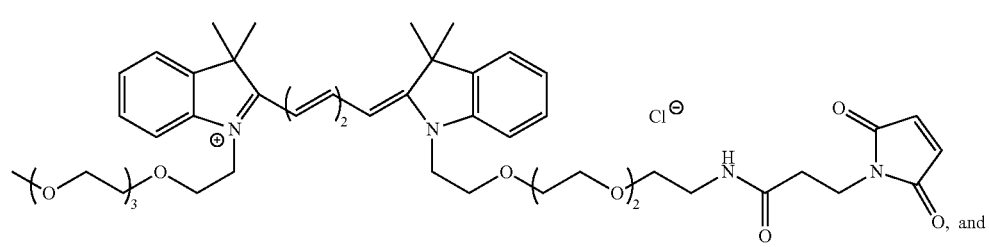
C1
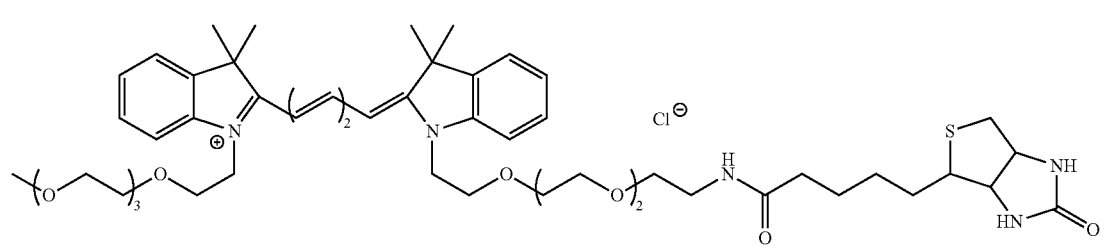
C2
and tautomers and mixtures of two or more tautomers thereof; and pharmaceutically acceptable solvates and hydrates thereof.
In yet another embodiment, provided herein is a compound selected from:
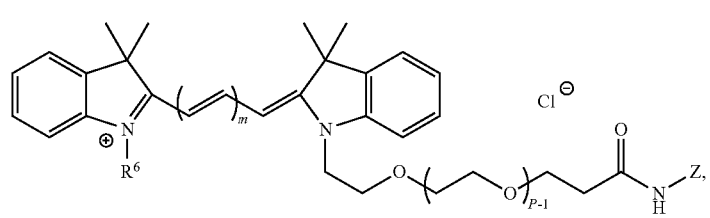
D
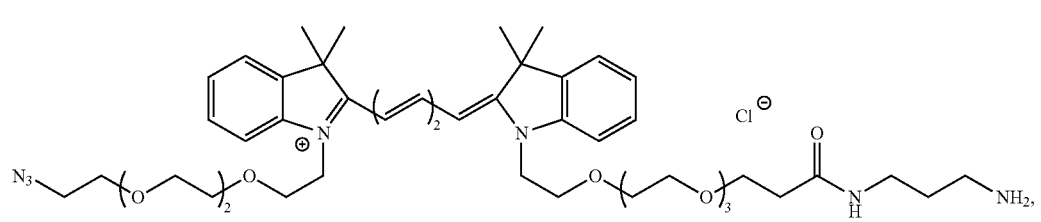
D1
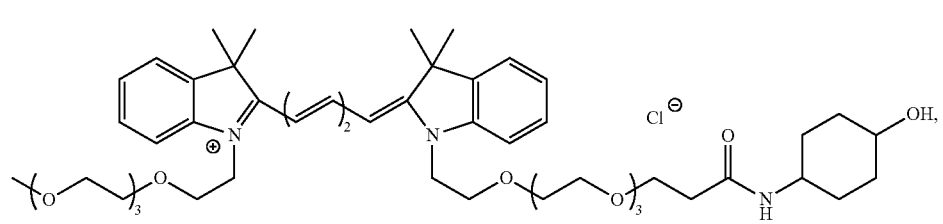
D2

-continued

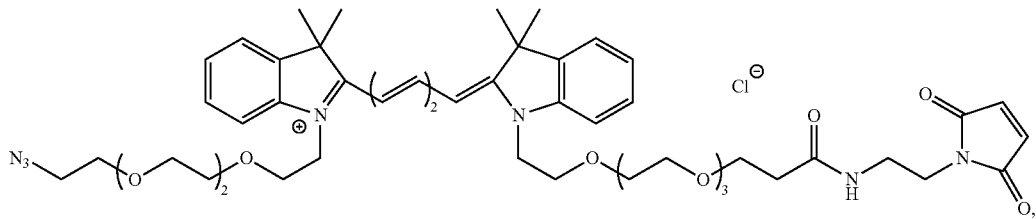

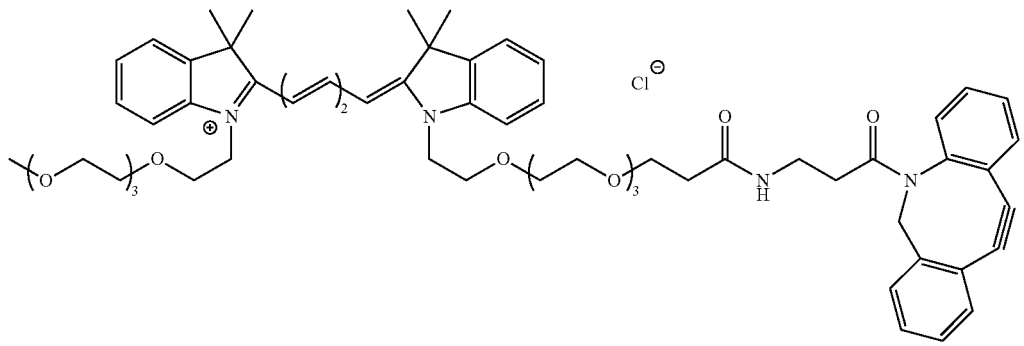

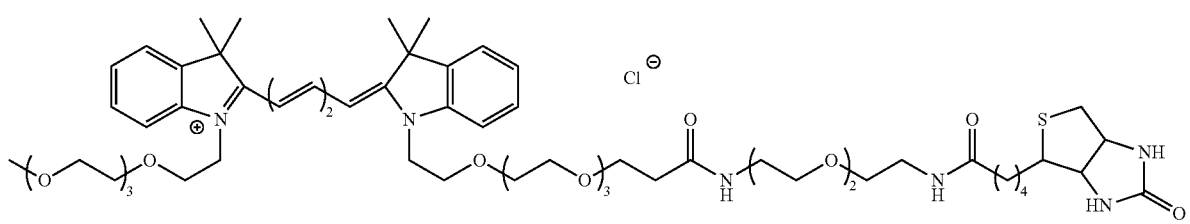

and tautomers and mixtures of two or more tautomers thereof; and pharmaceutically acceptable solvates and hydrates thereof.

In yet another embodiment, provided herein is a compound selected from:

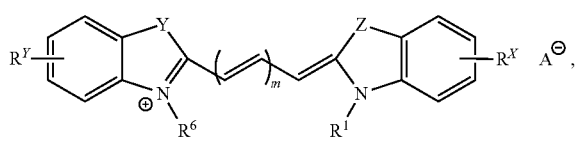

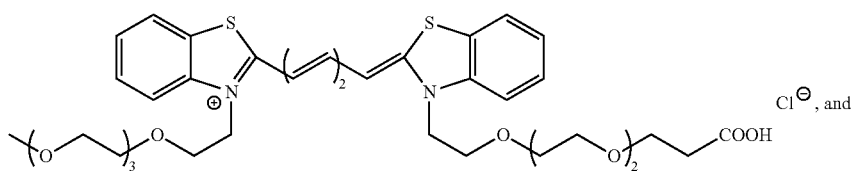

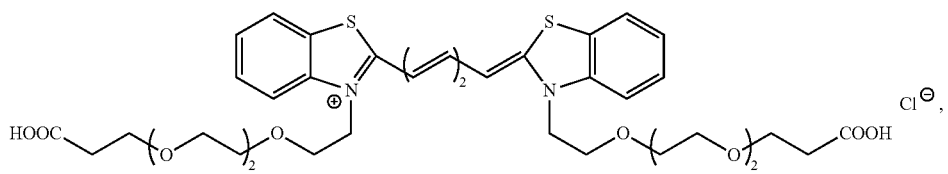

and tautomers and mixtures of two or more tautomers thereof; and pharmaceutically acceptable solvates and hydrates thereof.

In yet another embodiment, provided herein is a compound selected from:

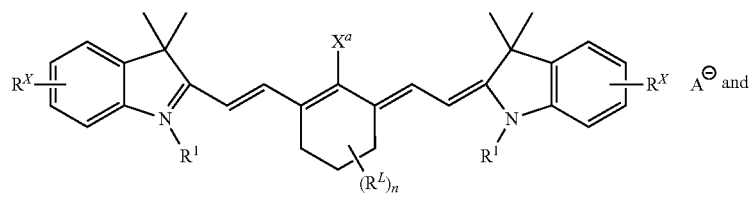

F

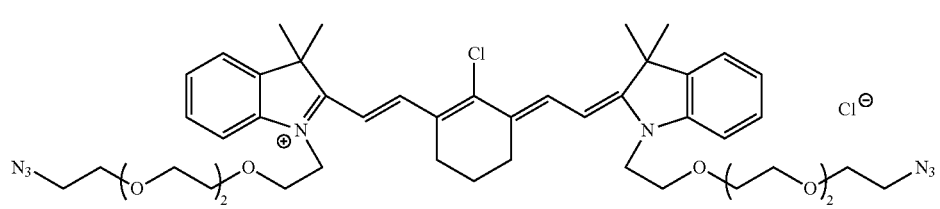

F1 and tautomers and mixtures of two or more tautomers thereof; and pharmaceutically acceptable solvates and hydrates thereof.

In yet another embodiment, provided herein is a compound selected from:

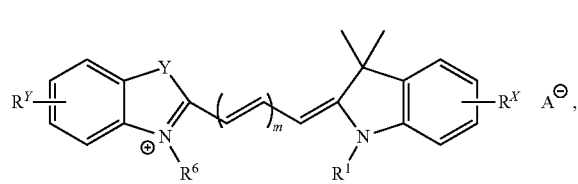

G

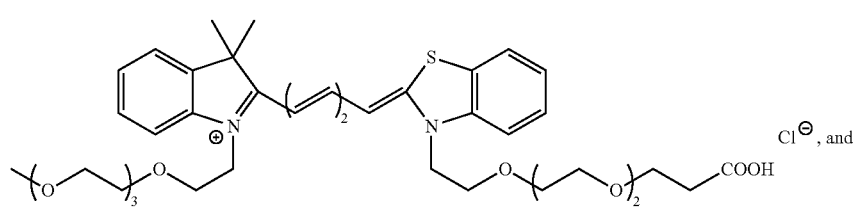

G1

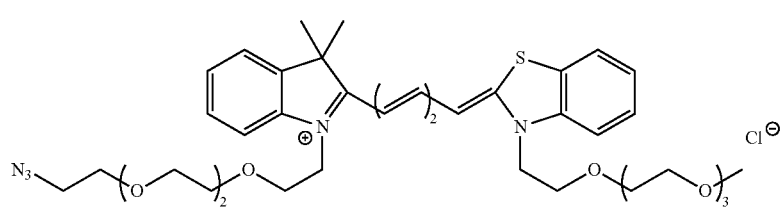

G2 and tautomers and mixtures of two or more tautomers thereof; and pharmaceutically acceptable solvates and hydrates thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

For example, the compound of Formula II may exist in at least two tautomeric forms as shown below:

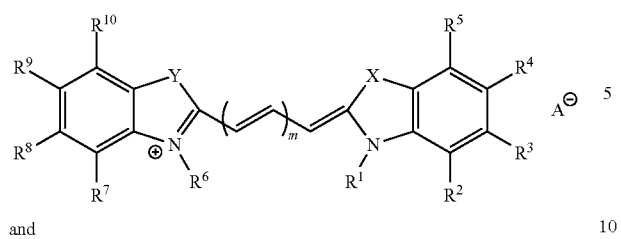

and

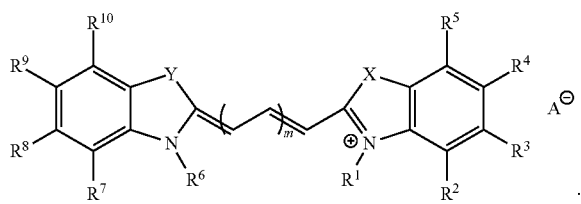

Methods of Synthesis

The compounds provided herein can be prepared, isolated, or obtained by any method known to one of skill in the art. In certain embodiments, for an example, a compound of Formula II can be prepared as shown in Scheme 1, where $L^s$ is a leaving group, e.g., chloro, bromo, iodo, triflate, or tosylate; and $R^1$, $R^2$, $R^3$, $R^4$, $R^5$, $R^6$, $R^7$, $R^8$, $R^9$, $R^{10}$, A, X, Y, and m are each as defined herein.

Scheme 1

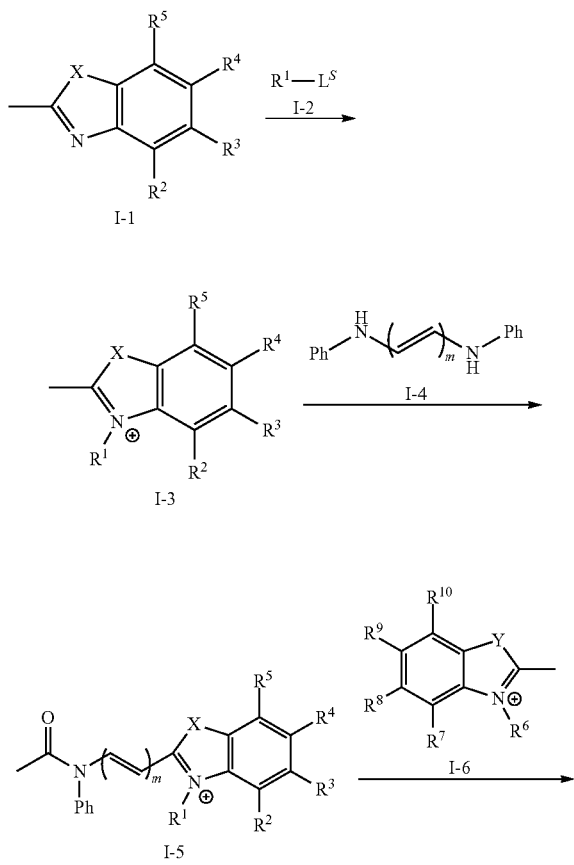

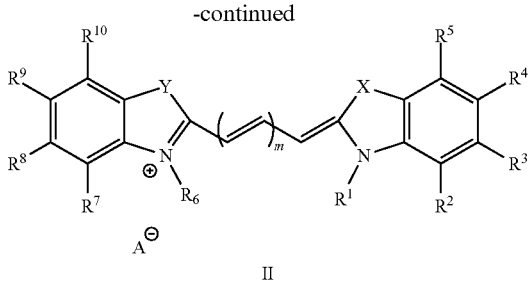

II

Compound I-1 is alkylated with compound I-2 to form compound I-3. Compound I-6 is prepared similarly. Subsequently, compound I-3 is treated with compound I-4 to form compound I-5, which is then treated with compound I-6 to form a compound of Formula II.

A compound of Formula I can also be prepared as described in U.S. Pat. No. 5,627,027, the disclosure of which is incorporated herein by reference in its entirety.

The starting materials used in the synthesis of the compounds provided herein are either commercially available or can be readily prepared. For example, indolenine compounds can be prepared according to the methods described in U.S. Pat. No. 5,627,027.

Pharmaceutical Compositions

In one embodiment, provided herein is a pharmaceutical composition comprising a compound provided herein, e.g., a compound of Formula I, or a tautomer or a mixture of two or more tautomers thereof; or a pharmaceutically acceptable solvate or hydrate thereof; and a pharmaceutically acceptable excipient.

The pharmaceutical composition that comprises a compound provided herein, e.g., a compound of Formula I, or a tautomer or a mixture of two or more tautomers thereof; or a pharmaceutically acceptable solvate or hydrate thereof, can be formulated in various dosage forms for oral, parenteral, and topical administration. The pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

In one embodiment, the pharmaceutical composition is provided in a dosage form for oral administration, which comprises a compound provided herein, e.g., a compound of Formula I, or a tautomer or a mixture of two or more tautomers thereof; or a pharmaceutically acceptable solvate or hydrate thereof.

In another embodiment, the pharmaceutical composition is provided in a dosage form for parenteral administration, which comprises a compound provided herein, e.g., a compound of Formula I, or a tautomer or a mixture of two or more tautomers thereof; or a pharmaceutically acceptable solvate or hydrate thereof In yet another embodiment, the pharmaceutical composition is provided in a dosage form for topical administration, which comprises a compound provided herein, e.g., a compound of Formula I, or a tautomer or a mixture of two or more tautomers thereof; or a pharmaceutically acceptable solvate or hydrate thereof.

A. Oral Administration

The pharmaceutical composition provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical composition can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical composition provided herein varies upon the type of formulation, and is readily discernible to those of ordinary skill in the art. The binder or filler may be present from about 50 to about 99% by weight in the pharmaceutical composition provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical composition provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical composition provided herein varies upon the type of formulation, and is readily discernible to those of ordinary skill in the art. The amount of a disintegrant in the pharmaceutical composition provided herein varies upon the type of formulation, and is readily discernible to those of ordinary skill in the art. The pharmaceutical composition provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical composition provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical composition provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical composition provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical composition provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical composition provided herein for oral administration can be also provided in the forms of liposomes, micelles, microspheres, or nanosystems. Micellar dosage forms can be prepared as described in U.S. Pat. No. 6,350,458.

The pharmaceutical composition provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical composition provided herein for oral administration can be formulated as immediate or modified release dosage forms, including delayed-, sustained, pulsed-, controlled, targeted-, and programmed-release forms.

B. Parenteral Administration

The pharmaceutical composition provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical composition provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical composition intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical composition provided herein is formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical composition for parenteral administration is provided as ready-to-use sterile solutions. In another embodiment, the pharmaceutical composition is provided as sterile dry soluble products, including lyophilized powders and hypodermic tablets, to be reconstituted with a vehicle prior to use. In yet another embodiment, the pharmaceutical composition is provided as ready-to-use sterile suspensions. In yet another embodiment, the pharmaceutical composition is provided as sterile dry insoluble products to be reconstituted with a vehicle prior to use. In still another embodiment, the pharmaceutical composition is provided as ready-to-use sterile emulsions.

The pharmaceutical composition provided herein for parenteral administration can be formulated as immediate or modified release dosage forms, including delayed-, sustained, pulsed-, controlled, targeted-, and programmed-release forms.

The pharmaceutical composition provided herein for parenteral administration can be formulated as a suspension, solid, semi-solid, or thixotropic liquid, for administration as an implanted depot. In one embodiment, the pharmaceutical composition provided herein is dispersed in a solid inner matrix, which is surrounded by an outer polymeric membrane that is insoluble in body fluids but allows the active ingredient in the pharmaceutical composition diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical composition provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical composition provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical composition provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical composition can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical composition provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical composition provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: *The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical composition provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid;. Combinations of the various vehicles can also be used. Rectal and vaginal suppositories may be prepared by compressing or molding. The typical weight of a rectal and vaginal suppository is about 2 to about 3 g.

The pharmaceutical composition provided herein can be administered ophthalmically in the forms of solutions, suspensions, ointments, emulsions, gel-forming solutions, powders for solutions, gels, ocular inserts, and implants.

The pharmaceutical composition provided herein can be administered intranasally or by inhalation to the respiratory tract. The pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical composition can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical composition provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical composition provided herein for inhaled/intranasal administration can further comprise a suitable flavor, such as menthol and levomenthol; and/or sweeteners, such as saccharin and saccharin sodium.

The pharmaceutical composition provided herein for topical administration can be formulated to be immediate release or modified release, including delayed-, sustained-, pulsed-, controlled-, targeted, and programmed release.

D. Modified Release

The pharmaceutical composition provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical composition in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, 2nd ed.; Rathbone et al., Eds.; Marcel Dekker AG: 2005; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS PharmSciTech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical composition provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol 2.

In certain embodiments, the pharmaceutical composition provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUIDRAGIT®, Rohm America, Inc., Piscataway, NJ); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical composition provided herein is formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the pharmaceutical composition.

The pharmaceutical composition provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical composition provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical composition in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the pharmaceutical composition provided herein is formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Pat. Appl. Publ. No. WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical composition provided herein is formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical composition provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet-and dry-granulation, extrusion/spheronization, roller-compaction, melt-congealing, and by spray-coating seed cores. See, for example, *Multiparticulate Oral Drug Delivery*; Ghebre-Sellassie Ed.; Marcel Dekker: 1994; and *Pharmaceutical Pelletization Technology*; Ghebre-Sellassie Ed.; Marcel Dekker: 1989.

Other excipients or carriers as described herein can be blended with the pharmaceutical composition to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical composition provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Methods of Use

In one embodiment, provided herein is a method of labeling a biomolecule, comprising the step of contacting the biomolecule with a compound disclosed herein, e.g., a compound of Formula I, or a tautomer or a mixture of two or more tautomers thereof; or a pharmaceutically acceptable solvate or hydrate thereof The biomolecule thus labeled is suitable for biological imaging and clinical diagnosis.

In one embodiment, the contacting step is performed at a pH ranging from about 5 to about 9 or from about 6 to about 8. In another embodiment, the contacting step is performed at a pH of about 6, about 6.2, about 6.4, about 6.6, about 6.8, about 7, about 7.2, about 7.4, about 7.6, about 7.8, or about 8.

In one embodiment, the contacting step is performed at a temperature ranging from about 0 to about 50° C., from about 10 to about 40° C., from about 20 to 40° C., or from about 30 to about 40° C. In another embodiment, the contacting step is performed at a temperature ranging from about 35 to about 40° C.

In one embodiment, the contacting step is performed at an aqueous solution.

In one embodiment, the contacting step is performed under physiological conditions.

In one embodiment, the biomolecule is an amino acid based compound. In another embodiment, the biomolecule is a protein. In another embodiment, the biomolecule is an antibody. In another embodiment, the biomolecule is an antibody drug conjugate. In yet another embodiment, the biomolecule is an antigen. In still another embodiment, the biomolecule is a polypeptide.

The amino acid based comound can be attached to the compositions disclosed herein via the amine, amino, carboxylic acid, or sulfhydryl group.

The biomolecule thus labeled is suitable for biological imaging, drug delivery, clinical diagnosis, forensics, in vitro diagnostics, and in vivo diagnostics. Non-limiting applications include drug delivery, immunotherapy, imaging contrast medium or agent, flow cytometry, cell sorting, microscopy, in situ hybridization, immune histochemistry, enzyme-linked immunosorbent assays (ELISA), Western blot, immunoprecipitation, microarrays, etc.

In one embodiment, the biomolecule is a nucleic acid based compound. In another embodiment, the biomolecule is a polynucleotide. In another embodiment, the biomolecule is a deoxyribonucleic acid. In another embodiment, the biomolecule is a ribonucleic acid. In another embodiment, the biomolecule is a protein nucleic acid. In another embodiment, the biomolecule is an aptamer.

The nucleic acid base (e.g. deoxyribonucleic acid, ribonucleic acid, chimeric nucleic acid, etc.) compounds can be attached to the compositions disclosed herein via the phosphate attached to the 5' carbon on the ribose or any available amine, methyl, or oxide group on the base. In some embodiments, the PEG may function as a linker to allow the labeled nucleic acid to be incorporated into a sequence.

The biomolecule thus labeled is suitable for biological imaging, clinical diagnosis, drug delivery, forensics, and in vitro diagnostics. Non-limiting applications inclue amplification (polymerase chain reaction, transcription mediated amplification, strand displacement, loop-mediated isothermal amplification, rolling circle amplification, ligase chain reaction, nucleic acid sequence based amplification, multiple displacement amplification, helicase dependant amplification, ramification amplification, etc.), real time amplification, sequencing (sanger, real-time, ion semiconductor, synthesis, ligation, nanopore, etc.), detection probes, fluorescent in situ hybridization, antisense technology, microarrays, etc.

Kits

In one embodiment, provided herein is a kit which, which includes a container and a dosage form of a compound provided herein, e.g., a compound of Formula I, or a tautomer or a mixture of two or more tautomers thereof; or a pharmaceutically acceptable solvate or hydrate thereof.

The kit provided herein can further include a device that is used to administer the compound provided herein. Examples of such devices include, but are not limited to, syringes, needle-less injectors drip bags, patches, and inhalers.

The kit provided herein can further include a pharmaceutically acceptable vehicle that can be used to administer one or more the compound provided herein. For example, if the compound provided herein is provided in a solid form that must be reconstituted for parenteral administration, the kit can comprise a sealed container of a suitable vehicle in which the compound can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

In another embodiment is a kit for diagnostics or research use. Included in theses kits is a biomolecule labeled with a compound disclosed herein, e.g., a compound of Formula I, or a tautomer or a mixture of two or more tautomers thereof; or a pharmaceutically acceptable solvate or hydrate thereof.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); CD$_3$OD (deuterated methanol); THF (tetrahydrofuran); CDCl$_3$ (deuterated chloroform); DMSO (dimethylsulfoxide); DMSO-d$_6$ (deuterated dimethylsulfoxide); EtOAc (ethyl acetate); MeOH (methanol); δ (chemical shifts in ppm); J (coupling constants in Hz); multiplicities: s (singlet); d (doublet) t (triplet); m (multiplet).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of a Compound of Formula XVI

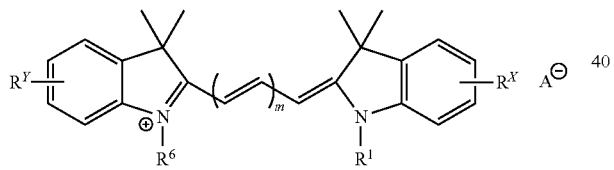

A compound of Formula XVI was prepared according to Scheme 1A, wherein $R^1$, $R^6$, $R^X$, $R^Y$, A and m are each as defined herein.

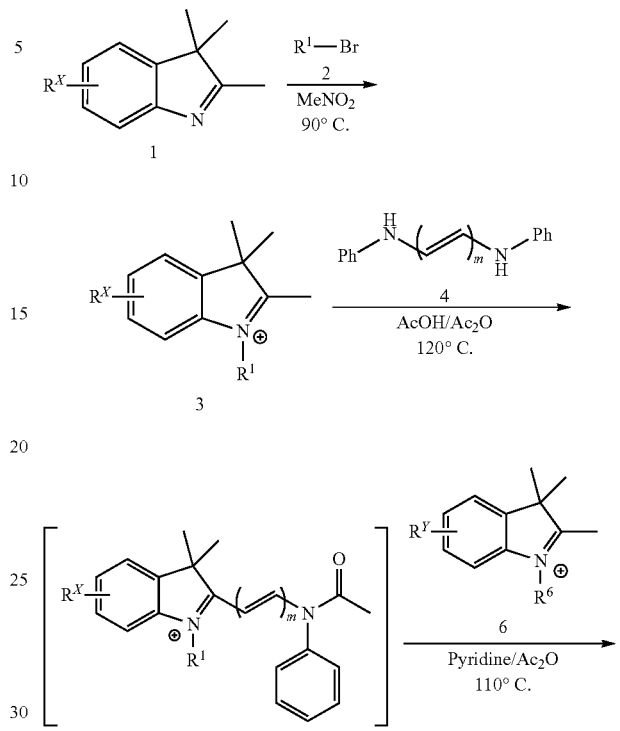

Scheme 1A

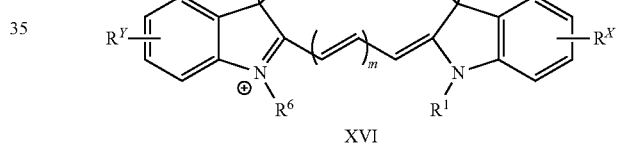

The following compounds were prepared according to the procedures described herein and Scheme 4.

Example 2

Preparation of a Compound of Formula XVe

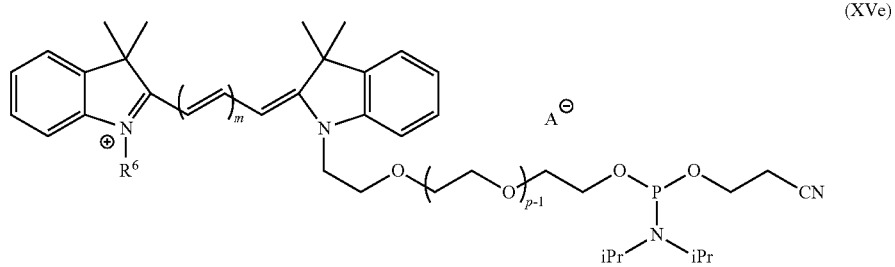

(XVe)

A compound of Formula XVe is prepared according to Scheme 2, wherein $R^6$, A, m, and p are each as defined herein.

Scheme 2
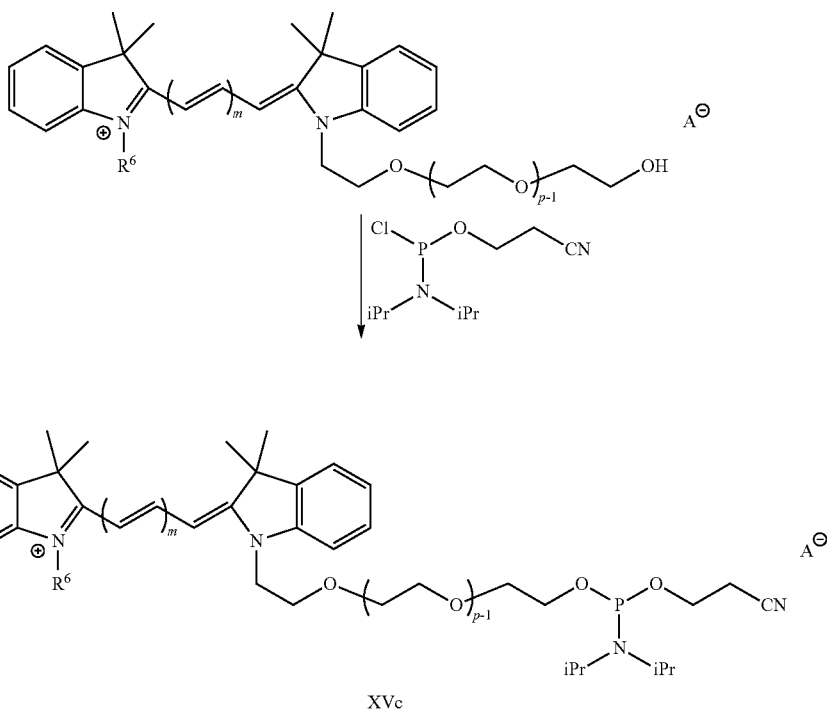
XVc
Example 3
Preparation of a Compound of Formula XVII
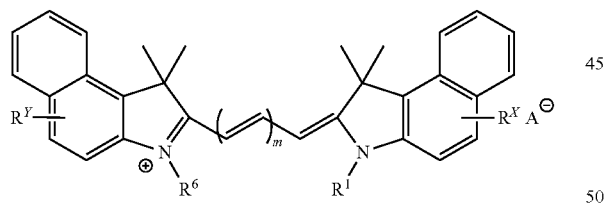
(XVII)
A compound of Formula XVII is prepared according to Scheme 3 and the procedures as described in Example 1, wherein $R^1, R^6, R^X, R^Y, A$, and m are each as defined herein.
Scheme 3
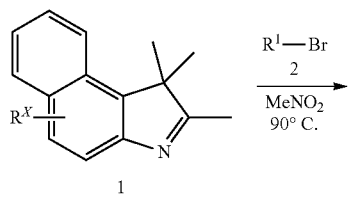

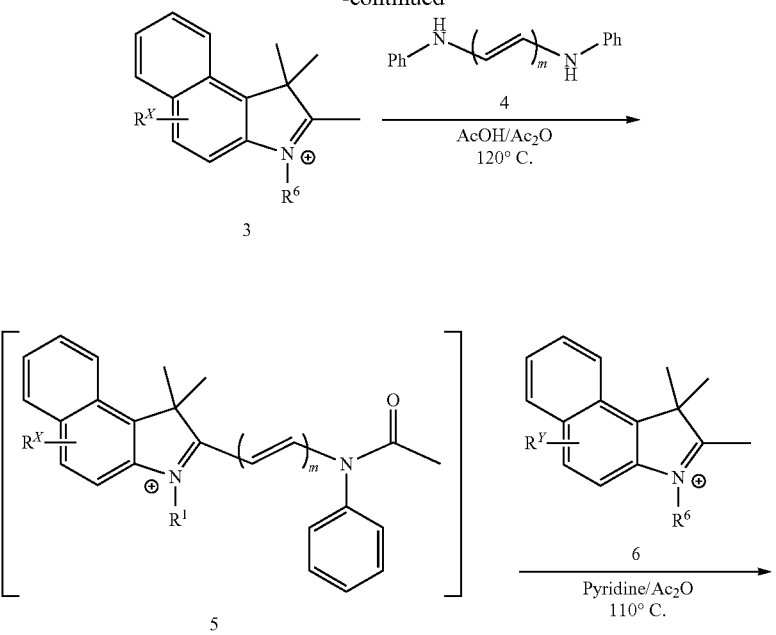
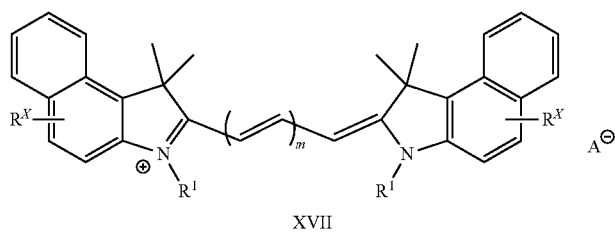
XVII
Example 4
Preparation of a Compound of Formula A
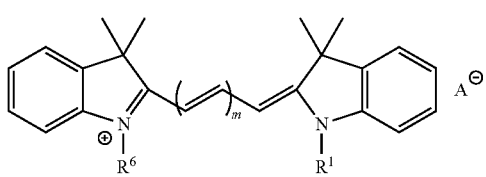
(A)
A compound of Formula A was prepared according to Scheme 4, wherein $R^1$, $R^6$, A, and m are each as defined herein.
Scheme 4
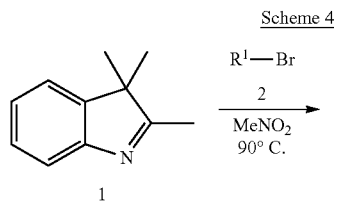
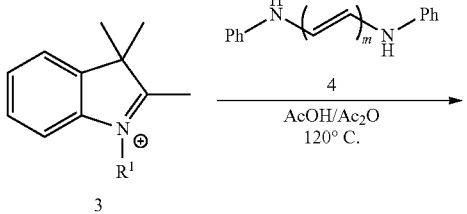
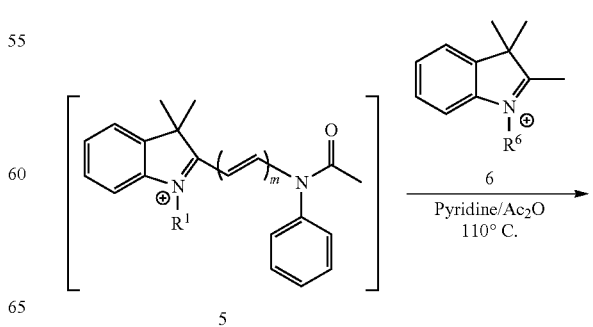

-continued

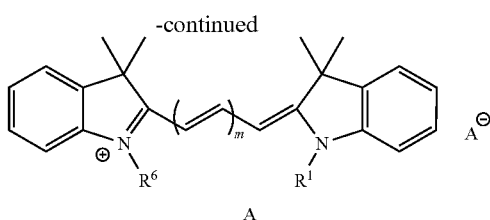

A

To a solution of compound 1 (2 mmol) in nitromethane (1.5 mL) was added compound 2 (2 mmol), and the reaction mixture was stirred at 80-99° C. for 8 hrs under argon. The reaction solution was cooled and triturated with diethyl ether (5 mL). The supernatant was decanted, and the residue was washed with diethyl ether and dried in vacuo to give compound 3

A solution of compounds 3 (1 mmol) and 4 (1.2 mmol) in a mixture of acetic acid (6 mL) and acetic anhydride (6 mL) was stirred at 120° C. for 30-40 min under argon. The reaction solution was cooled and concentrated, and the residue was washed with diethyl ether (3×30 mL) to give intermediate 5, which was used without further purification. For a compound of Formula A in Scheme 4, where m is 1, 2, or 3, N,N'-diphenylformamidine, malondialdehyde bis (phenylimine), or N-(5-(phenylamino)-2,4-pentadienylidene)aniline was used as compound 4, respectively.

For the compound 6 without hydroxyl group, compound 6 (1 mmol) was added to a solution of 5 (1.2 mmol) in dry pyridine. The reaction was heated at 110° C. for 30 min under argon, cooled and then concentrated. The residue was purified by a RP-C18 column.

For compound 6 containing a hydroxyl group, a solution of compound 6 (1 mmol) in acetic anhydride was added to intermediate 5 (1.2 mmol) in pyridine. The reaction mixture was heated at 110° C. for 30 min under argon, cooled and concentrated. The residue was washed with diethyl ether, dissolved in hydrochloric acid (12mL, water/MeOH (1:1)) and stirred at room temperature overnight. The mixture was neutralized with saturated $NaHCO_3$ and concentrated. The residue was partitioned between DCM and water, and the organic phase was separated, dried over anhydride sodium sulfate and concentrated to give the crude product which was purified on a RP-C18 column eluted with acetonitrile in water to afford the compounds of Formula (A).

The following compounds were prepared according to the procedures described herein and Scheme 4.

Compound A1

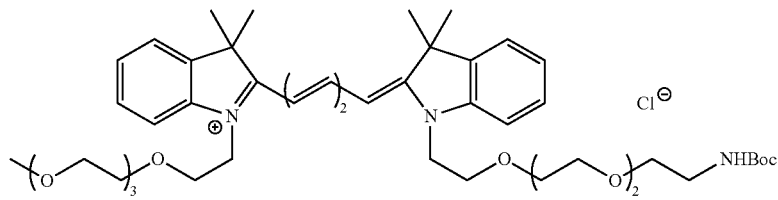

$^1$H NMR (500 MHz, $CD_3OD$) δ 8.25 (t, 2H, J=13.5 Hz), 7.25-7.50 (m, 8H), 6.60 (t, 1H, J=12.5 Hz), 6.40 (d, 2H, J=12.5 Hz), 4.35 (t, 4H), 3.80 (t, 4H), 3.43-3.71 (m, 22H), 3.32 (s, 3H), 3.23 (t, 2H), 1.75(s, 12H), 1.46 (s, 9H); MS (m/z): 821.1.

Compound A2

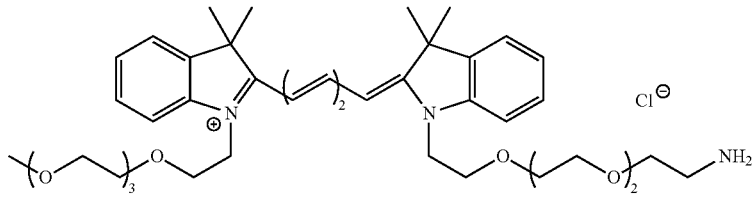

$^1$H NMR (500 MHz, $CD_3OD$) δ 8.25 (t, 2H, J=13.5 Hz), 7.26-7.51 (m, 8H), 6.62 (t, 1H, J=12.5 Hz), 6.40 (d, 2H, J=13.5 Hz), 4.37 (t, 4H), 3.81 (t, 4H), 3.45-3.73 (m, 24H), 3.34 (s, 3H), 1.75 (s, 12H); MS (m/z): 720.9.

Compound A3

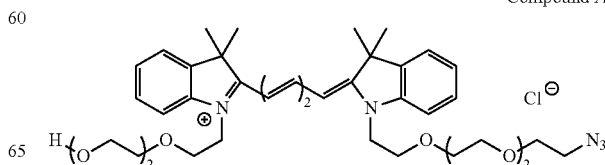

¹H NMR (500 MHz, CD₃OD) δ 8.25 (t, 2H, J=13.5 Hz), 7.25-7.51 (m, 8H), 6.62 (t, 1H, J=12.5 Hz), 6.41 (m, 2H), 4.33 (m, 4H), 3.82 (t, 4H, J=5.5 Hz), 3.52-3.70 (m, 18H), 3.41 (t, 2H), 1.75(s, 12H); MS (m/z): 688.4.

1H, J=12.5 Hz), 6.38 (d, 1H, J=13.5 Hz), 4.34 (t, 2H, J=5.5 Hz), 4.23 (d, 2H, J=5.5 Hz), 3.84 (t, 2H, J=5.5 Hz), 3.55-3.74 (m, 15H), 2.8 (m, 1H), 1.75 (s, 12H); MS (m/z): 583.8.

Compound A4

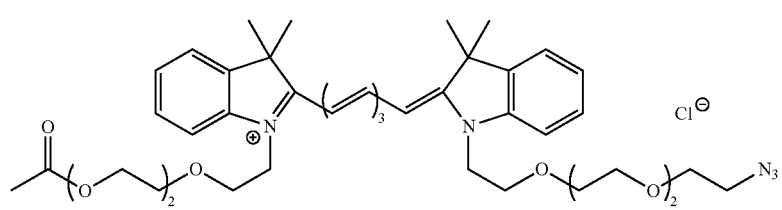

¹H NMR (500 MHz, CD₃OD) δ 7.95 (m, 2H), 7.64 (m, 1H), 7.26-7.50 (m, 8H), 6.63 (t, 2H, J=13.5 Hz), 6.32 (m, 2H), 4.35 (m, 4H), 4.11 (t, 2H), 3.82 (m, 4H), 3.55-3.65 (m, 16H), 3.36 (m, 2H), 2.01 (s, 3H), 1.78 (s, 12H); MS (m/z): 756.9.

Compound A7

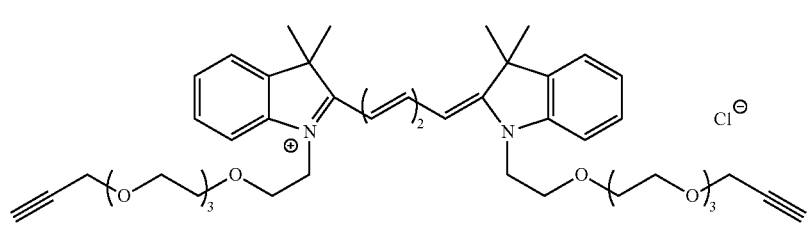

¹H NMR (500 MHz, CD₃OD) δ 8.25 (t, 2H, J=13.5 Hz), 7.29-7.51 (m, 8H), 6.65 (t, 1H, J=12.5 Hz), 6.34 (m, 2H), 4.30 (m, 4H), 4.26 (d, 2H, J=5.5 Hz), 3.87 (t, 4H, J=5.5 Hz), 3.68-3.55 (m, 19H), 3.46 (t, 2H, J=5.5 Hz), 2.88 (t, 1H, J=5.5 Hz), 1.75 (s, 12H); MS (m/z): 701.4.

Compound A5

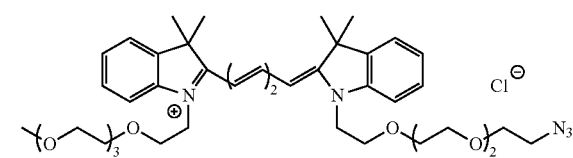

Compound A8

¹H NMR (500 MHz, CD₃OD) δ 8.27 (t, 2H, J=13.5 Hz), 7.28-7.49 (m, 8H), 6.70 (t, 1H, J=12.5 Hz), 6.49 (d, 2H, J=12.5 Hz), 4.31 (t, 4H, J=5.5 Hz), 3.86 (m, 4H), 3.56-3.74 (m, 24H), 3.31 (s, 3H), 1.75 (s, 12H); MS (m/z): 746.9.

¹H NMR (500 MHz, CD₃OD) δ 8.26 (t, 2H, J=13.5 Hz), 7.23-7.50 (m, 8H), 6.60 (t, 1H, J=12.5 Hz), 6.42 (d, 2H, J=13.5 Hz), 4.30 (t, 4H, J=5.5 Hz), 4.26 (d, 4H), 3.85 (t, 4H, J=5.5 Hz), 3.55-3.70 (m, 24H), 2.80 (t, 2H, J=5.5 Hz), 1.75 (s, 12H); MS (m/z): 782.4.

Compound A6

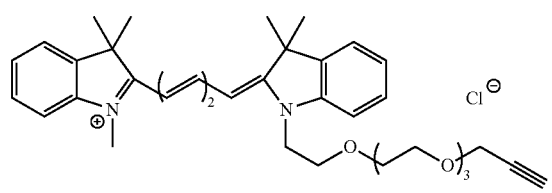

Compound A9

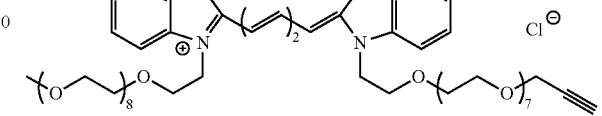

¹H NMR (500 MHz, CD₃OD) δ 8.26 (t, 2H, J=13.5 Hz), 7.25-7.56 (m, 8H), 6.69 (t, 1H, J=12.5 Hz), 6.47 (d,

¹H NMR (500 MHz, CD₃OD) δ 8.24 (t, 2H, J=13.5 Hz), 7.28-7.50 (m, 8H), 6.60 (t, 1H, J=12.5 Hz), 6.44 (d, 2H,

J=13.5 Hz), 4.32 (t, 4H), 4.25 (d, 2H), 3.89 (t, 4H), 3.50-3.75 (m, 62H), 3.31 (s, 3H), 2.82 (t, 1H), 1.75 (s, 12H); MS (m/z): 1156.4.

J=5.5 Hz), 3.35-3.55 (m, 10H), 3.21 (s, 3H), 1.65 (s, 9H), 1.60 (s, 3H); MS (m/z): 544.3.

Compound A10

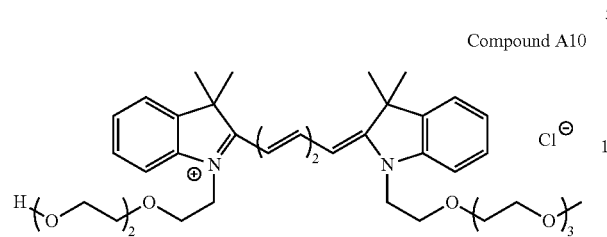

$^1$H NMR (500 MHz, CD$_3$OD) δ 8.26 (t, 2H, J=13.5 Hz), 7.28-7.56 (m, 8H), 6.61 (t, 1H, J=12.5 Hz), 6.32 (m, 2H), 4.33 (m, 4H), 3.84 (m, 4H), 3.45-3.70 (m, 20H), 3.32 (s, 3H), 1.75 (s, 12H); MS (m/z): 677.8.

Compound A13

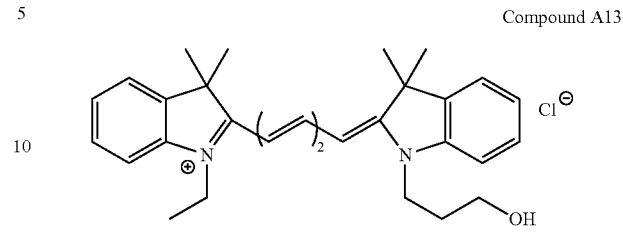

$^1$H NMR (500 MHz, CD$_3$OD) δ 8.25 (t, 2H, J=13.5 Hz), 7.25-7.50 (m, 8H), 6.63 (t, 1H, J=12.5 Hz), 6.38 (d, 1H, J=12.5 Hz), 6.25 (d, 1H, J=13.5 Hz), 4.25 (t, 2H, J=5.5 Hz), 3.70 (t, 2H, J=5.5 Hz), 3.65 (s, 3H), 2.01 (m, 2H), 1.75 (s, 12H); MS (m/z): 427.5.

Compound A11

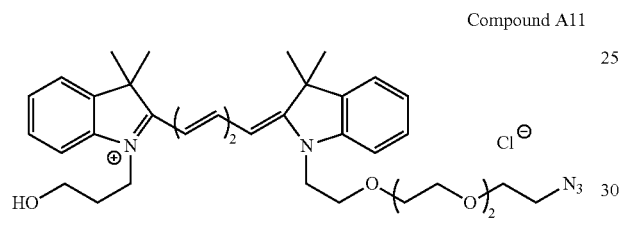

$^1$H NMR (500 MHz, CD$_3$OD) δ 8.41 (t, 2H, J=13.5 Hz), 7.18-7.41 (m, 8H), 6.37 (t, 1H, J=12.5 Hz), 6.34 (d, 2H, J=15.0 Hz), 4.25 (t, 2H, J=5.5 Hz), 4.12 (t, 2H, J=5.5 Hz), 3.80 (m, 2H), 3.47 (m, 2H), 3.43-3.57 (m, 9H), 3.17 (s, 2H), 1.90 (m, 2H), 1.60 (s, 12H); MS (m/z): 588.3.

Compound A14

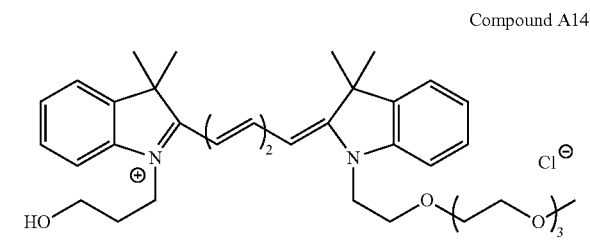

$^1$H NMR (500 MHz, CD$_3$OD) δ 8.27 (t, 2H, J=13.5 Hz), 7.29-7.54 (m, 8H), 6.60 (t, 1H, J=12.5 Hz), 6.35 (d, 1H, J=12.5 Hz), 6.30 (d, 1H, J=15 Hz), 4.30 (t, 2H, J=5.5 Hz), 4.22 (t, 2H, J=5.5 Hz), 3.85 (t, 2H, J=5.5 Hz), 3.70 (m, 2H), 3.42-3.60 (m, 12H), 3.31 (s, 3H), 2.01 (m, 2H), 1.75 (s, 12H); MS (m/z): 603.4.

Compound A12

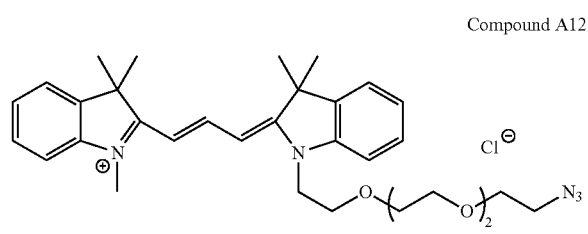

$^1$H NMR (500 MHz, CD$_3$OD) δ 8.44 (t, 1H, J=13.5 Hz), 8.12 (m, 1H), 7.18-7.41 (m, 9H), 6.41 (m, 1H, J=12.5 Hz), 6.38 (d, 1H, J=13.5 Hz), 4.25 (t, 2H, J=5.5 Hz), 3.80 (t, 2H,

Compound A15

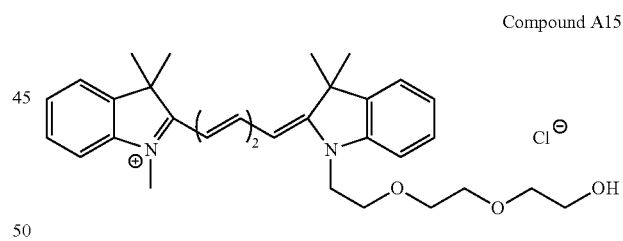

$^1$H NMR (500 MHz, CD$_3$OD) δ 8.26 (t, 2H, J=13.5 Hz), 7.24-7.49 (m, 8H), 6.58 (t, 1H, J=12.5 Hz), 6.39 (d, 1H, J=12.5 Hz), 6.28 (d, 1H, J=13.5 Hz), 4.35 (t, 2H, J=5.5 Hz), 3.85 (t, 2H, J=5.5 Hz), 3.60-3.75 (m, 9H), 3.50 (m, 2H), 1.75 (s, 12H); MS (m/z): 501.6.

Compound A16

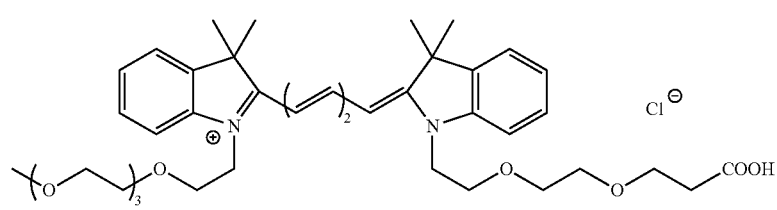

¹H NMR (500 MHz, CD₃OD) δ 8.25 (t, 2H, J=13.5 Hz), 7.28-7.52 (m, 8H), 6.60 (t, 1H, J=12.5 Hz), 6.41 (d, 2H, J=13.5 Hz), 4.30 (m, 4H), 3.85 (m, 4H), 3.52-3.70 (m, 18H), 3.31 (s, 3H), 2.40 (t, 1H), 1.75 (s, 12H); MS (m/z): 705.9.
Compound A17
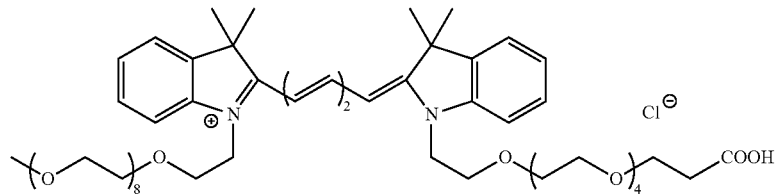
¹H NMR (500 MHz, CD₃OD) δ 8.26 (t, 2H, J=13.5 Hz), 7.30-7.55 (m, 8H), 6.55 (t, 1H, J=12.5 Hz), 6.48 (d, 2H, J=12.5 Hz), 4.34 (t, 4H), 3.75 (t, 2H), 3.56-3.65 (m, 48H), 3.32 (s, 3H), 2.40 (t, 2H), 1.75 (s, 12H); MS (m/z): 1058.3.
Compound A18
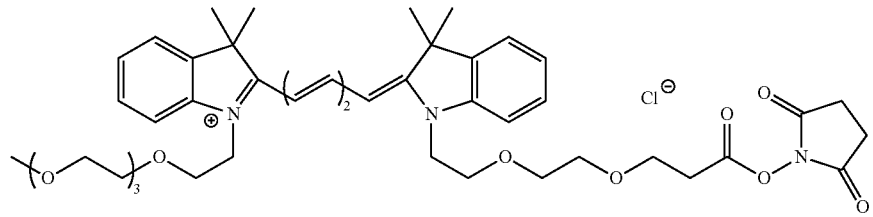
¹H NMR (500 MHz, CD₃OD) δ 8.24 (t, 2H, J=13.5 Hz), 7.27-7.50 (m, 8H), 6.70 (t, 1H, J=12.5 Hz), 6.38 (t, 2H, J=13.5 Hz), 4.32 (m, 4H), 3.80 (m, 4H), 3.75 (t, 2H, J=5.5 Hz), 3.58-3.70 (m, 16H), 3.35 (s, 4H), 3.31 (t, 2H, J=5.5 Hz), 1.75 (s, 12H); MS (m/z): 802.9.
Compound A19
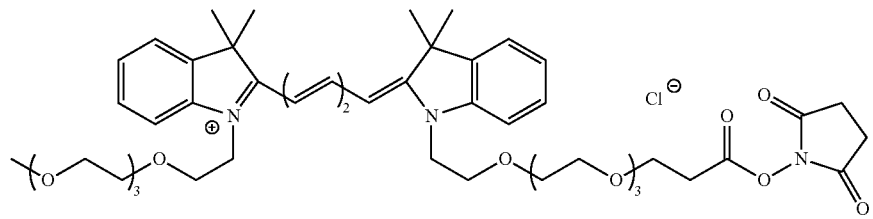
¹H NMR (500 MHz, CD₃OD) δ 8.17 (t, 2H, J=13.5 Hz), 7.18-7.33 (m, 8H), 6.82 (t, 1H, J=12.5 Hz), 6.55 (t, 1H, J=10 Hz), 6.50 (t, 1H, J=13.5 Hz), 4.31 (t, 4H, J=5.5 Hz), 3.90 (t, 4H, J=5.5 Hz), 3.51-3.72 (m, 29H), 2.84 (t, 2H, J=7.5 Hz), 2.76 (m, 4H), 1.72 (s, 12H). MS (m/z): 891.2.
Compound A20
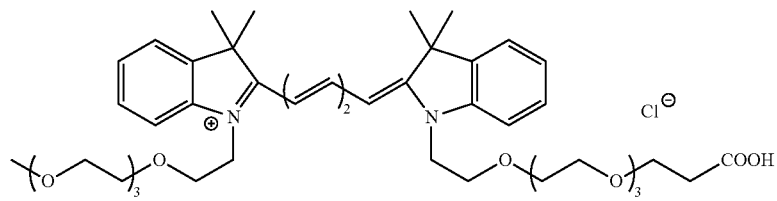

¹H NMR (500 MHz, CD₃OD) δ 8.23 (t, 2H, J=13.5 Hz),7.24-7.47 (m, 8H), 6.59 (t, 1H, J=12.5 Hz), 6.48 (d, 1H, J=12.5 Hz), 6.38 (d, 1H, J=13.5 Hz), 4.31 (t, 2H, J=5.5 Hz), 3.87 (t, 2H, J=5.5 Hz), 3.67 (t, 2H, J=5.0 Hz), 3.48-3.64 (m, 31H), 2.41 (t, 2H, J=7.5 Hz), 1.72 (s, 12H); MS (m/z): 792.3.

Compound A21

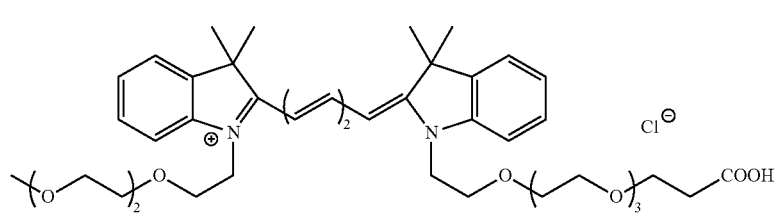

¹H NMR (500 MHz, CD₃OD): δ 8.24 (t, 2H, J=13.5 Hz),7.25-7.47 (m, 8H), 6.58 (t, 1H, J=12.5 Hz), 6.48 (d, 1H, J=12.5 Hz), 6.38 (d, 1H, J=13.5 Hz), 4.32 (t, 2H, J=5.5 Hz), 3.88 (t, 2H, J=5.5 Hz), 3.68 (m, 2H), 3.48-3.65 (m, 31H), 2.41 (m, 2H), 1.72 (s, 12H); MS (m/z): 793.4.

Compound A22

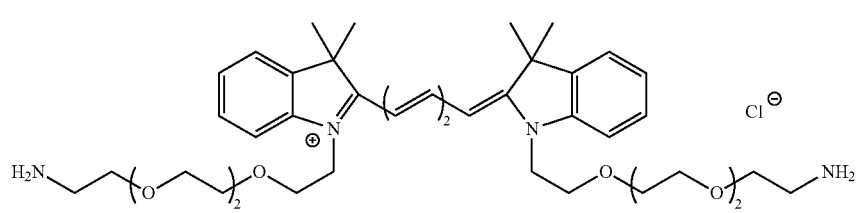

¹H NMR (500 MHz, CD₃OD) δ 8.27 (t, 2H, J=13.5 Hz), 7.47 (d, 2H, J=8.0 Hz), 7.39 (m, 2H), 7.32 (m, 2H), 7.24 (m, 2H), 6.57 (t, 1H, J=13.5 Hz), 6.32 (d, 2H, J=15.0 Hz), 4.31 (m, 3H), 3.87 (m, 4H), 3.51-3.73 (m, 22H), 3.06 (m, 3H), 1.75 (m, 12H); MS (m/z): 705.6.

Compound A23

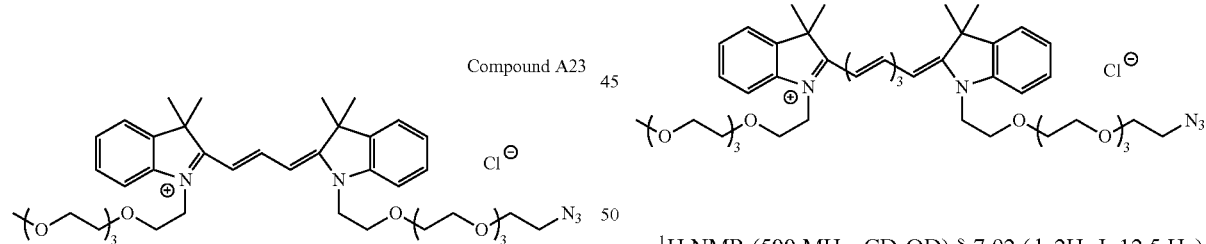

¹H NMR (500 MHz, CD₃OD): δ 8.65 (t, 1H, J=13.5 Hz), 7.57 (d, 2H, J=8.0 Hz), 7.46 (m, 4H), 7.34 (m, 2H), 6.54 (d, 2H, J=13.5 Hz), 4.40 (m, 3H), 3.95 (m, 4H), 3.51-3.70 (m, 29H), 3.31 (s, 3H), 1.80 (m, 12H); MS (m/z): 765.8.

Compound A24

¹H NMR (500 MHz, CD₃OD) δ 7.92 (d, 2H, J=12.5 Hz), 7.57 (m, 2H), 7.45 (m, 3H), 7.36 (m, 2H), 7.29 (m, 2H), 7.22 (m, 2H), 6.55 (m, 2H), 4.28 (m, 3H), 3.86 (m, 4H), 3.42-3.61 (m, 29H), 3.32 (s, 3H), 1.68 (m, 12H); MS (m/z): 816.6.

Compound A25

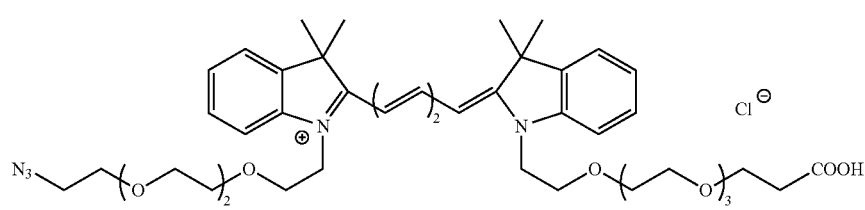

¹H NMR (500 MHz, CD₃OD) δ 8.14 (t, 2H, J=13.5 Hz),7.16-7.38 (m, 8H), 6.50 (t, 1H, J=12.5 Hz), 6.32 (d, 1H, J=15 Hz), 6.27 (d, 1H, J=13.5 Hz), 4.23 (t, 4H, J=5.5 Hz), 3.79 (t, 4H, J=5.5 Hz), 3.39-3.79 (m, 24H), 3.25 (m, 2H), 2.34 (m, 2H), 1.63 (s, 12H); MS (m/z): 805.5.
Compound A26
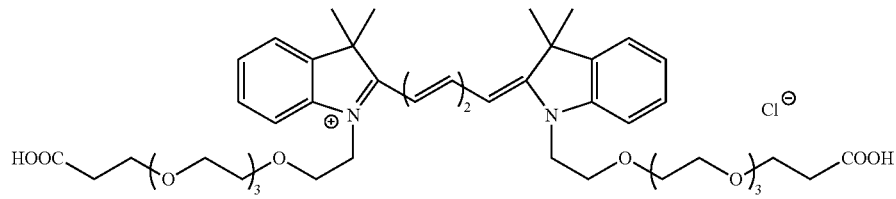
¹H NMR (500 MHz, CD₃OD) δ 8.05 (t, 2H, J=13.5 Hz),7.09-7.32 (m, 8H), 6.44 (t, 1H, J=12.5 Hz), 6.25 (d, 1H, J=13.5 Hz), 6.22 (d, 1H, J=13.5 Hz), 4.16 (t, 4H, J=6.5 Hz), 3.73 (t, 4H, J=5.5 Hz), 3.34-3.54 (m, 28H), 2.36 (m, 4H), 1.57 (s, 12H); MS (m/z): 852.7.
Compound A27
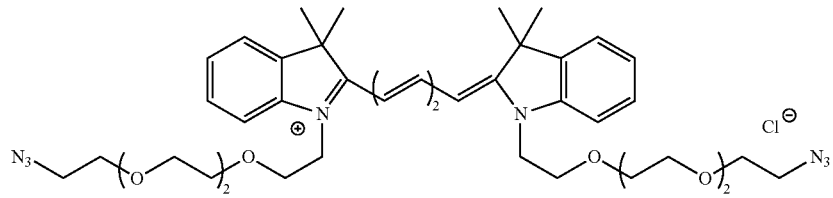
¹H NMR (500 MHz, CD₃OD) δ 8.23 (t, 2H, J=13.5 Hz), 7.46 (d, 2H, J=8.0 Hz), 7.36 (t, 2H, J=8.0 Hz), 7.26 (d, 2H, J=8.0 Hz), 7.23 (t, 2H, J=7.5 Hz), 6.60 (t, 1H, J=13.5 Hz), 6.38 (m, 2H),4.30 (t, 4H, J=5.5 Hz), 3.88 (t, 4H, J=5.5 Hz), 3.51-3.58 (m, 24H), 1.72 (s, 12H); MS (m/z): 757.2.
Compound A28
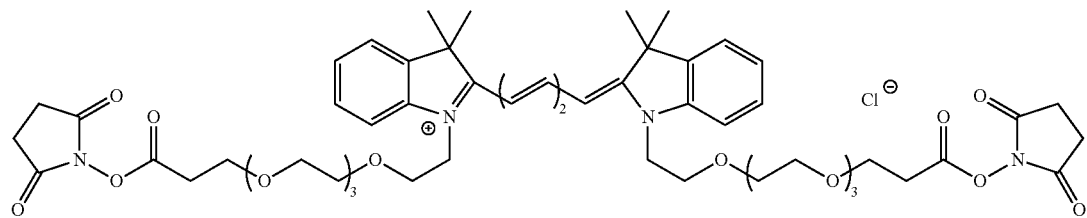
¹H NMR (500 MHz, CD₃OD) δ 8.23 (t, 2H, J=13.5 Hz),7.18-7.32 (m, 8H), 6.83 (t, 1H, J=12.5 Hz), 6.50 (t, 1H, J=12.5 Hz), 6.48 (d, 1H, J=13.5 Hz), 4.33 (t, 4H, J=5.5 Hz), 3.90 (t, 4H, J=5.5 Hz), 3.84 (m, 4H), 3.34-3.54 (m, 24H), 2.81 (m, 8H), 2.62 (m, 4H), 1.72 (s, 12H); MS (m/z): 1046.2.

Example 5

Preparation of a Compound of Formula XVIII (XVIII)

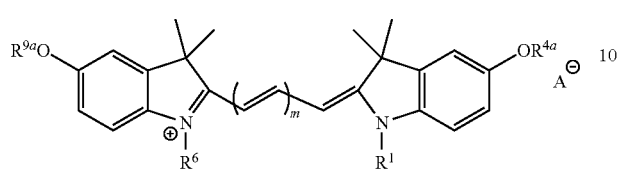

A compound of Formula XVIII was prepared according to Scheme 5, wherein $R^1$, $R^6$, $R^{4a}$, $R^{9a}$, A, and m are each as defined herein.

Scheme 5

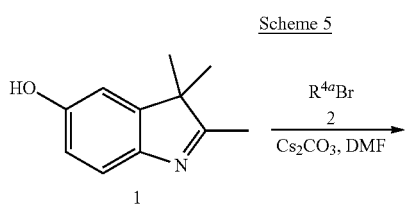

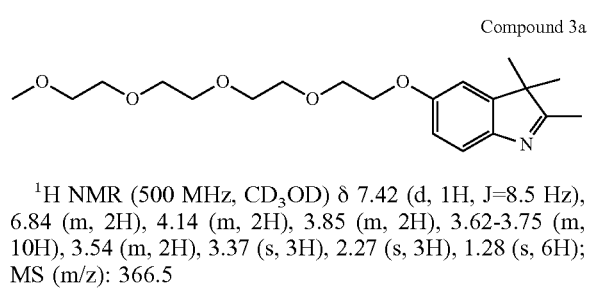

To a solution of 1 (16.7 mmol) in dimethylformamide (35 mL) were added $Cs_2CO_3$ (18.4 mmol) and 2 (16.7 mmol) and the reaction mixture was stirred at 60° C. for 16 hrs. The reaction solution was cooled and concentrated, and the residue was purified by column chromatography with EtOAc/DCM to give 3.

Compounds 3a and 3b were prepared according to the procedures described herein and Scheme 5.

Compound 3a

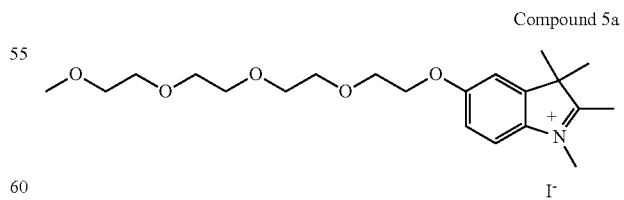

$^1$H NMR (500 MHz, $CD_3OD$) δ 7.42 (d, 1H, J=8.5 Hz), 6.84 (m, 2H), 4.14 (m, 2H), 3.85 (m, 2H), 3.62-3.75 (m, 10H), 3.54 (m, 2H), 3.37 (s, 3H), 2.27 (s, 3H), 1.28 (s, 6H); MS (m/z): 366.5

Compound 3b

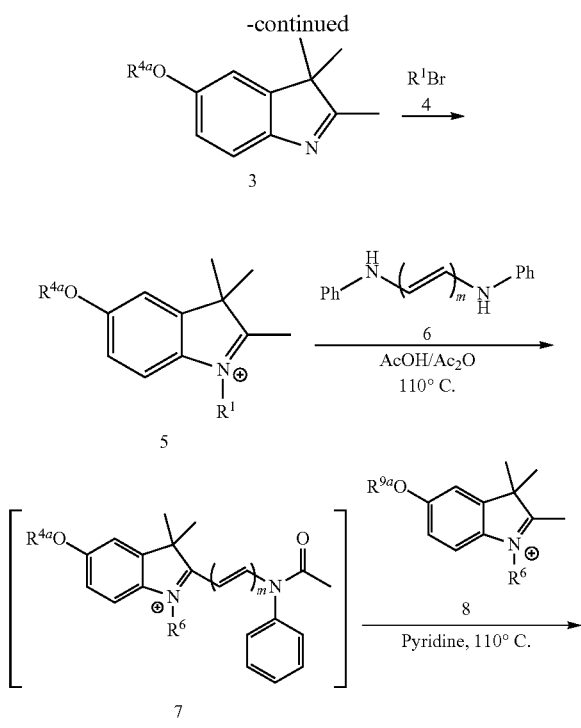

$^1$H NMR (500 MHz, $CD_3OD$) δ 7.47 (d, 1H, J=8.5 Hz), 6.87 (m, 1H), 6.82 (m, 1H), 4.18 (m, 2H), 4.14 (m, 2H), 3.86 (m, 2H), 3.73 (m, 2H), 3.65-3.70 (m, 10H), 2.42 (m, 1H), 2.27 (s, 3H), 1.28 (s, 6H); MS (m/z): 390.6.

A mixture of compounds 3 (2.7 mmol) and 4 (2.7 mmol) was stirred at 80-99° C. for 8 hrs under argon. The reaction solution was cooled and concentrated, and the residue was washed with diethyl ether to give 5.

Compounds 5a and 5b were prepared according to the procedures described herein and Scheme 5.

Compound 5a $^1$H NMR (500 MHz, $CD_3OD$): δ 7.73 (d, 1H, J=8.5 Hz), 7.35 (m, 1H), 7.17 (m, 1H), 4.20 (m, 2H), 3.97 (m, 3H), 3.85 (m, 2H), 3.50-3.68 (m, 12H), 3.34 (s, 3H), 2.13 (s, 3H), 1.54 (s, 6H); MS (m/z): 380.3.

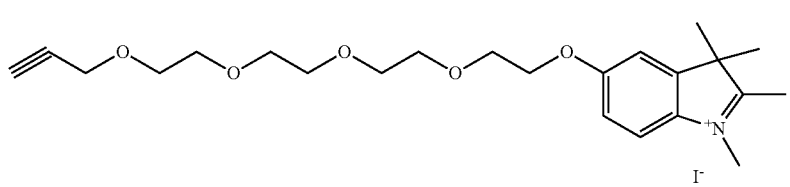
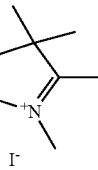

Compound 5b

¹E NMR (500 MHz, CD₃OD) δ 7.74 (m, 1H), 7.37 (m, 1H), 7.20 (m, 1H), 4.25 (m, 2H), 4.18 (m, 2H), 3.90 (m, 2H), 3.72 (m, 2H), 3.61-3.67 (m, 10H), 3.32 (s, 3H), 2.85 (m, 1H), 2.18 (s, 3H), 1.59 (s, 6H); MS (m/z): 404.6.

A solution of compounds 5 (2.7 mmol) and 6 (2.7 mmol) in a mixture of acetic acid (3 mL) and acetic anhydride (3 mL) was stirred at 110° C. for 30-40 mins under argon. The reaction mixture was cooled and concentrated, and the residue was washed with diethyl ether (3×10 mL) to give intermediate compound 7, which was used for the following reaction without further purification. For the compounds of Formula XVIII in Scheme 5, where m is 1, 2, or 3, N,N'-diphenylformamidine, malondialdehyde bis(phenylimine), or N-(5-(phenylamino)-2,4-pentadienylidene)aniline was used as compound 6, respectively.

To a solution of 8 (0.6 mmol) in dry pyridine (5 mL) was added 7 (0.6 mmol) and the reaction mixture was stirred at 110° C. for 40 mins under argon. The reaction solution was cooled and concentrated, and the residue was washed with diethyl ether, and dried in vacuo. The residue was re-dissolved in DCM, washed with hydrochloric acid (0.1 M), brine and concentrated. The crude product was purified on a RP-C18 column eluted with acetonitrile in water to afford the compounds of formula XVIII.

The following compounds were prepared according to the procedures described herein and Scheme 5.

Compound B

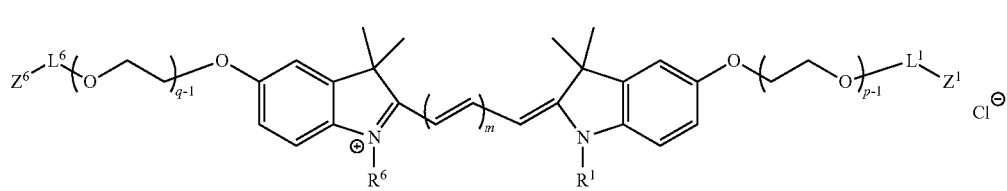

Compound B1

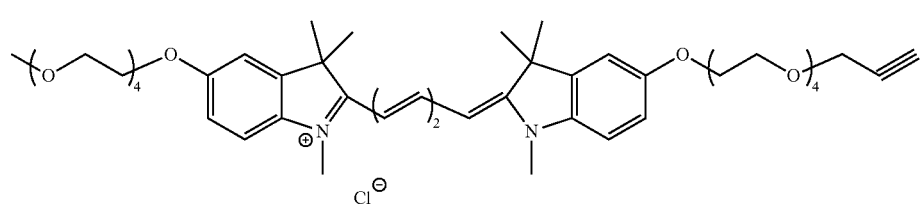

¹H NMR (500 MHz, CD₃OD) δ 8.09 (t, 2H, J=13.5 Hz), 7.16 (m, 2H), 7.10 (m, 2H), 6.95 (m, 2H), 6.51 (t, 1H, J=12.5 Hz), 6.13 (d, 2H, J=15.0 Hz), 4.56 (m, 4H), 4.13 (m, 6H), 3.82 (m, 4H), 3.49-3.68 (m, 23H), 3.27 (m, 6H), 2.81 (m, 1H), 1.75 (m, 12H); MS (m/z): 820.2.

Compound B2

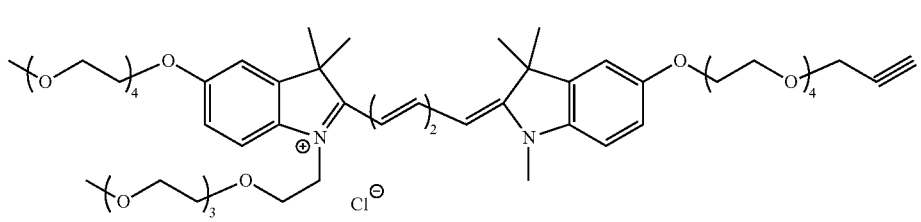

¹H NMR (500 MHz, CD₃OD) δ 8.11 (t, 2H, J=10 Hz), 7.21 (m, 2H), 7.10 (m, 2H), 6.94 (m, 2H), 6.52 (t, 1H, J=10 Hz), 6.16-6.28 (m, 2H), 4.60 (m, 4H), 4.25 (m, 2H), 4.13 (m, 6H), 3.82 (m, 6H), 3.47-3.68 (m, 35H), 3.27 (m, 6H), 2.82 (m, 1H), 1.67 (m, 12H); MS (m/z): 996.3.

Compound B3
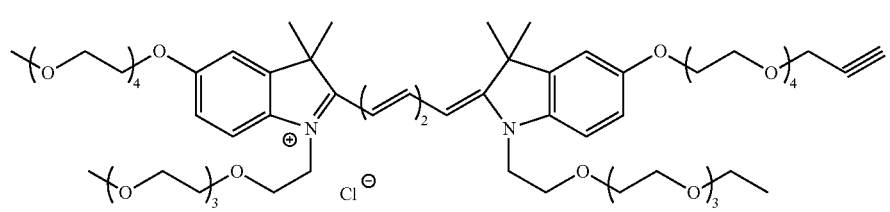
¹H NMR (500 MHz, CD$_3$OD) δ 8.11 (t, 2H, J=13.5 Hz), 7.21 (m, 2H), 7.10 (m, 2H), 6.94 (m, 2H), 6.52 (t, 1H, J=12.5 Hz), 6.16-6.28 (m, 2H), 4.60 (m, 4H), 4.25 (m, 2H), 4.13 (m, 6H), 3.82 (m, 6H), 3.47-3.68 (m, 35H), 3.27 (m, 6H), 2.82 (m, 1H), 1.67 (m, 12H); MS (m/z): 996.3.
Compound B4
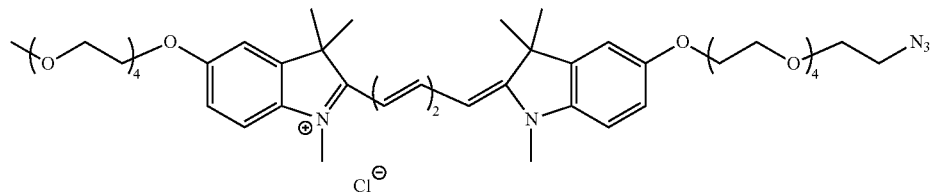
¹H NMR (500 MHz, CD$_3$OD) δ 8.08 (t, 2H, J=13.5 Hz), 7.13 (d, 2H, J=8.5 Hz), 7.10 (m, 2H), 6.96 (m, 2H), 6.48 (m, 1H), 6.15 (d, 2H, J=15.0 Hz), 4.19 (m, 4H), 3.87 (m, 4H), 3.64-3.72 (m, 29H), 3.45 (m, 2H), 3.35 (m, 6H), 1.75 (m, 12H); MS (m/z): 850.6.
Compound B5
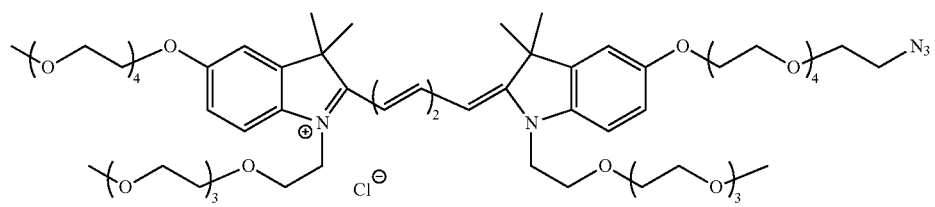
¹H NMR (500 MHz, CD$_3$OD) δ 8.10 (t, 2H, J=14.0 Hz), 7.15 (d, 2H, J=9.0 Hz), 7.09 (m, 2H), 6.94 (m, 2H), 6.48 (t, 1H, J=12.5 Hz), 6.26 (d, 2H, J=14.0 Hz), 4.59 (m, 7H), 4.24 (m, 2H), 4.14 (m, 3H), 3.83 (m, 6H), 3.47-3.68 (m, 59H), 1.66 (m, 12H); MS (m/z): 1203.1.
Compound B6
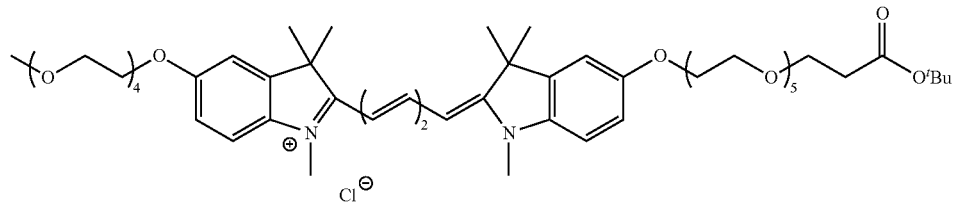

¹H NMR (500 MHz, CD₃OD) δ 8.12 (t, 2H, J=13.5 Hz), 7.18 (d, 2H, J=8.0 Hz), 7.12 (m, 2H), 6.97 (m, 2H), 6.53 (t, 1H, J=15.0 Hz), 6.17 (d, 2H), 4.59 (m, 1H), 4.15 (m, 4H), 3.84 (m, 4H), 3.49-3.72 (m, 36H), 3.35 (m, 3H), 2.43 (m, 1H), 1.69 (m, 12H), 1.42 (s, 9H); MS (m/z): 954.5.

Compound B7

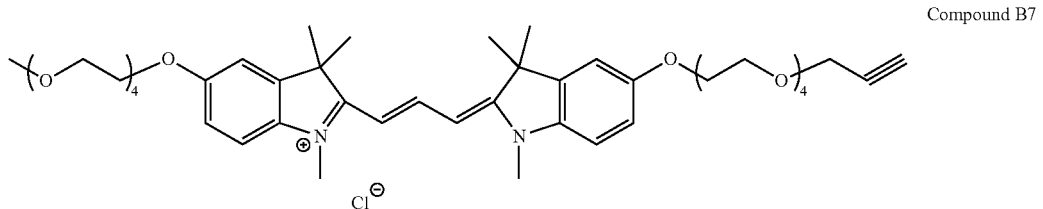

¹H NMR (500 MHz, CD₃OD) δ 8.47 (t, 1H, J=13.5 Hz), 7.24 (d, 2H, J=9.0 Hz), 7.17 (m, 2H), 6.95 (m, 2H), 6.25 (d, 1H, J=13.5 Hz), 4.16 (m, 2H), 3.85 (m, 4H), 3.61-3.70 (m, 32H), 3.51 (m, 2H), 3.32 (s, 3H), 2.82 (m, 1H), 1.73 (m, 12H); MS (m/z): 794.3.

Compound B8

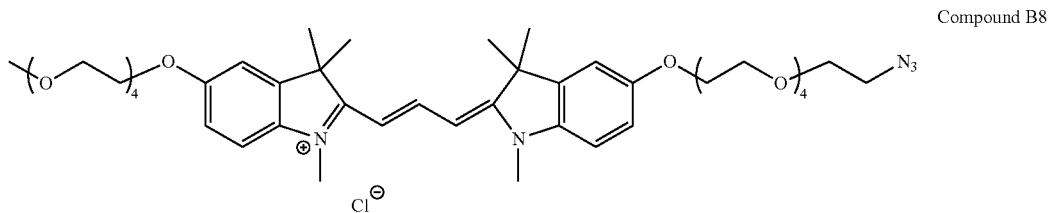

¹H NMR (500 MHz, CD₃OD) δ 8.45 (t, 1H, J=13.5 Hz), 7.26 (d, 2H, J=8.5 Hz), 7.19 (m, 2H), 7.03 (m, 2H), 6.31 (d, 2H, J=15.0 Hz), 4.19 (m, 4H), 3.87 (m, 4H), 3.73 (m, 4H), 3.64-3.68 (m, 28H), 3.53 (m, 2H), 3.35 (s, 3H), 1.69 (m, 12H); MS (m/z): 824.6.

Example 6

Preparation of a Compound of Formula XVIf

Scheme 6

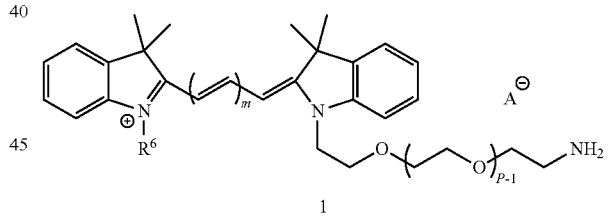

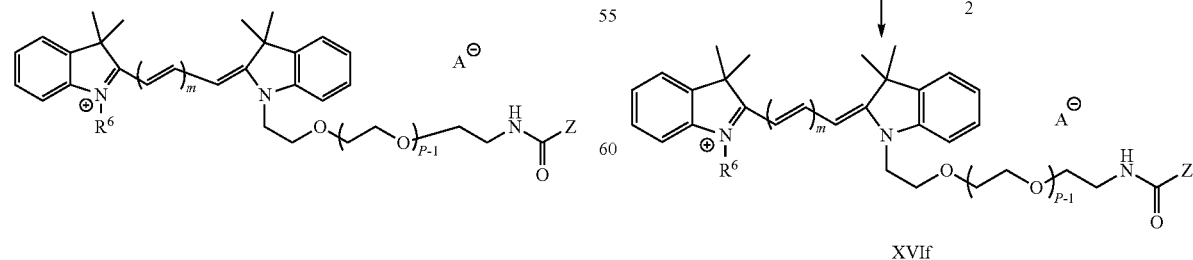

A compound of Formula XVIf is prepared according to Scheme 6, wherein R⁶, A, Z, m, and p are each as defined herein.

To a solution of compound 1 (0.2 mmol) in DCM (2 mL) was added triethylamine (0.3 mmol) and compound 2 (0.3 mmol) consequentially and the solution stirred at room temperature for 40 min. The reaction mixture was diluted by DCM, washed with hydrochloric acid (0.1 M), brine and concentrated. The residue was purified on a RP-C18 column eluted with acetonitrile in water to afford the target compounds.

Compound 1 is prepared according to Scheme 4, wherein $R^1$, $R^6$, $R^X$, $R^Y$, and m are each as defined herein.

The following compounds were prepared according to the procedures described herein and Scheme 6.

Compound C

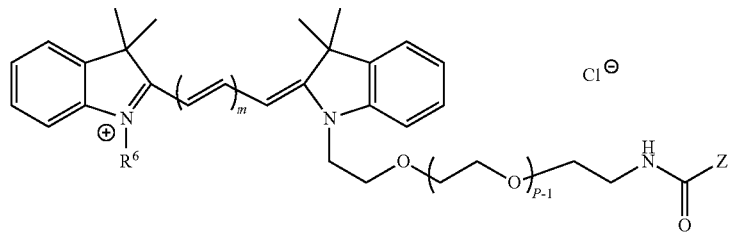

Compound C1

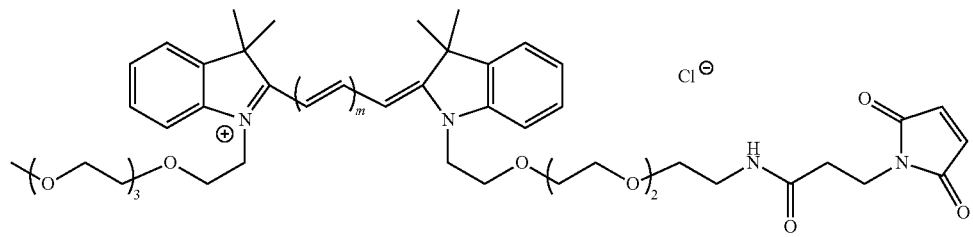

$^1$H NMR (500 MHz, CD$_3$OD) δ 8.25 (t, 2H, J=13.5 Hz), 7.47 (d, 2H, J=8.5 Hz), 7.39 (m, 2H), 7.32 (m, 2H), 7.24 (m, 2H), 6.77 (s, 2H), 6.57 (t, 1H, J=13.5 Hz), 6.38 (d, 2H, J=15.0 Hz), 4.31 (m, 3H), 3.88 (m, 4H), 3.73 (m, 2H), 3.45-3.55 (m, 26H), 3.24 (m, 2H), 2.42 (m, 2H), 1.72 (m, 12H); MS (m/z): 872.6.

Compound C2

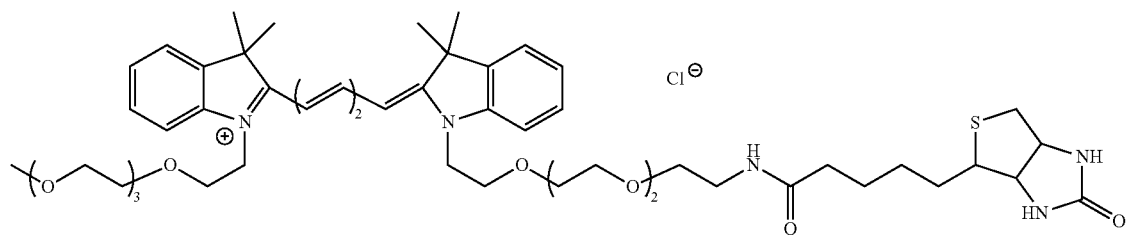

$^1$H NMR (500 MHz, CD$_3$OD) δ 8.23 (t, 2H, J=12.5 Hz), 7.47 (d, 2H, J=9.0 Hz), 7.38 (m, 2H), 7.33 (m, 2H), 7.24 (m, 2H), 6.57 (t, 1H, J=12.5 Hz), 6.38 (m, 2H), 4.46 (m, 1H), 4.31 (m, 5H), 3.87 (m, 4H), 3.43-3.58 (m, 26H), 3.15 (m, 2H), 2.86 (m, 1H), 2.72 (m, 1H), 2.17 (m, 2H), 1.72 (m, 12H), 1.55-1.61 (m, 4H), 1.38-1.41 (m, 2H); MS (m/z): 947.8.

Example 7
Preparation of a Compound of Formula XVIg

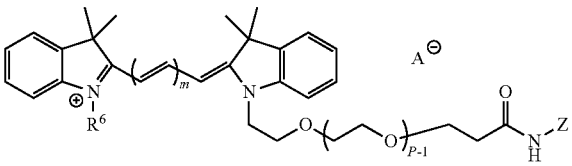

A compound of Formula XVIg is prepared according to Scheme 7, wherein $R^6$, A, m, P, and Z are each as defined herein.

Scheme 7

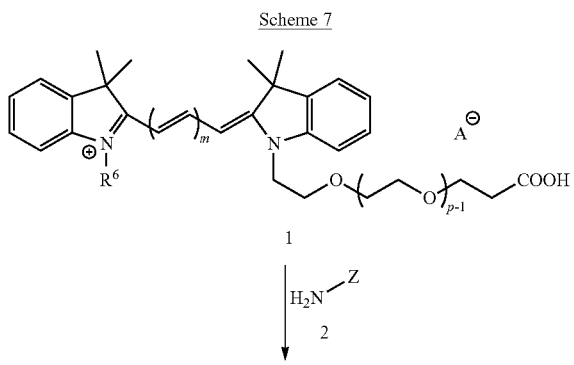

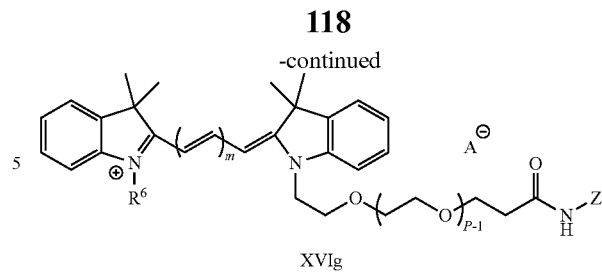

XVIg

Compound 1 (0.1 mmol), EDCI (0.15 mmol), HOBt (0.15 mmol), amines with functional group (0.15 mmol) (such as amine, hydroxyl, DABCO, maleimide) were dissolved in DCM (10.0 mL). The reaction mixture was stirred at room temperature overnight and then concentrated. The residue was purified on a RP-C18 column eluted with acetonitrile in water to afford the target compounds.

Compound 1 is prepared according to Scheme 4, wherein $R^1$, $R^6$, $R^X$, $R^Y$, and m are each as defined herein.

The following compounds were prepared according to the procedures described herein and Scheme 7.

Compound D

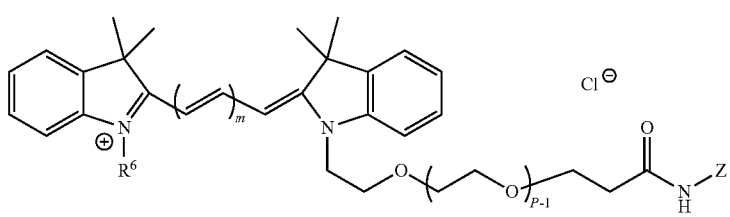

Compound D1

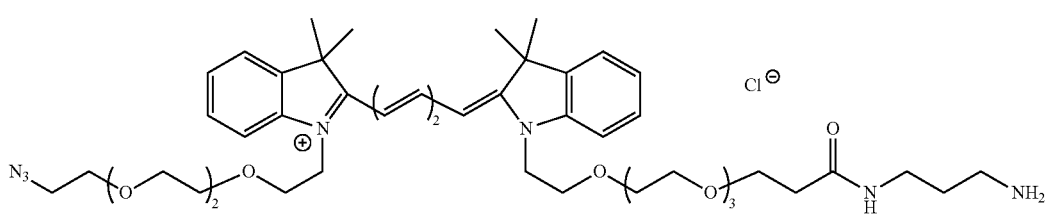

$^1$H NMR (500 MHz, CD$_3$OD) δ 8.15 (t, 2H, J=13.5 Hz), 7.14-7.36 (m, 8H), 6.46 (t, 1H, J=12.5 Hz), 6.28 (d, 1H, J=13.5 Hz), 6.21 (d, 1H, J=13.5 Hz), 4.19 (t, 4H, J=5.5 Hz), 3.75 (t, 4H, J=5.5 Hz), 3.38-3.60 (m, 26H), 3.21 (m, 2H), 2.80 (m, 2H), 2.30 (m, 2H), 1.74 (m, 2H), 1.63 (s, 12H); MS (m/z): 861.7.

Compound D2

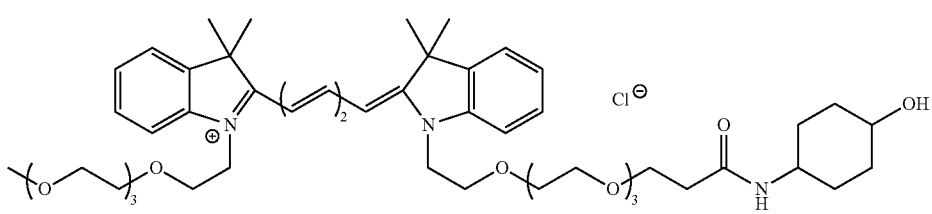

$^1$H NMR (500 MHz, CD$_3$OD): δ 8.09 (t, 2H, J=13.5 Hz), 7.07-7.47 (m, 8H), 6.44 (t, 1H, J=12.5 Hz), 6.24 (d, 1H, J=13.5 Hz), 6.20 (d, 1H, J=12.5 Hz), 4.16 (t, 4H, J=6.0 Hz), 3.72 (t, 2H, J=5.5 Hz), 3.15-3.56 (m, 34H), 3.30 (m, 1H), 2.22 (m, 2H), 1.77 (m, 4H), 1.57 (s, 12H), 1.11-1.25 (m, 4H); MS (m/z): 891.9.

Compound D3
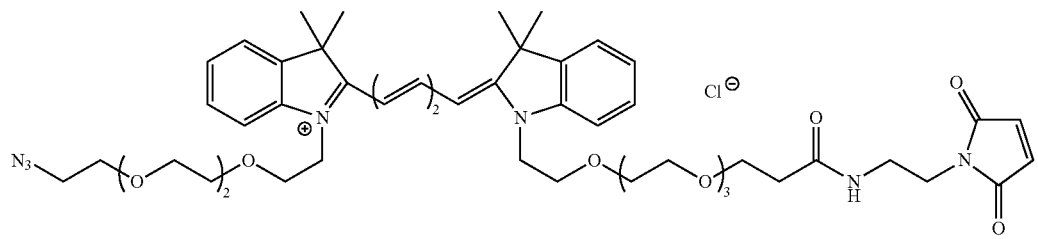
¹H NMR (500 MHz, CD₃OD) δ 8.14 (t, 2H, J=13.5 Hz), 7.16-7.38 (m, 8H), 6.77 (s, 2H), 6.50 (t, 1H, J=12.5 Hz), 6.32 (d, 1H, J=15 Hz), 6.27 (d, 1H, J=13.5 Hz), 4.23 (t, 4H, J=6.0 Hz), 3.79 (t, 4H, J=6.0 Hz), 3.39-3.79 (m, 28H), 3.25 (t, 2H, J=7.5 Hz), 2.34 (t, 2H, J=7.5 Hz), 1.63 (s, 12H); MS (m/z): 927.7.
Compound D4
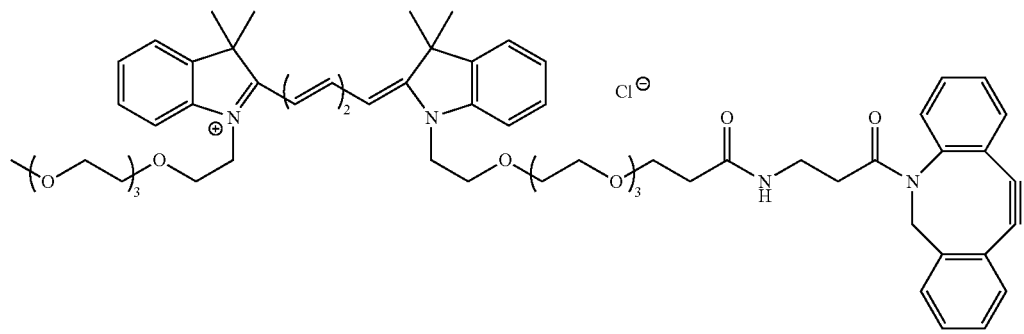
¹H NMR (500 MHz, CD₃OD) δ 8.14 (t, 2H, J=13.5 Hz), 7.11-7.52 (m, 16H), 6.48 (t, 1H, J=12.5 Hz), 6.26 (d, 1H, J=13.5 Hz), 6.23 (d, 1H, J=13.5 Hz), 4.50 (s, 2H), 4.18 (t, 4H, J=6.0 Hz), 3.75 (t, 4H, J=6.0 Hz), 3.21-3.52 (m, 31H), 2.37 (t, 2H, J=7.5 Hz), 2.13 (t, 2H, J=7.5 Hz), 1.59 (s, 12H); MS (m/z): 1052.5.
Compound D5
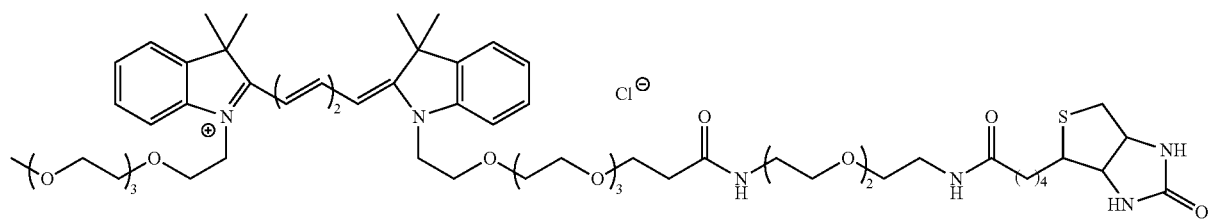

¹H NMR (500 MHz, CD₃OD) δ 8.12 (t, 2H, J=13.5 Hz), 7.12-7.36 (m, 8H), 6.48 (t, 1H, J=12.5 Hz), 6.28 (d, 1H, J=12.5 Hz), 6.25 (d, 1H, J=13.5 Hz), 4.51 (m, 1H), 4.20 (m, 5H), 3.76 (t, 4H, J=6.0 Hz), 3.07-3.60 (m, 45H), 2.80 (m,1H), 2.77 (m, 1H), 2.55 (m, 1H), 2.31(t, 2H, J=10.0 Hz), 2.08(t, 2H, J=10.0 Hz), 1.61 (m, 12H), 1.53 (m, 4H), 1.43 (m, 2H); MS (m/z): 1150.1.

Example 8

Preparation of a Compound of Formula E

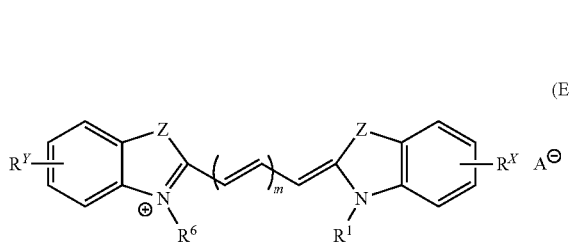

(E)

A compound of Formula E was prepared according to Scheme 8, wherein $R^1$, $R^6$, $R^X$ and $R^Y$ are each as defined herein.

Scheme 8

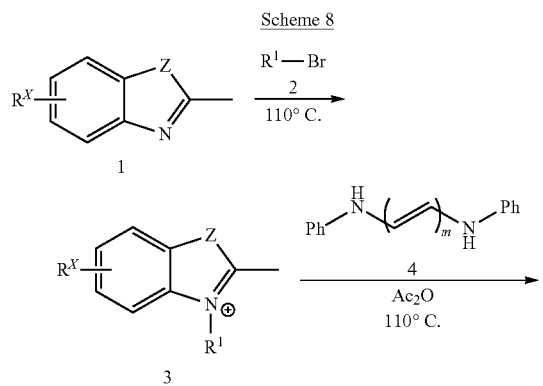

A mixture of 1 and 2 was stirred at 110° C. overnight under argon, cooled and then triturated with diethyl ether (5 mL). The supernatant was decanted, and the residue was washed with diethyl ether and dried in vacuum to yield compound 3.

A solution of compounds 3 (0.6 mmol) and 4 (0.6 mmol) in acetic anhydride (6 mL) was stirred at 110° C. for 30-40 min. The reaction solution was cooled and concentrated. The residue was washed with diethyl ether (3×5 mL) to give intermediate 5, which was used for the next reaction without further purification. For the compounds of Formula E in Scheme 8, where m is 1, 2, or 3, N,N'-diphenylformamidine, malondialdehyde bis(phenylimine), or N-(5-(phenylamino)-2,4-pentadienylidene)aniline was used as compound 4, respectively.

To a solution of compounds 5 (0.6 mmol) and 6 (0.6 mmol) in ethanol (10 mL) was added sodium acetic (1.8 mmol). The reaction was stirred under reflux at 80° C. for 2 h, cooled and concentrated. The residue was washed with diethyl ether, dissolved in DCM, washed with hydrochloric acid (0.1 M) and brine and concentrated. The residue was was purified on a RP-C18 column eluted with acetonitrile in water to afford the target compound E.

The following compounds were prepared according to the procedures described herein and Scheme 8.

Compound E1

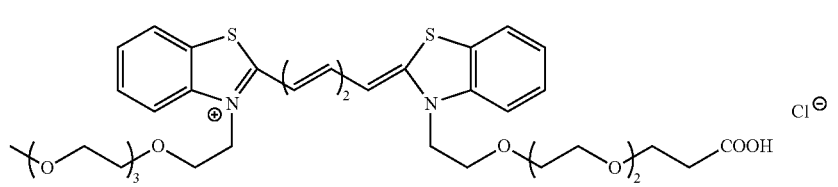

¹H NMR (500 MHz, CD₃OD) δ 7.87 (m, 2H), 7.65 (m, 4H), 7.52 (t, 2H, J=8.5 Hz), 7.37 (m, 2H), 6.52 (m, 3H), 4.54 (t, 3H, J=5.5 Hz), 3.92 (t, 3H, J=5.5 Hz), 3.67 (m, 3H), 3.44-3.52 (m, 24H), 2.50 (m, 2H); MS (m/z): 729.4.

Compound E2

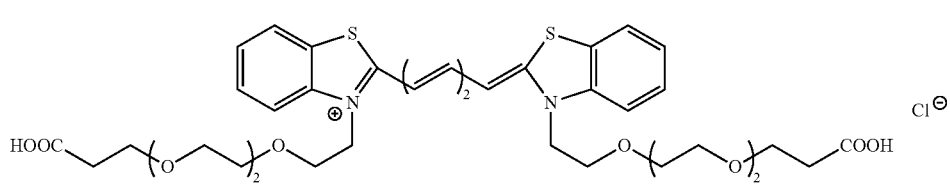

¹H NMR (500 MHz, CD₃OD) δ 7.90 (m, 2H), 7.76 (m, 2H), 7.61 (m, 3H), 7.52 (m, 3H), 7.49 (m, 2H), 6.52 (m, 1H), 4.51 (m, 2H), 3.91 (m, 2H), 3.46-3.66 (m, 28H); MS (m/z): 744.5.

Example 9

Preparation of a Compound of Formula F

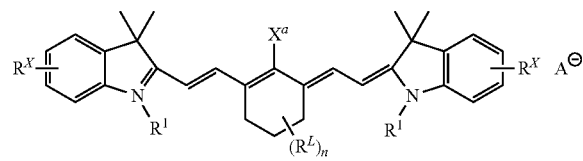
(F)

A compound of Formula F was prepared according to Scheme 9, wherein $R^c$ and $R^X$ are each as defined herein.

Scheme 9

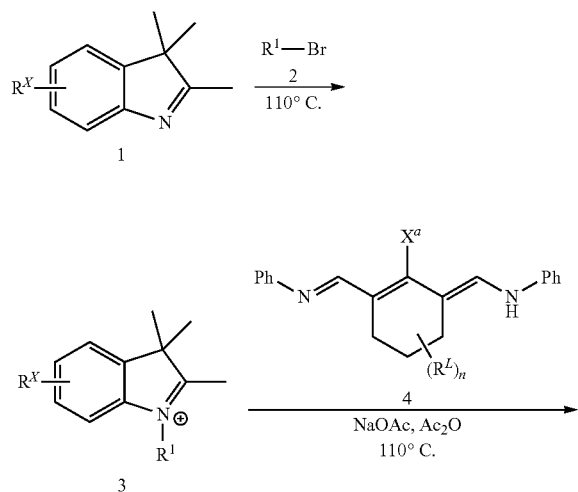

A mixture of compounds 1 and 2 was stirred at 110° C. under argon for 24 h, cooled to room temperature and triturated with diethyl ether (5 mL). The supernatant was decanted, and the residue was washed with diethyl ether and dried in vacuum to give 3.

Compounds 3 (0.4 mmol), 4 (0.2 mmol) and NaOAc (0.6 mmol) were dissvolved in acetic acid (5 mL) and reaction was stirred at 110° C. for 1 h under argon. The solution was concentrated, and the residue was dissolved in DCM, washed by hydrochloric acid (0.1 M) and brine and then concentrated. The residue was purified on a RP-C18 column eluted with acetonitrile in water to afford the target compound F.

The following compounds were prepared according to the procedures described herein and Scheme 9.

Compound F1

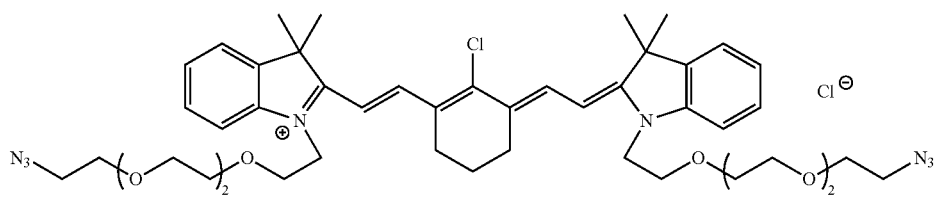

¹H NMR (500 MHz, CD₃OD) δ 8.44 (m, 2H), 7.51 (d, 2H, J=7.5 Hz), 7.42 (t, 2 H, J=8.0 Hz), 7.35 (d, 2H, J=8.0 Hz), 7.27 (m, 2H), 6.45 (d, 2H, J=13.5 Hz), 4.37 (m, 3H), 3.90 (m, 4H), 3.55-3.58 (m, 20H), 3.29 (m, 8H), 2.73(m, 3H), 1.73 (s, 12H); MS (m/z): 857.6.

Example 10

Preparation of a Compound of Formula G

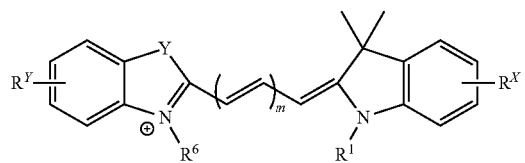
(G)

A compound of Formula G was prepared according to Scheme 10, wherein $R^1$, $R^6$, $R^X$, $R^Y$, and m are each as defined herein.

Scheme 10

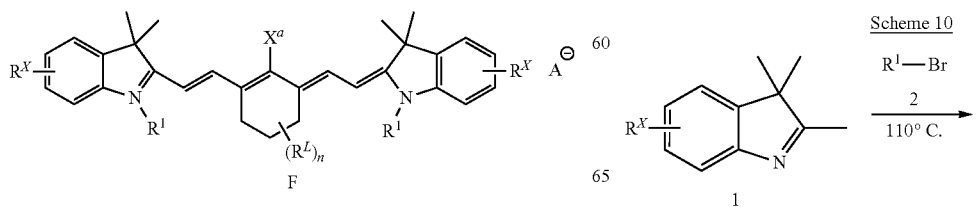

-continued

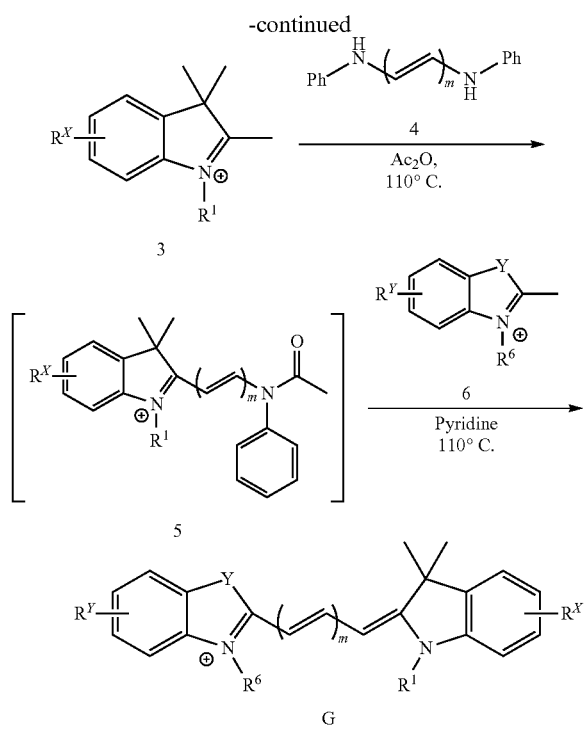

A mixture of compounds 1 and 2 was stirred under argon at 110° C. for 24 h, cooled and triturated with diethyl ether (5 mL). The supernatant was decanted, and the residue was washed with diethyl ether and dried in vacuum to yield compound 3.

A solution of compounds 3 (0.4 mmol) and 4 (0.4 mmol) in acetic anhydride (4 mL) was stirred at 110° C. for 40 min under argon. The reaction solution was cooled and concentrated to give the residue which was washed with diethyl ether to give intermediate 5.

Compounds 5 (0.4 mmol) and 6 (0.4 mmol) were dissolved in dry pyridine (4 mL) and the reaction was stirred at 110° C. for 40 min under argon. The solution was concentrated, and the residue was dissolved in DCM, washed by hydrochloric acid (0.1 M) and brine and then concentrated. The residue was purified on a RP-C18 column eluted with acetonitrile in water to afford the target compound G.

The following compounds were prepared according to the procedures described herein and Scheme 10.

Compound G1

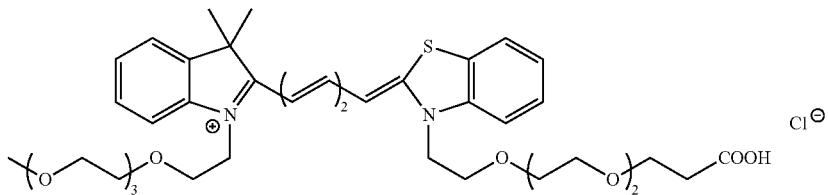

$^1$H NMR (500 MHz, CD$_3$OD) δ 7.93-7.96 (m, 3H), 7.81 (d, 1H), 7.61 (m, 1H), 7.48 (m, 1H), 7.38 (m, 1H), 7.31 (m, 1H), 7.12-7.16 (m, 2H), 6.78 (d, 1H), 6.53 (m, 1H), 6.14 (m, 1H), 4.68 (m, 1H), 4.17 (m, 2H), 3.95 (m, 2H), 3.83 (m, 2H), 3.65 (m, 3H), 3.44-3.54 (m, 24H), 1.68 (s, 6H); MS (m/z): 740.0.

Compound G2

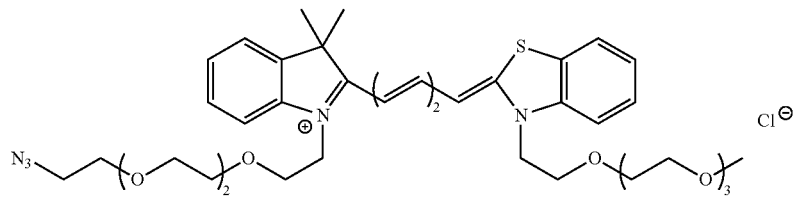

$^1$H NMR (500 MHz, CD$_3$OD) δ 7.91-7.98 (m, 3H), 7.78 (m, 1H), 7.61 (m, 1H), 7.48 (m, 1H), 7.38 (m, 1H), 7.31 (m, 1H), 7.13-7.18 (m, 2H), 6.75 (d, 1H), 6.55 (d, 1H), 6.18 (d, 1H), 4.67 (m, 2H), 4.18 (m, 2H), 3.94 (m, 2H), 3.83 (m, 2H), 3.65 (m, 3H), 3.47-3.59 (m, 24H), 1.68 (s, 6H); MS (m/z): 736.8.

Example 11
Labeling of a Biomolecule
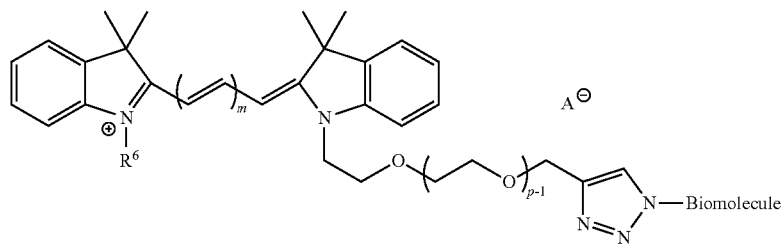
A labeled biomolecule is prepared according to Scheme 11, wherein $R^6$, m, and p are each as defined herein.
Scheme 11
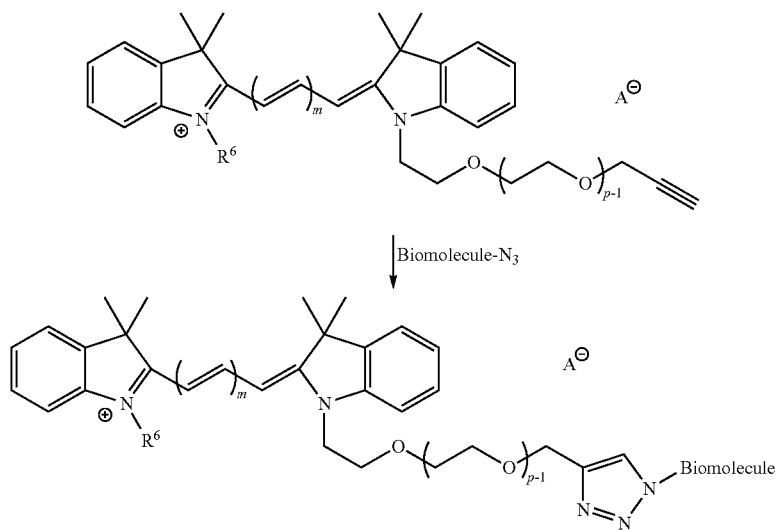
Example 12
Labeling of a Biomolecule
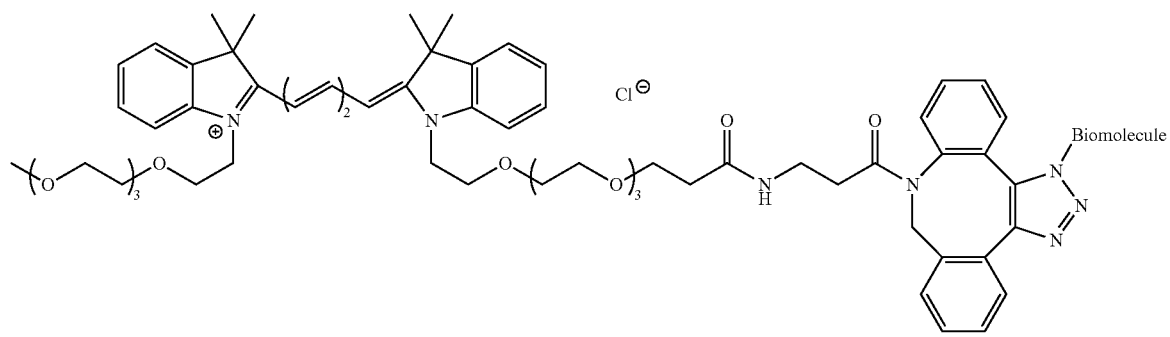
A labeled biomolecule is prepared according to Scheme 12.

Scheme 12
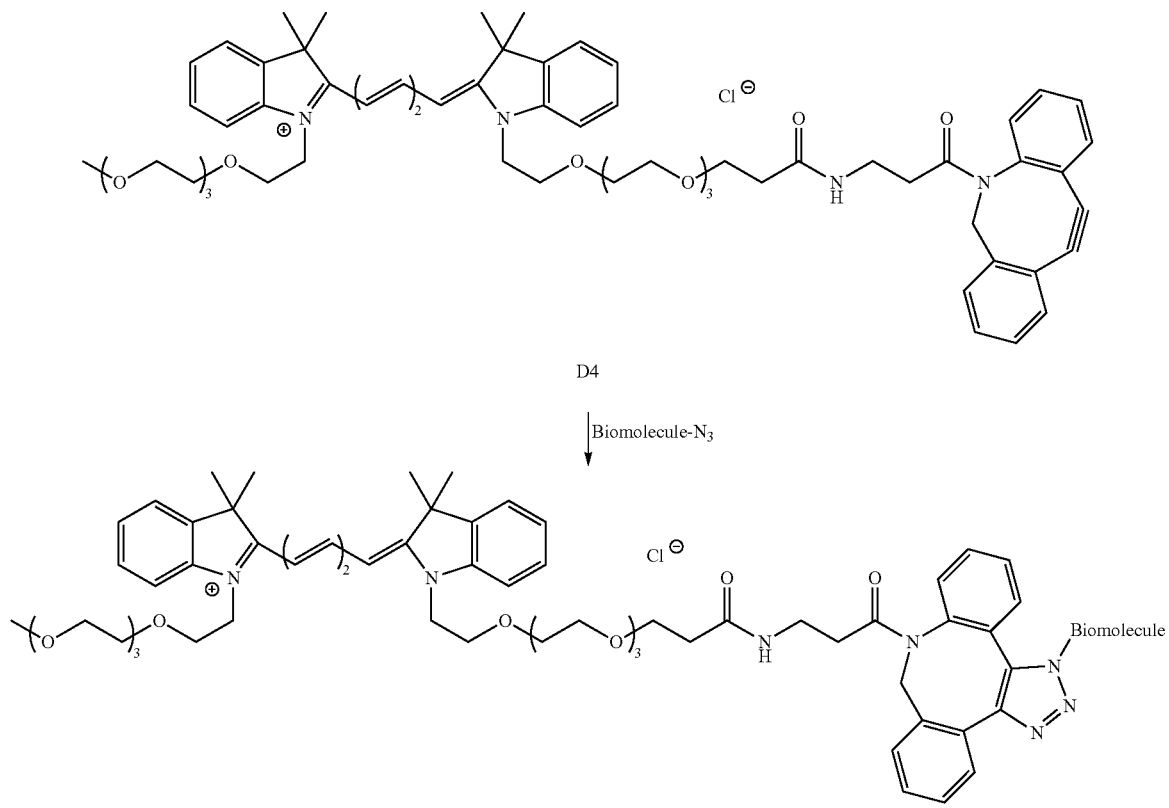
D4
Example 13
Labeling of a Biomolecule
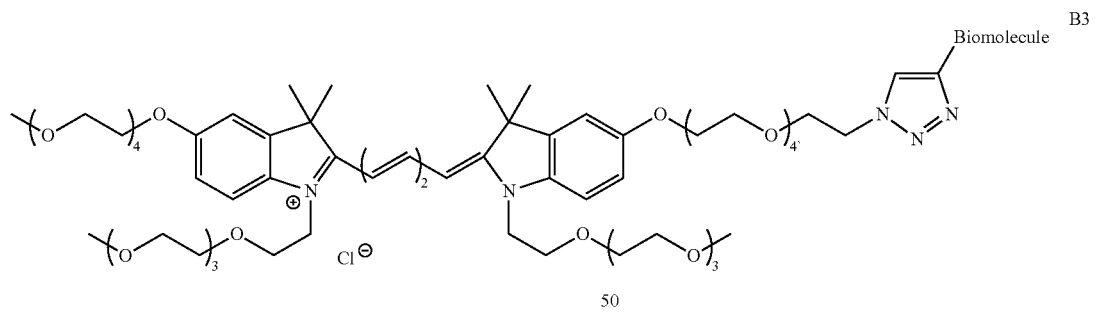
A labeled biomolecule is prepared according to Scheme 13.
Scheme 13
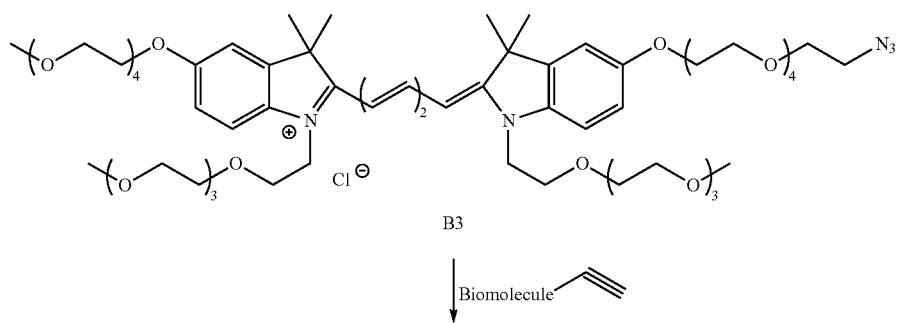

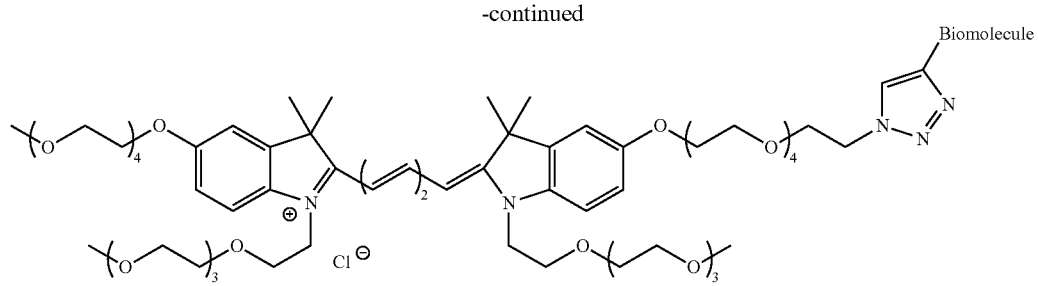

Example 14

Labeling of a Biomolecule

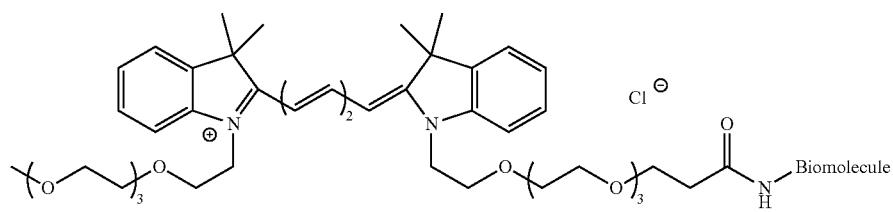

A labeled biomolecule is prepared according to Scheme 14.

Scheme 14

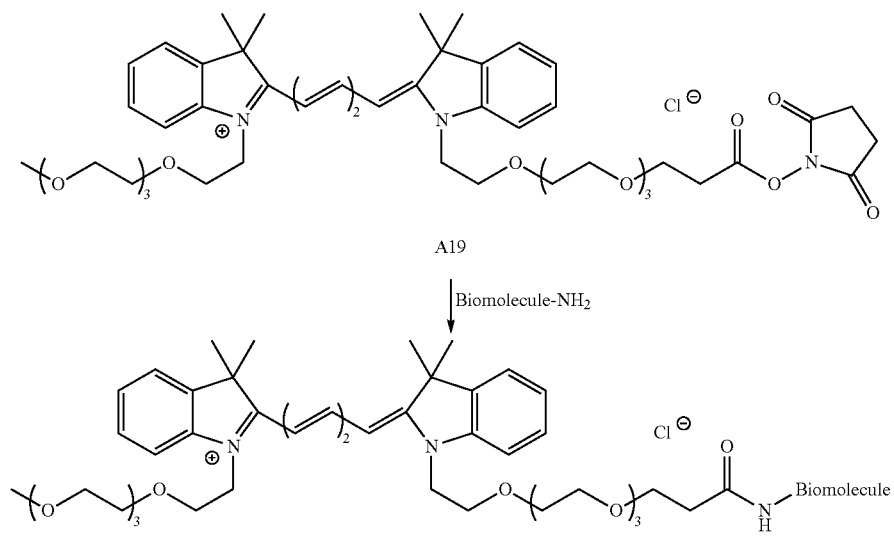

Example 15

Photophysical Properties of Select Dyes

The photophysical properties of a variety of cyanine dyes in dimethyl sulfoxide has been measured by the DU 800 spectrophotometer. The spectral results, with respect to the absorption, emission, and extinction coefficients, are summarized in Table below.

| No. | Excitation (nm) | Emission (nm) | Extinction Coefficient |
|---|---|---|---|
| A2  | 649 | 667 | $1.63 \times 10^5$ |
| A10 | 650 | 691 | $6.57 \times 10^4$ |
| A19 | 649 | 667 | $2.32 \times 10^5$ |
| A20 | 649 | 667 | $1.70 \times 10^5$ |
| A24 | 752 | 785 | $9.79 \times 10^4$ |
| A28 | 649 | 667 | $1.16 \times 10^5$ |
| B1  | 649 | 699 | $6.12 \times 10^4$ |
| B3  | 672 | 695 | $2.2 \times 10^5$ |

-continued

| No. | Excitation (nm) | Emission (nm) | Extinction Coefficient |
|-----|-----------------|---------------|------------------------|
| B8  | 565 | 598 | $5.95 \times 10^4$ |
| C1  | 649 | 667 | $1.02 \times 10^5$ |
| D3  | 649 | 667 | $6.94 \times 10^4$ |
| D4  | 649 | 667 | $6.42 \times 10^4$ |
| D5  | 649 | 667 | $9.16 \times 10^4$ |
| E1  | 661 | 682 | $7.11 \times 10^4$ |
| E2  | 661 | 682 | $7.31 \times 10^4$ |
| F1  | 785 | 817 | $1.16 \times 10^5$ |
| G1  | 661 | 685 | $7.65 \times 10^4$ |
| G2  | 652 | 671 | $4.23 \times 10^4$ |

The results in above table show that the length of the cyanine bridge is correlated with the wavelength, and for each vinyl addition to the polymethine chain the wavelength increases by roughly 100 nm. For eample, excitation of cyanine dyes (n=2) range from 649 nm to 672 nm, while the cyanine dye B8 (n=1) had a less excitation at 565 nm and an emission at 598 nm, and the enhanced excitation and emission of A24 (n=3) was found to be 752 nm and 785 nM respectively.

The incorporation of a cyclohexene ring in the center of the polymethine chain results in compound F1 (n=3), with highest absorption of 785 nm and emission of 817 nm. It has been considered that the six-membered cyclohexene could stabilize the conformation to the molecule and thus enhance the photophysical properties.

The sulfur containing cyanine dyes E1, E2, G1 and G2 affect the wavelength, but to a lesser degree than the chromophore length.

Example 16

Solubility of Select Dyes

The comparative solubility of select cyanine dyes is shown below.

| Compound | Aqueous solubility |
|----------|--------------------|
| 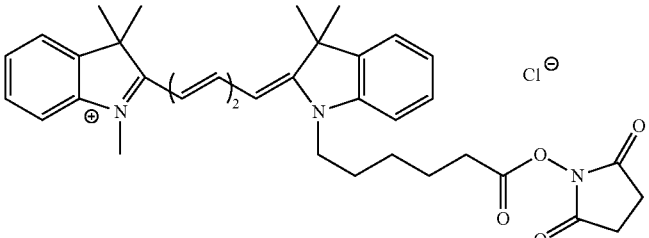<br>I | <1 mM |
| 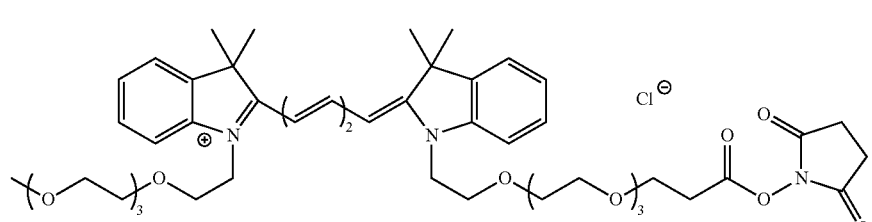<br>A19 | 166.6 mM |
| 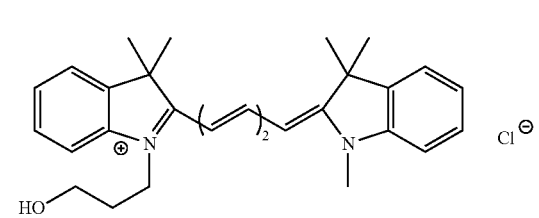<br>II | <1 mM |
| 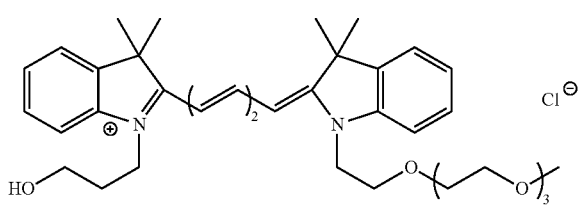<br>A14 | 71.4 mM |

| Compound | Aqueous solubility |
|---|---|
| 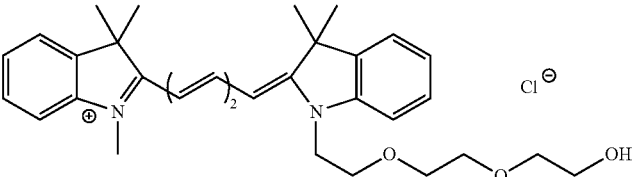 A15 | 62.5 mM |

The labeling of cyanine dyes to biomolecules involves covalent conjugations in aqueous buffer solutions under mild conditions. To improve the water solubility, PEGylation of the cyanine dyes has been considered to be a viable strategy in many cases.

The results in the above table show that the addition of PEG increases the solubility of the dye. For example, The dye I with N-methyl and N'-hydroxysuccinimidyl esters is poorly soluable in water and precipitating at concentration of 1 mM at room temperature, while incorporation of N-PEG4-methyl and N'-PEG4-OSu results in the dye A19 which shows a significant improvement in water solubility at maximum concentration of 166.6 mM. Similarly, compared to the non-PEG dye II, N-PEG4-methyl in A14 and N'-PEG-2-alcohol in A15 increase dye solubility with maximum concentrations of 71.4 mM and 62.5 mM respectively.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula I:

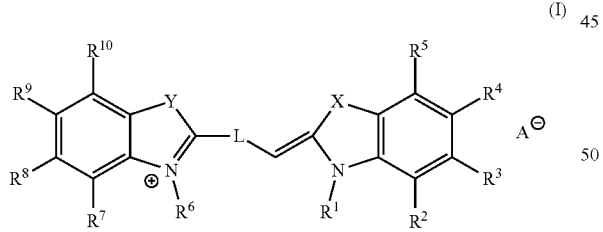

(I)

or a tautomer or a mixture of two or more tautomers thereof; or a pharmaceutically acceptable solvate or hydrate thereof; wherein:

A is an anion bearing a negative charge;
L is

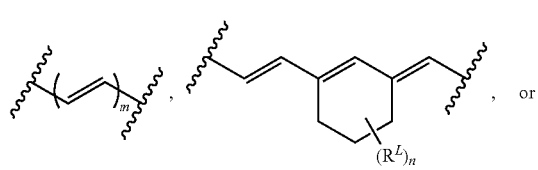, or

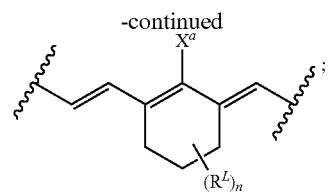

wherein:
each $R^L$ is independently (a) hydrogen, deuterium, azido, cyano, halo, nitro, oxo, sulfo, —$OPO_3H_2$, or $PO_3H_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$;

$X^a$ is (a) hydrogen, deuterium, azido, cyano, halo, nitro, oxo, sulfo, $OPO_3H_2$, or —$PO_3H^2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl, each of which is optionally substituted with one or more substituents Q; (c) —$C(R^{1a}R^{1b})$, —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$; (d) —$(CH_2CH_2O)_p$-$L^1$-$Z^1$, —$(CH_2CH_2O)_p$—COOH, —$(CH_2CH_2O)_p$—$N_3$, —$(CH_2CH_2O)_p$—OH, —$(CH_2CH_2O)_p$-alkyne, —$(CH_2CH_2O)_p$-biotin, —$(CH_2CH_2O)_p$-NHS ester, —$(CH_2CH_2O)_p$-amine, —$(CH_2CH_2O)_p$-DBCO, —$(CH_2CH_2O)_p$-Fmoc, —$(CH_2CH_2O)_p$-aldehyde, —$(CH_2CH_2O)_p$-phosphonate, —$(CH_2CH_2O)_p$-tosylate, —$(CH_2CH_2O)_p$-FPF ester, —$(CH_2CH_2O)_p$-Boc, —$(CH_2CH_2O)_p$-aminooxy, —$(CH_2CH_2O)_p$-bromo, —$(CH_2CH_2O)_p$-mal, or -$(CH_2CH_2O)_p$-propargyl; or (e) carboxycylic acid, amine, azide, DBCO, hydrazide, maleimide, NHS ester, TCO, tetrazine, or biotin;

m is an integer of 1, 2, or 3; and n is an integer of 0, 1, 2, 3, 4, 5, 6, or 7;

X and Y are each independently $C(R^{Xa}R^{Xb})$, O, S, or $NR^{Xc}$; wherein:

$R^{Xa}$ and $R^{Xb}$ are each independently (a) hydrogen or deuterium; or (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; and $R^{Xc}$ is (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; or (c) —C(O)$R^{1a}$, —C(O)O$R^{1a}$, —C(O)$NR^{1b}R^{1c}$, —C($NR^{1a}$)$NR^{1b}R^{1c}$, —S(O)$R^{1a}$, —S(O)$_2R^{1a}$, —S(O)$NR^{1b}R^{1c}$, or —S(O)$_2NR^{1b}R^{1c}$;

$R^1$ is (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O)O$R^{1a}$, —C(O)$NR^{1b}R^{1c}$, —C($NR^{1a}$)$NR^{1b}R^{1c}$, —S(O)$R^{1a}$, —S(O)$_2R^1$, —S(O)$NR^{1b}R^{1c}$, or —S(O)$_2NR^{1b}R^{1c}$; or (d) —(CH$_2$CH$_2$O)$_p$-L$^1$-Z$^1$; wherein:

L$^1$ is $C_{1-10}$ alkylene, $C_{1-10}$ heteroalkylene, $C_{2-10}$ alkenylene, $C_{2-10}$ alkynylene, $C_{3-15}$ cycloalkylene, —$C_{1-10}$ heteroalkylene—$C_{3-15}$ cycloalkylene, $C_{6-20}$ arylene, $C_{7-20}$ aralkylene, heteroarylene, or heterocyclylene;

Z$^1$ is (a) amino, azido, chloro, bromo, iodo, or thiol; (b) N-maleimido, N-3,4-dibromo-maleimido, $C_{2-6}$ alkynyl, heterocyclyl containing a carbon-carbon triple, acrylyl, 3-sulfo-N-succinimidyloxycarbonyl, tetrafluorophenoxycarbonyl, pentofluorophenoxycarbonyl, $C_{2-6}$ alkynyloxy, $C_{3-15}$ cycloalkyloxy containing a carbon-carbon triple, $C_{6-20}$ aryloxy containing a carbon-carbon triple, or heterocyclyloxy containing a carbon-carbon triple; (c) —OP(O$R^{1a}$)($NR^{1b}R^{1c}$), —OP(($NR^{1b}R^{1c}$)$_2$, —OS(O)$_2R^{1a}$, or —S—S$R^{1a}$; or (d) Z$^6$; and p is an integer of 1 to 50;

$R^2$, $R^3$, $R^4$, $R^5$, $R^7$, $R^8$, $R^9$, and $R^{10}$ are each independently (a) hydrogen, deuterium, azido, cyano, halo, nitro, sulfo, —OPO$_3$H$_2$, or —PO$_3$H$_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O)O$R^{1a}$, —C(O)$NR^{1b}R^{1c}$, —C($NR^{1a}$)$NR^{1b}R^{1c}$, —O$R^{1a}$, —OC(O)$R^{1a}$, —OC(O)O$R^{1a}$, —OC(O)$NR^{1b}R^{1c}$, —OC(=$NR^{1a}$)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)O$R^{1d}$, —$NR^{1a}$C(O)$NR^{1b}R^{1c}$, —$NR^{1a}$C(=$NR^{1d}$)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2NR^{1b}R^{1c}$, —S$R^{1a}$, —S(O)$R^{1a}$, —S(O)$_2R^{1a}$, —S(O)$NR^{1b}R^{1c}$, or —S(O)$_2NR^{1b}R^{1c}$, (d) $R^2$ and $R^3$, $R^4$ and $R^5$, $R^7$ and $R^8$, or $R^9$ and $R^{10}$, each pair together with the carbon atoms to which they are attached independently form $C_{3-15}$ cycloalkyl, $C_{6-20}$ aryl, heteroaryl, or heterocyclyl; (e) $R^3$ and $R^4$, or $R^8$ and $R^9$, each pair together with the carbon atoms to which they are attached independently form $C_{3-15}$ cycloalkyl, $C_{6-20}$ aryl, heteroaryl, or heterocyclyl; or (f) —O(CH$_2$CH$_2$O)$_r$-L$^r$-Z$^r$, with the proviso that when $R^c$ is not —(CH$_2$CH$_2$O)$_p$-L$^1$—Z$^1$, at least one of $R^1$, $R^2$, $R^3$, $R^4$, $R^5$, $R^7$, $R^8$, $R^9$, and $R^{10}$ is —O(CH$_2$CH$_2$O)$_r$—L$^r$-Z$^r$; wherein:

L$^r$ is $C_{1-10}$ alkylene, $C_{1-10}$ heteroalkylene, $C_{2-10}$ alkenylene, $C_{2-10}$ alkynylene, $C_{3-15}$ cycloalkylene, $C_{1-10}$ heteroalkylene-$C_{3-15}$ cycloalkylene, $C_{6-20}$ arylene, $C_{7-20}$ aralkylene, heteroarylene, or heterocyclylene;

Z$^r$ is (a) hydrogen, deuterium, halo, cyano, nitro, sulfo, —OPO$_3$H$_2$, or —PO$_3$H$_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O)O$R^{1a}$, —C(O)$NR^{1b}R^{1c}$, —C($NR^{1a}$)$NR^{1b}R^{1c}$, —O$R^{1a}$, —OC(O)$R^{1a}$, —OC(O)O$R^{1a}$, —OC(O)$NR^{1b}R^{1c}$, —OC(=$NR^{1a}$)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)O$R^{1d}$, —$NR^{1a}$C(O)$NR^{1b}R^{1c}$, —$NR^{1a}$C(=$NR^{1d}$)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2NR^{1b}R^{1c}$, —S$R^{1a}$, —S(O)$R^{1a}$, —S(O)$_2R^{1a}$, —S(O)$NR^{1b}R^{1c}$, or —S(O)$_2NR^{1b}R^{1c}$; or (d) Z$^1$; and r is an integer of 1 to 50;

$R^6$ is (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O)O$R^{1a}$, —C(O)$NR^{1b}R^{1c}$, —C($NR^{1a}$)$NR^{1b}R^{1c}$, —S(O)$R^{1a}$, —S(O)$_2R^{1a}$, —S(O)$NR^{1b}R^{1c}$; or (d) —(CH$_2$CH$_2$O)$_q$-L$^6$-Z$^6$; wherein:

L$^6$ is $C_{1-10}$ alkylene, $C_{1-10}$ heteroalkylene, $C_{2-10}$ alkenylene, $C_{2-10}$ alkynylene, $C_{3-15}$ cycloalkylene, $C_{6-20}$ arylene, $C_{7-20}$ aralkylene, heteroarylene, or heterocyclylene;

Z$^6$ is (a) hydrogen, deuterium, halo, cyano, nitro, sulfo, —OPO$_3$H$_2$, or —PO$_3$H$_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) —C(O)$R^{1a}$, —C(O)O$R^{1a}$, —C(O)$NR^{1b}R^{1c}$, —C($NR^{1a}$)$NR^{1b}R^{1c}$, —O$R^{1a}$, —OC(O)$R^{1a}$, —OC(O)O$R^{1a}$, —OC(O)$NR^{1b}R^{1c}$, —OC(=$NR^{1a}$)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}$C(O)$R^{1d}$, —$NR^{1a}$C(O)O$R^{1d}$, —$NR^{1a}$C(O)$NR^{1b}R^{1c}$, —$NR^{1a}$C(=$NR^{1d}$)$NR^{1b}R^{1c}$, —$NR^{1a}$S(O)$R^{1d}$, —$NR^{1a}$S(O)$_2R^{1d}$, —$NR^{1a}$S(O)$NR^{1b}R^{1c}$, —$NR^{1a}$S(O)$_2NR^{1b}R^{1c}$, —S$R^{1a}$, —S(O)$R^{1a}$, —S(O)$_2R^{1a}$, —S(O)$NR^{1b}R^{1c}$, or —S(O)$_2NR^{1b}R^{1c}$; or (d) Z$^1$; and q is an integer of 1 to 50; and each $R^{1a}$, $R^{1b}$ $R^{1c}$, and $R^{1d}$ is independently (a) hydrogen or deuterium; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl; (c) $R^{1a}$ and $R^{1c}$ together with the C and N atoms to which they are attached form heterocyclyl; or (d) $R^{1b}$ and $R^{1c}$ together with the N atom to which they are attached form heteroaryl or heterocyclyl;

wherein each alkyl, alkylene, heteroalkylene, alkenyl, alkenylene, alkynyl, alkynylene, cycloalkyl, cycloalkylene, aryl, arylene, aralkyl, aralkylene, heteroaryl, heteroarylene, heterocyclyl, heterocyclylene, alkynyloxy, cycloalkyloxy, aryloxy, and heterocyclyloxy is optionally substituted with one or more substituents Q, where each Q is independently selected from (a) deuterium, azido, cyano, halo, nitro, oxo, sulfo, —OPO$_3$H$_2$, and —PO$_3$H$_2$; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each of which is further optionally substituted with one or more, in one embodiment, one, two, three, or four, substituents $Q^a$; or (iii) R$^b$ and R$^c$ together with the N atom to which they are attached form heteroaryl or heterocyclyl, each of which is further optionally substituted with one or more, in one embodiment, one, two, three, or four, substituents $Q^a$;

wherein each $Q^a$ is independently selected from the group consisting of (a) deuterium, azido, cyano, halo, nitro, oxo, sulfo, —OPO$_3$H$_2$, and —PO$_3$H$_2$; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$;

wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

2. The compound of claim 1, having the structure of Formula II:

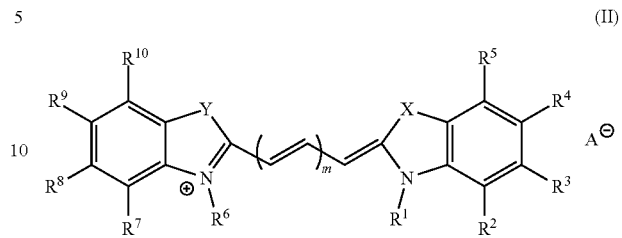

or a tautomer or a mixture of two or more tautomers thereof or a pharmaceutically acceptable solvate or hydrate thereof.

3. The compound of claim 1, having the structure of Formula III:

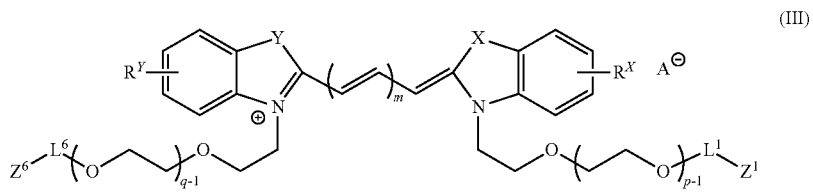

or a tautomer or a mixture of two or more tautomers thereof; or a pharmaceutically acceptable solvate or hydrate thereof; wherein:

R$^X$ and R$^Y$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

4. The compound of claim 1, having the structure of Formula IV:

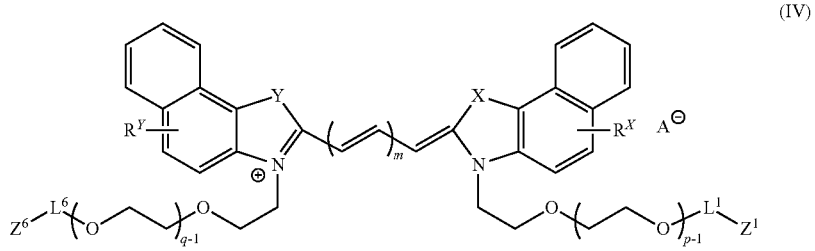

or a tautomer or a mixture of two or more tautomers thereof; or a pharmaceutically acceptable solvate or hydrate thereof; wherein:

R$^X$ and R$^Y$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, $C_{3-15}$ cycloalkyl, $C_{6-20}$ aryl, $C_{7-20}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

5. The compound of claim 1, having the structure of Formula V:

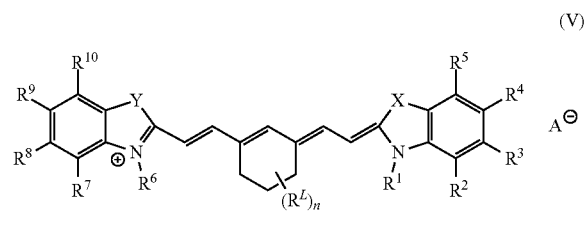

(V)

or a tautomer or a mixture of two or more tautomers thereof; or a pharmaceutically acceptable solvate or hydrate thereof.

6. The compound of claim 1, having the structure of Formula IX:

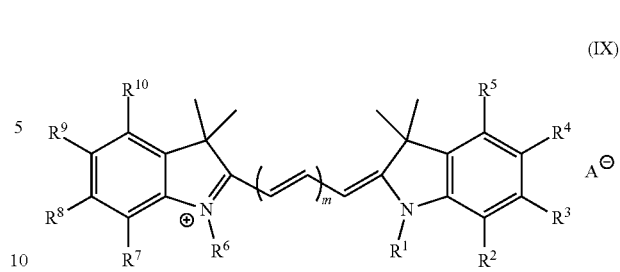

(IX)

or a tautomer or a mixture of two or more tautomers thereof; or a pharmaceutically acceptable solvate or hydrate thereof.

7. The compound of claim 1, having the structure of Formula XII:

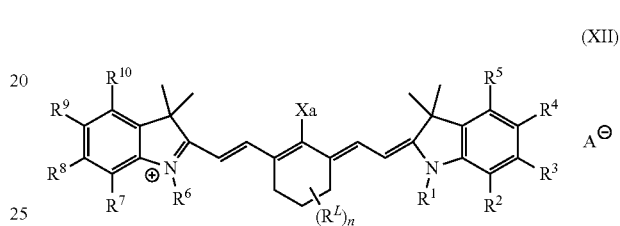

(XII)

or a tautomer or a mixture of two or more tautomers thereof; or a pharmaceutically acceptable solvate or hydrate thereof.

8. The compound of claim 1, selected from:

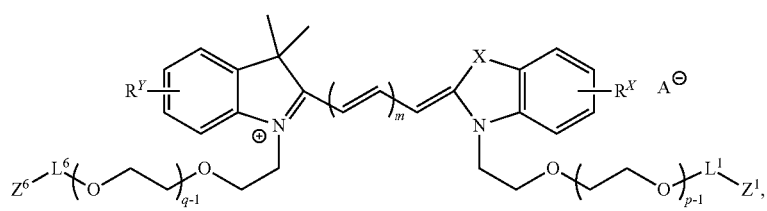

XV

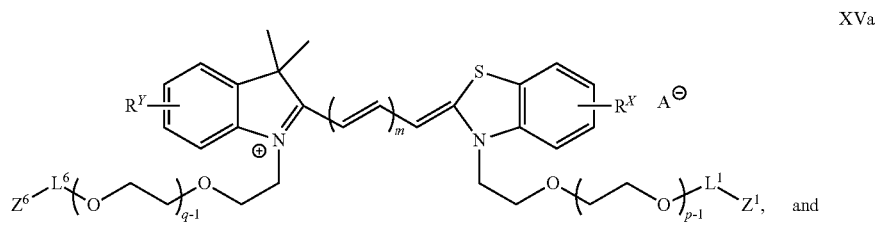

XVa

, and

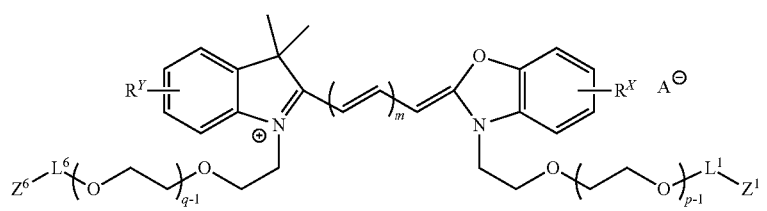

XVb or a tautomer or a mixture of two or more tautomers thereof;
or a pharmaceutically acceptable solvate or hydrate thereof;
wherein:
R$^X$ and R$^Y$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

9. The compound of claim 1, selected from:

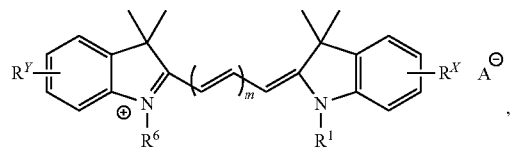
XVI

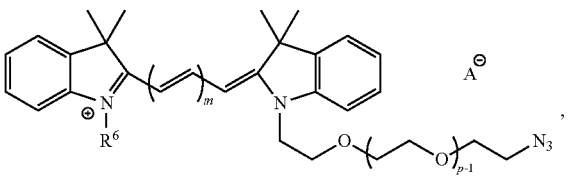
XVIa

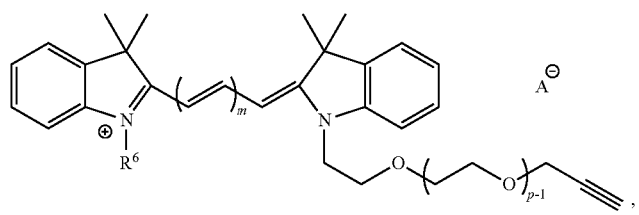
XVIb

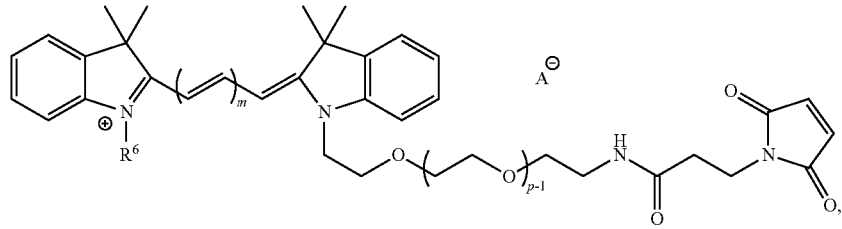
XVIc

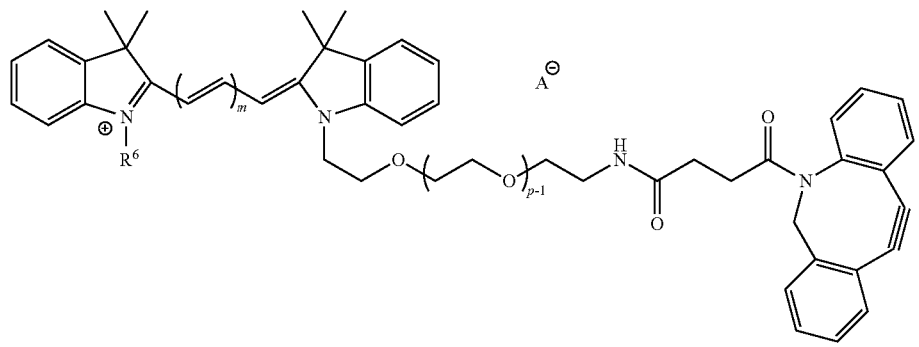
XVId

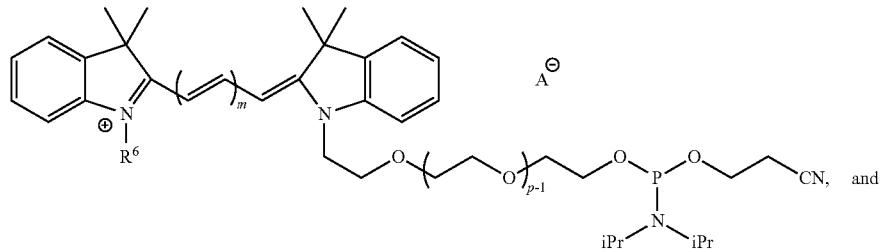
XVIe and

-continued

XVIf
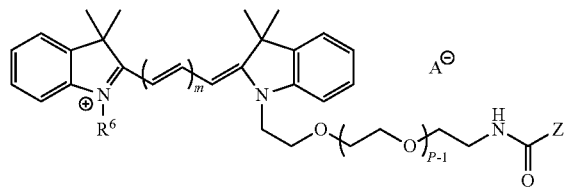

XVg
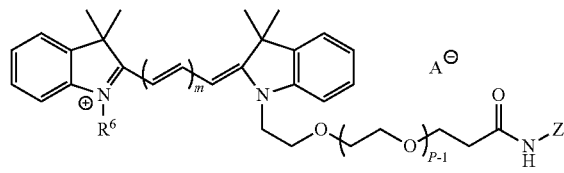

or a tautomer or a mixture of two or more tautomers thereof; or a pharmaceutically acceptable solvate or hydrate thereof; wherein:

$R^X$ and $R^Y$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and wherein:

Z is (a) hydrogen, deuterium, halo, O, S, N, or Se; (b) $Z^1$ or $Z^6$; or (c) $R^{Xc}Z^1$, $R^{Xa}R^{Xc}Z^1$, $R^{Xc}Z^6$, $R^{Xa}R^{Xc}Z^6$, $C(R^{Xa}R^{Xb})$, or $NR^{Xc}$.

10. The compound of claim 1, selected from:

XIX
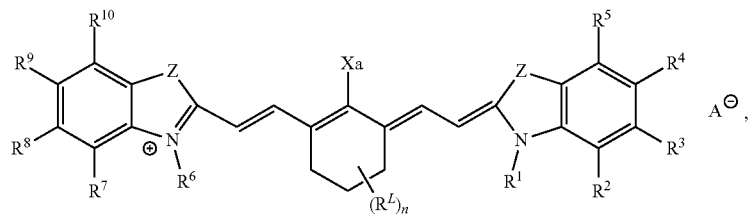

XIXa
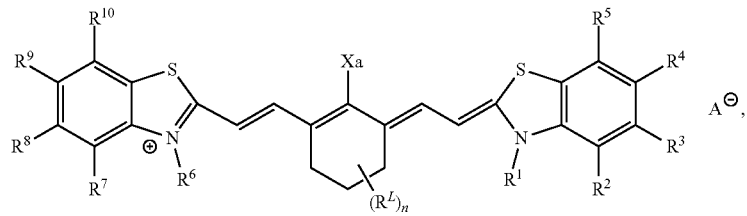

XIXb
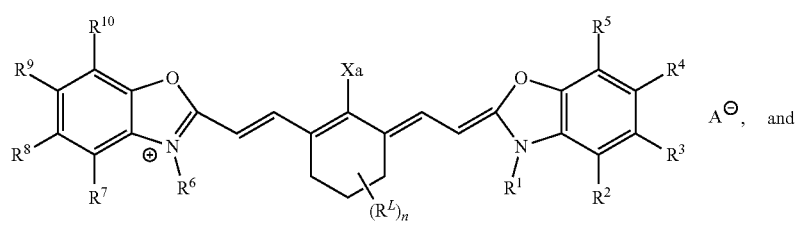

$A^\ominus$, and

XIXc

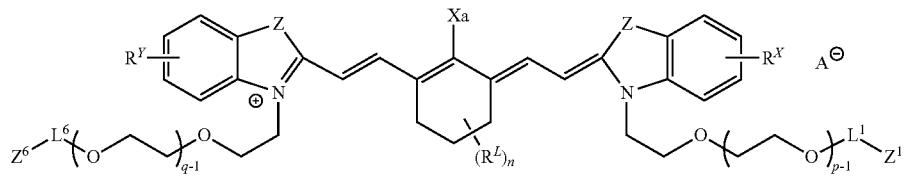

or a tautomer or a mixture of two or more tautomers thereof; or a pharmaceutically acceptable solvate or hydrate thereof; wherein:

$R^X$ and $R^Y$ are each independently (a) hydrogen, deuterium, azido, cyano, halo, nitro, sulfo, —$OPO_3H_2$, or —$PO_3H_2$; (b) $C_{1-10}$ alkyl, $C_{2-10}$ alkenyl, $C_{2-10}$ alkynyl, $C_{3-15}$ cycloalkyl, $C_{6-20}$ aryl, $C_{7-20}$ aralkyl, heteroaryl, or heterocyclyl, each of which is optionally substituted with one or more substituents Q; or (c) —$C(O)R^{1a}$, —$C(O)OR^{1a}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$; and wherein:

Z is (a) hydrogen, deuterium, halo, O, S, N, or Se; (b) $Z^1$ or $Z^6$; or (c) $R^{Xc}Z^1$, $R^{Xa}R^{Xc}Z^1$, $R^{Xc}Z^6$, $R^{Xa}R^{Xc}Z^6$, $C(R^{Xa}R^{Xb})$, or $NR^{Xc}$.

11. The compound of claim 1, selected from:

XX

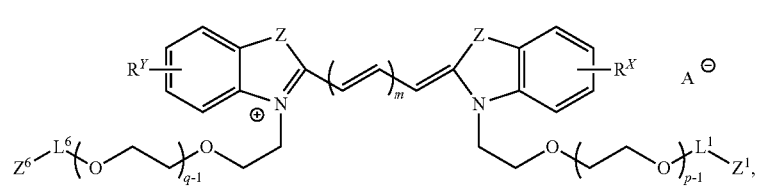

XXa

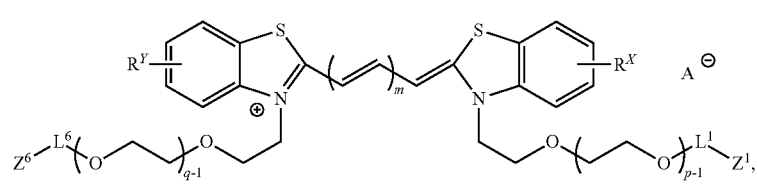

XXb

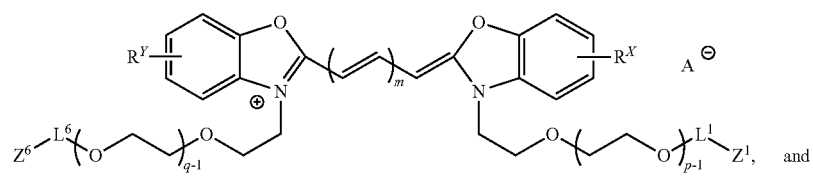

and

XXc

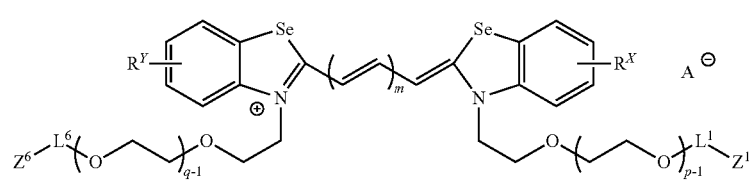

or a tautomer or a mixture of two or more tautomers thereof; or a pharmaceutically acceptable solvate or hydrate thereof; wherein:

$R^X$ and $R^Y$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; or (c) —C(O)R$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and wherein:

Z is (a) hydrogen, deuterium, halo, O, S, N, or Se; (b) $Z^1$ or $Z^6$; or (c) $R^{Xc}Z^1$, $R^{Xa}R^{Xc}Z^1$, $R^{Xc}Z^6$, $R^{Xa}R^{Xc}Z^6$, C($R^{Xa}R^{Xb}$), or NR$^{Xc}$.

12. The compound of claim 1, selected from:

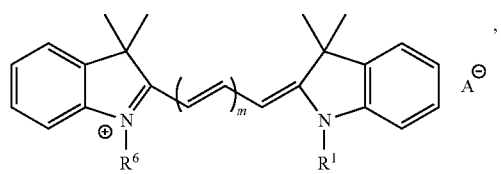

A

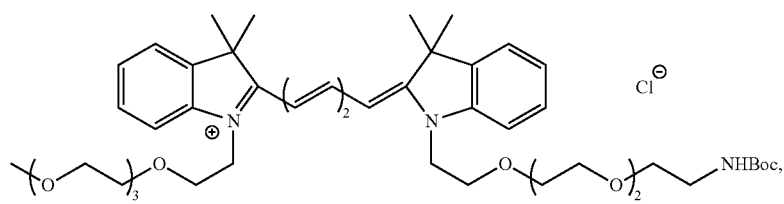

A1

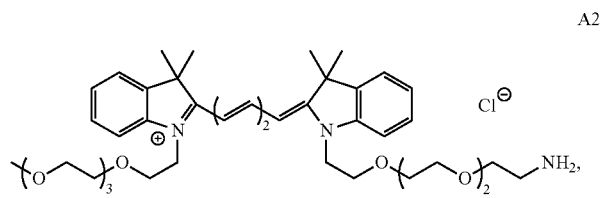

A2

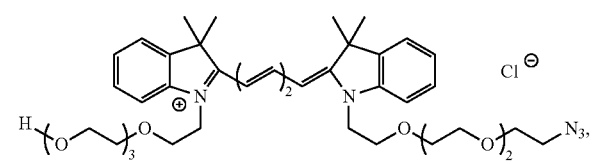

A3

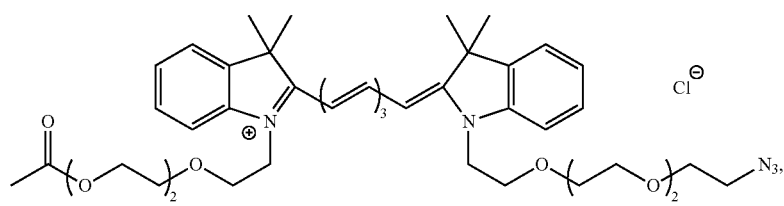

A4

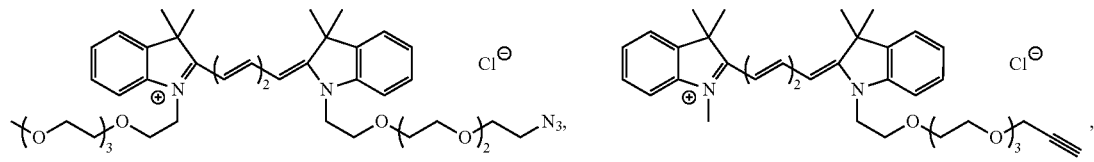

A5

A6

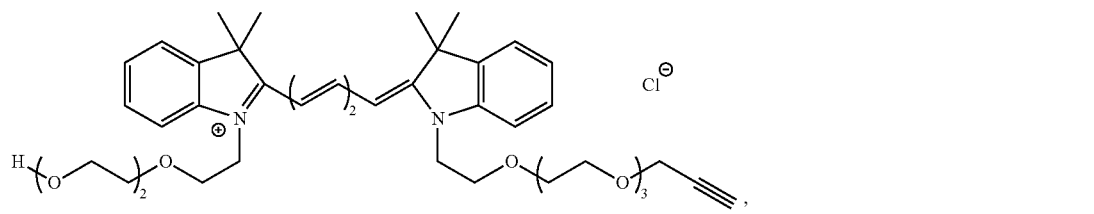

A7

-continued
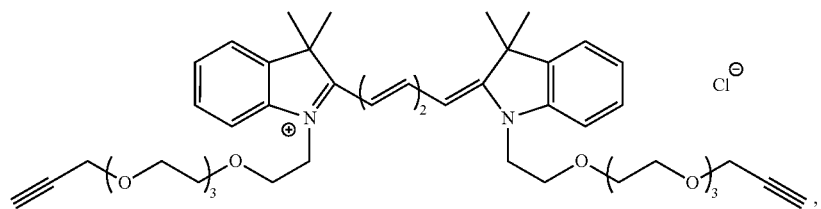
A8
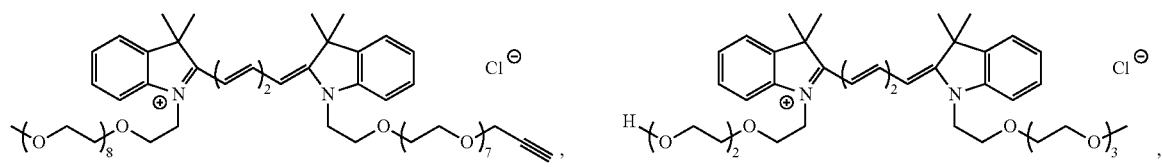
A9 A10
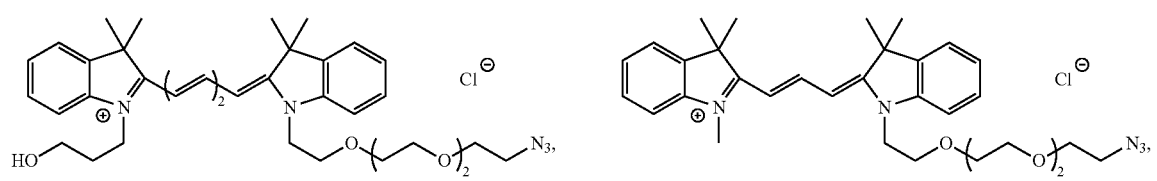
A11 A12
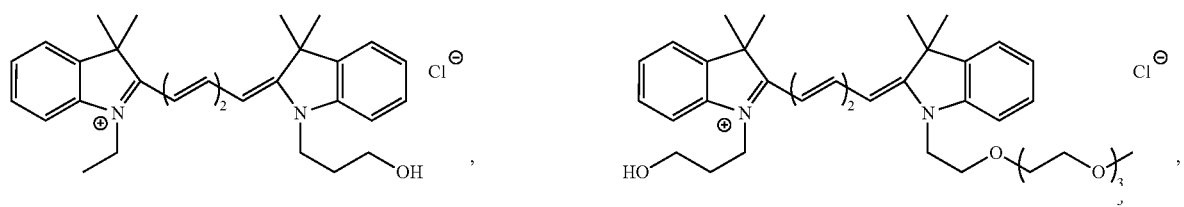
A13 A14
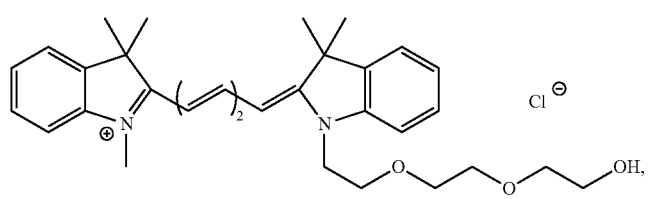
A15
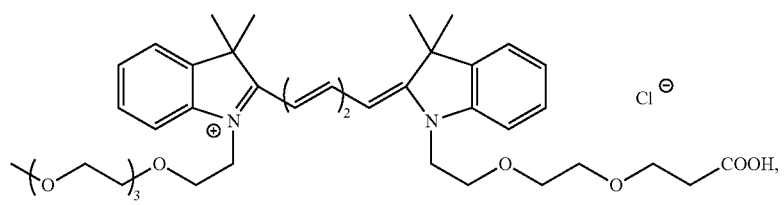
A16
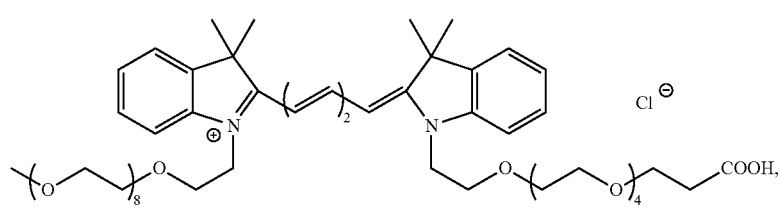
A17

-continued
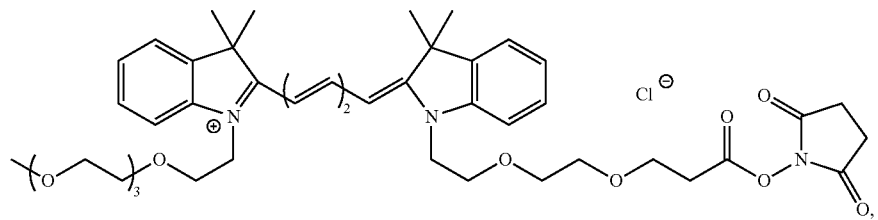
A18
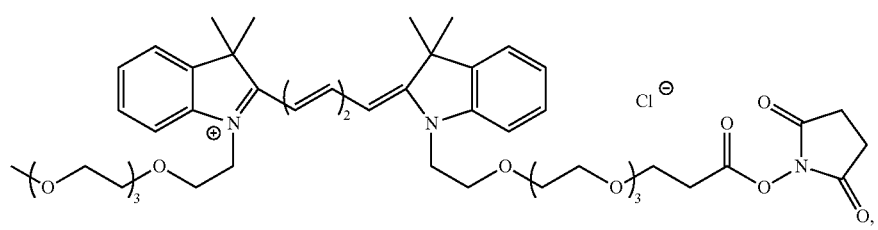
A19
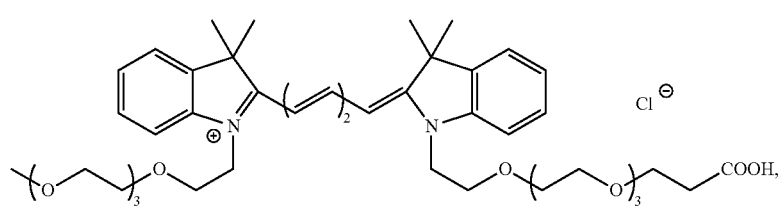
A20
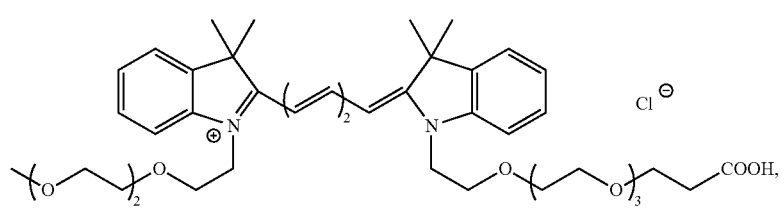
A21
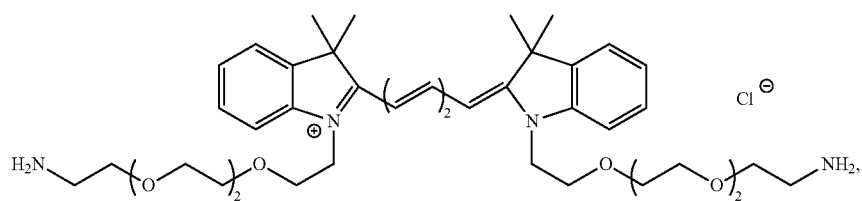
A22
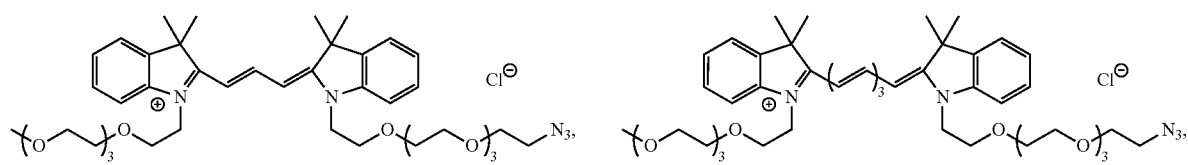
A23 A24
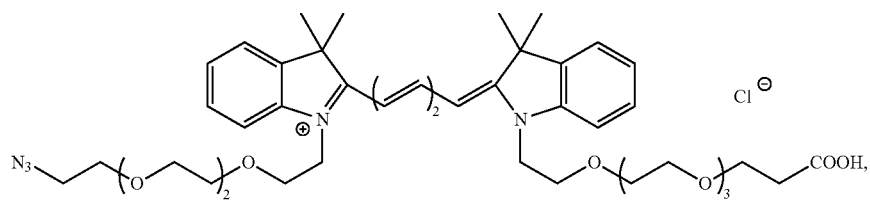
A25

-continued
A26
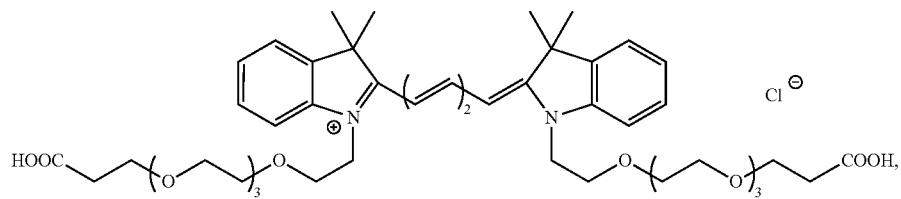
A27
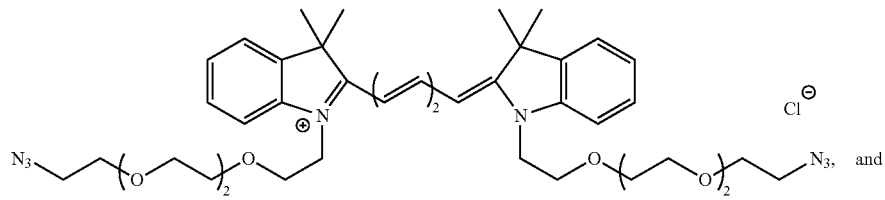
and
A28
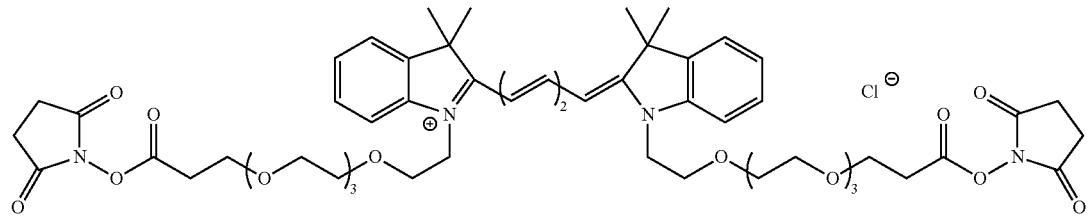
and tautomers and mixtures of two or more tautomers thereof; and pharmaceutically acceptable solvates and hydrates thereof.
13. The compound of claim 1, selected from:
B
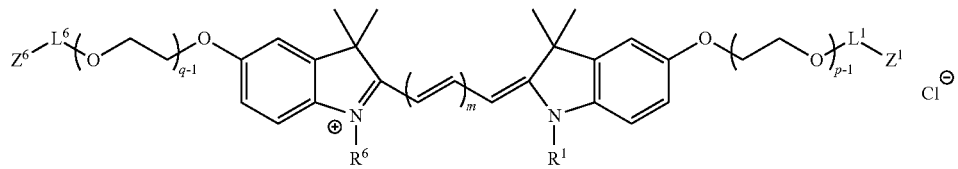
B1
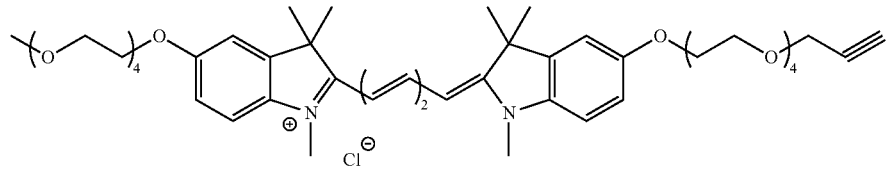
B2
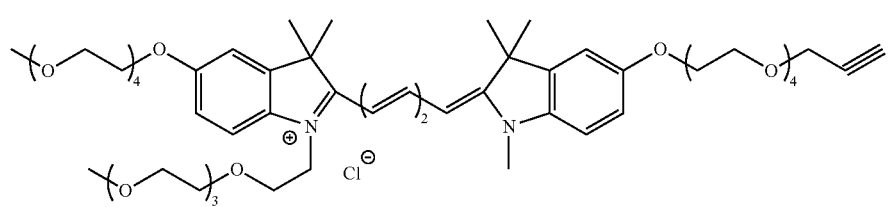
B3
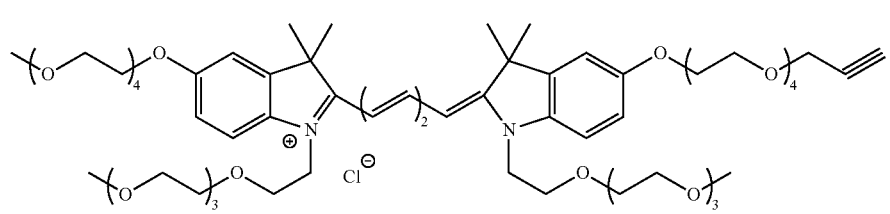

B4
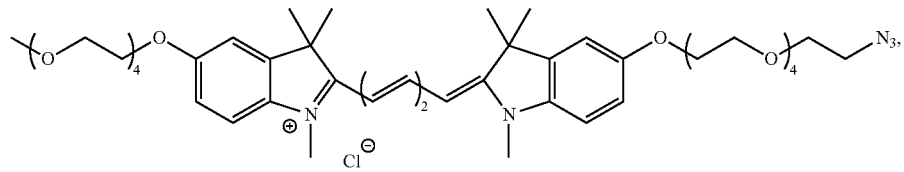
B5
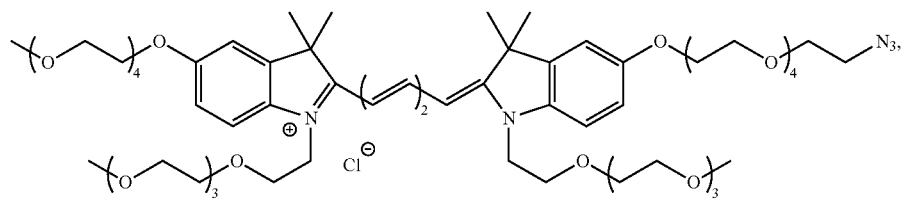
B6
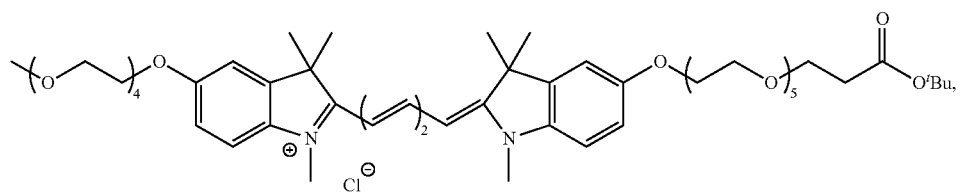
B7
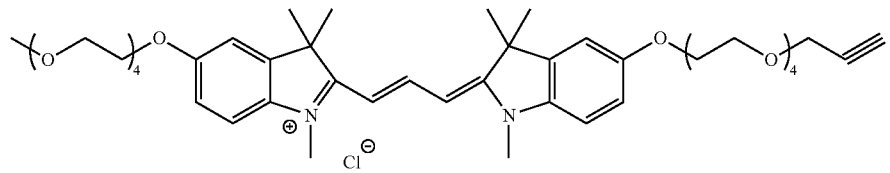
, and
B8
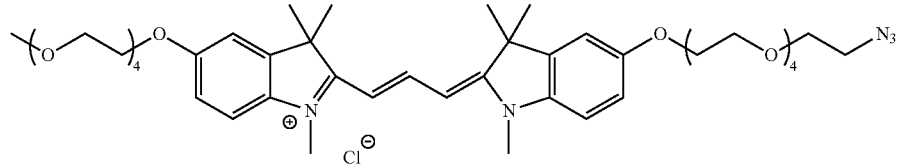
and tautomers and mixtures of two or more tautomers thereof; and pharmaceutically acceptable solvates and hydrates thereof.
14. The compound of claim 1, selected from:
C
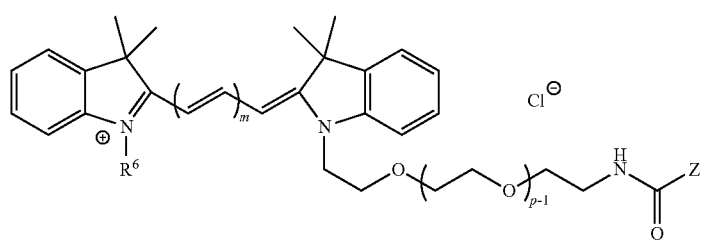
C1
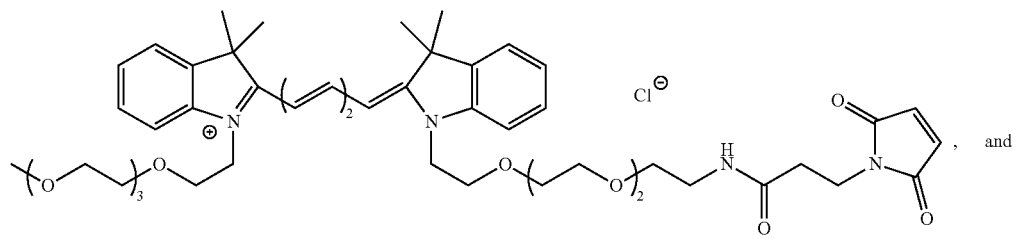
, and

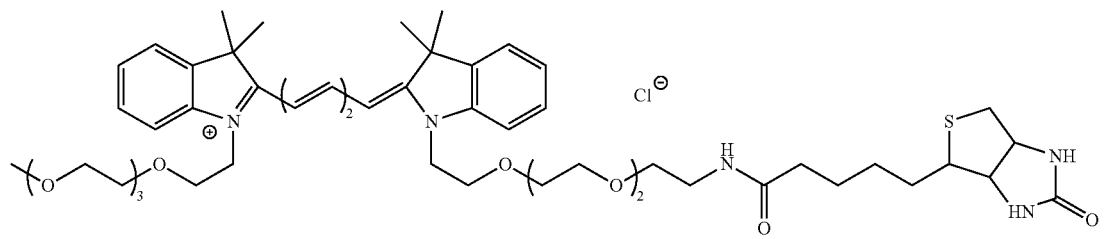
C2
and tautomers and mixtures of two or more tautomers thereof; and pharmaceutically acceptable solvates and hydrates thereof; wherein:
Z is (a) hydrogen, deuterium, halo, O, S, N, or Se; (b) $Z^1$ or $Z^6$; or (c) $R^{Xc}Z^1$, $R^{Xa}R^{Xc}$, $Z^1$, $R^{Xc}Z^6$, $R^{Xa}R^{Xc}Z^6$, $C(R^{Xa}R^{Xb})$, or $NR^{Xc}$.
15. The compound of claim 1, selected from:
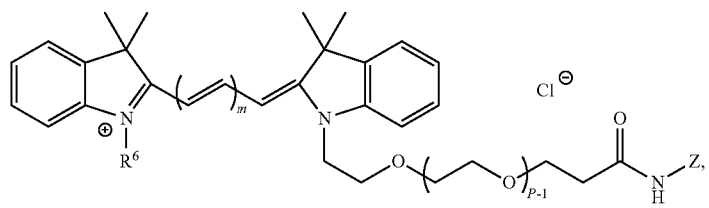
D
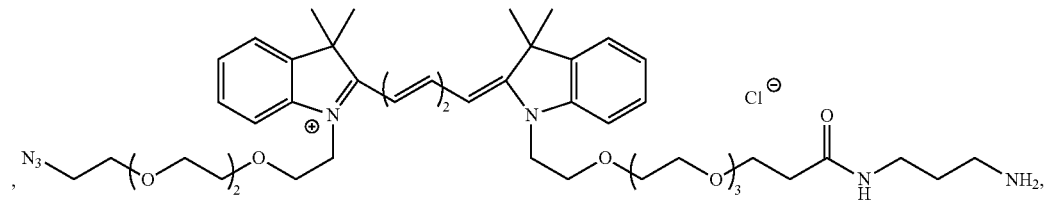
D1
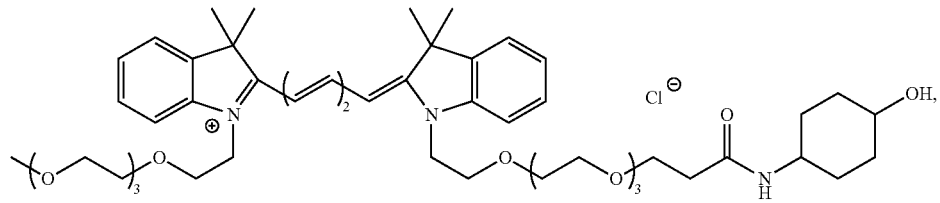
D2
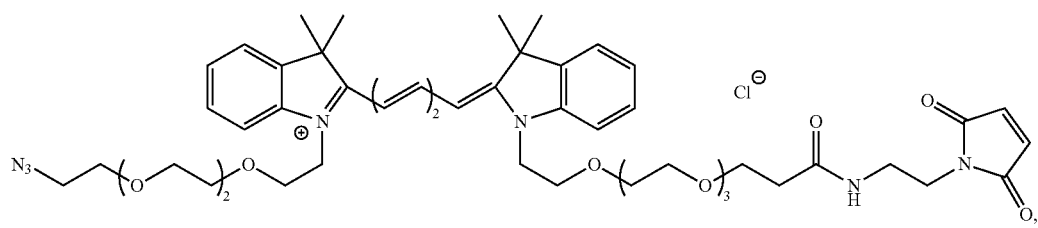
D3

-continued

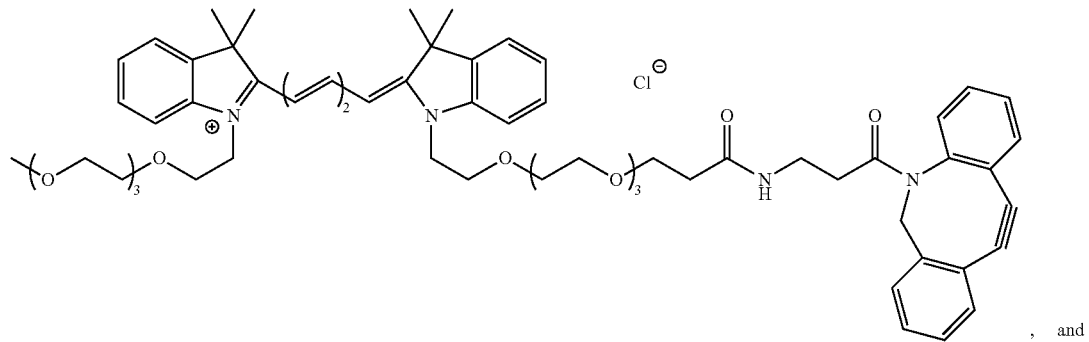

, and

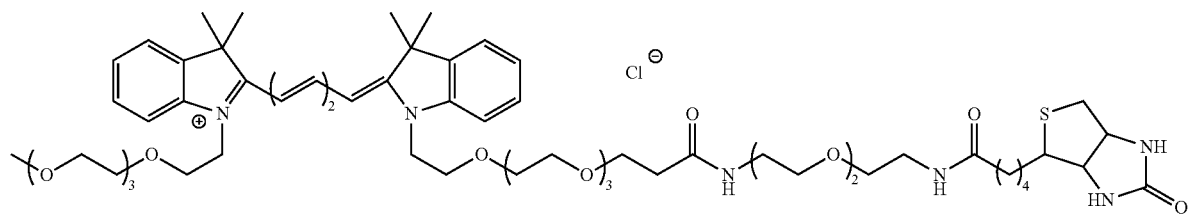

and tautomers and mixtures of two or more tautomers thereof; and pharmaceutically acceptable solvates and hydrates thereof; wherein:

Z is (a) hydrogen, deuterium, halo, O, S, N, or Se; (b) $Z^1$ or $Z^6$; or (c) $R^{Xc}Z^1$, $R^{Xc}Z^1$, $R^{Xa}R^{Xc}Z^1$, $R^{Xc}Z^6$, $R^{Xa}Z^6$, $C(R^{Xa}R^{Xb})$, or $NR^{Xc}$.

16. The compound of claim 1, selected from:

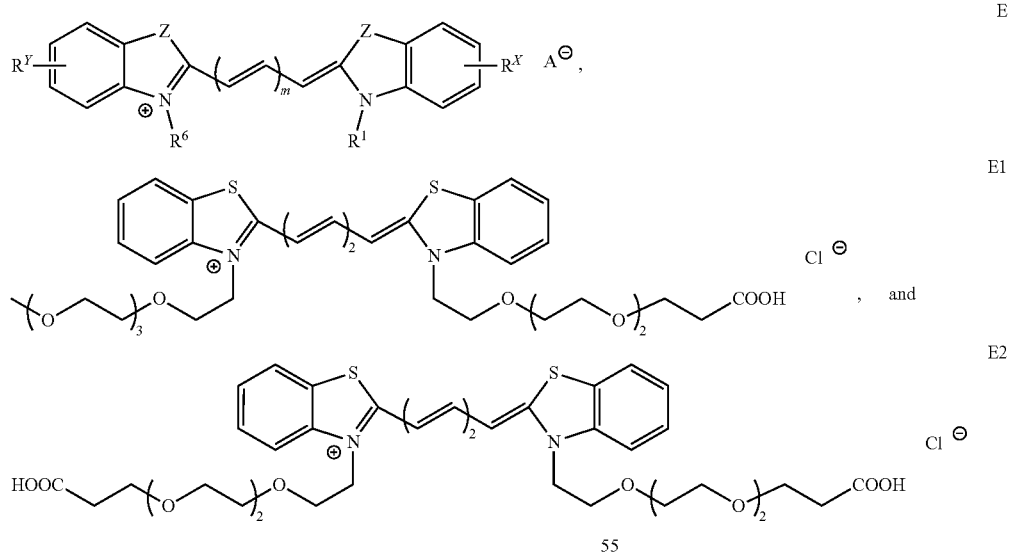

and tautomers and mixtures of two or more tautomers thereof; and pharmaceutically acceptable solvates and hydrates thereof; wherein:

$R^X$ and $R^Y$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$NR$^{1b}$R$^{1c}$, —OR$^{1a}$, —OC(O)R$^{1a}$, —OC(O)OR$^{1a}$, —OC(O) NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1b}$R$^{1c}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and wherein Z is (a) hydrogen, deuterium, halo, O, S, N, or Se; (b) $Z^1$ or $Z^6$; or (c) $R^{Xc}Z^1$, $R^{Xa}R^{Xc}Z^1$, $R^{Xc}Z^6$, $R^{Xa}R^{Xc}Z^6$, $C(R^{Xa}R^{Xb})$, or $NR^{Xc}$.

17. The compound of claim 1, selected from:

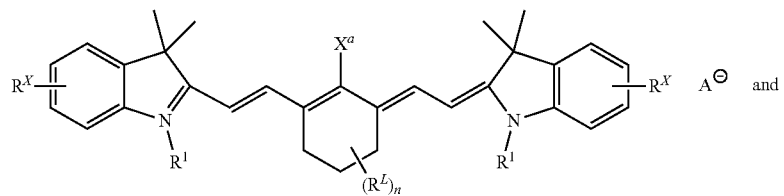

F

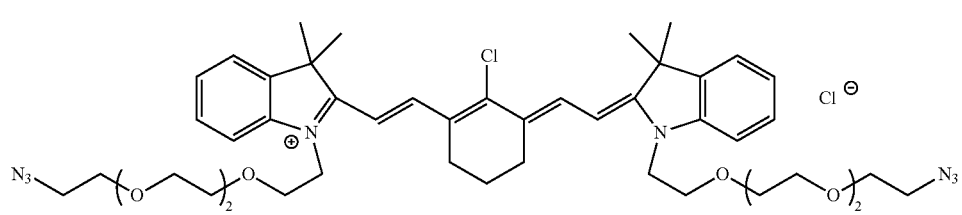

F1 and tautomers and mixtures of two or more tautomers thereof; and pharmaceutically acceptable solvates and hydrates thereof; wherein:

R$^X$ and R$^Y$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)$_2$R$^{1a}$, —S(O)$_2$R$^{1a}$, —S(O)NR$^{1b}$R$^{1c}$, or —S(O)$_2$NR$^{1b}$R$^{1c}$.

18. The composition of claim 1, selected from:

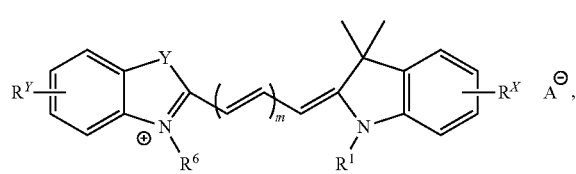

G

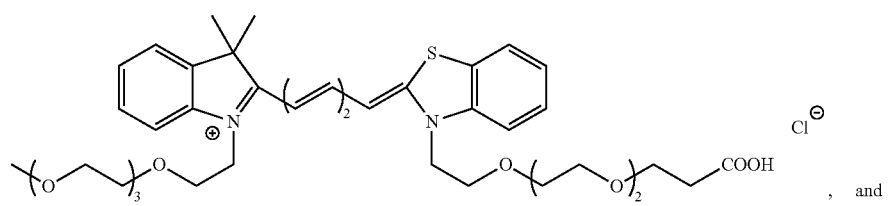

G1

, and

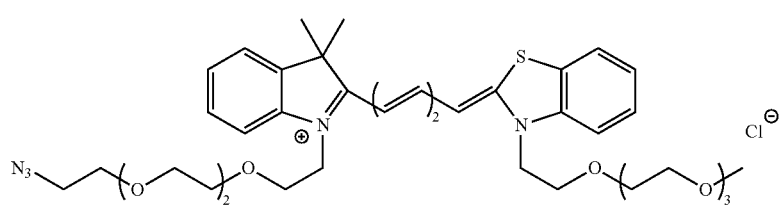

G2 and tautomers and mixtures of two or more tautomers thereof; and pharmaceutically acceptable solvates and hydrates thereof; wherein:

$R^X$ and $R^Y$ are each independently (a) hydrogen, deuterium, azido, cyano, halo, nitro, sulfo, —OPO$_3$H$_2$, or —PO$_3$H$_2$; (b) C$_{1-10}$ alkyl, C$_{2-10}$ alkenyl, C$_{2-10}$ alkynyl, C$_{3-15}$ cycloalkyl, C$_{6-20}$ aryl, C$_{7-20}$ aralkyl, heteroaryl, or heterocyclyl, each of which is optionally substituted with one or more substituents Q; or (c) —C(O)R$^{1a}$, —C(O)OR$^{1a}$ C(O)NR$^{1b}$R$^{1c}$, —C(NR$^{1a}$)NR$^{1b}$R$^{1c}$, —OR$^{1a}$ —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$m —OS(O)$_2$NR$^{1b}$R$^{1c}$, —NR$^{1b}$R$^{1c}$, —NR$^{1a}$(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —(O)R$^{1a}$, —S(O)$_2$R$^{1a}$, —S(O)NR$^{1b}$R$^{1c}$, or —S(O)$_2$NR$^{1b}$R$^{1c}$.

19. A pharmaceutical composition comprising the compound of claim 1, and a pharmaceutically acceptable excipient.

20. A method of labeling a biomolecule, comprising the step of contacting the biomolecule with the compound of claim 1.

\* \* \* \* \*